|||||||||||||||||||||||||||||||||||||||||||||||||||
US010328161B2

(12) United States Patent
Chang et al.

(10) Patent No.: US 10,328,161 B2
(45) Date of Patent: Jun. 25, 2019

(54) LUCIFERIN DERIVATIVES FROM BICYCLIC REACTANTS AND AMINOTHIOL DERIVATIVES AND METHODS OF USE THEREOF

(71) Applicant: The Regents of the University of California, Oakland, CA (US)

(72) Inventors: Christopher J. Chang, Berkeley, CA (US); Carolyn R. Bertozzi, Berkeley, CA (US); Genevieve C. van de Bittner, Berkeley, CA (US); Elena A. Dubikovskaya, Lausanne (CH)

(73) Assignee: The Regents of the University of California, Oakland, CA (US)

( * ) Notice: Subject to any disclaimer, the term of this patent is extended or adjusted under 35 U.S.C. 154(b) by 556 days.

(21) Appl. No.: 14/866,321

(22) Filed: Sep. 25, 2015

(65) Prior Publication Data
US 2016/0015835 A1    Jan. 21, 2016

Related U.S. Application Data

(62) Division of application No. 13/742,190, filed on Jan. 15, 2013, now Pat. No. 9,173,966.

(60) Provisional application No. 61/587,490, filed on Jan. 17, 2012.

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *C07F 5/02* | (2006.01) | |
| *C07D 277/68* | (2006.01) | |
| *C07K 7/06* | (2006.01) | |
| *G01N 33/58* | (2006.01) | |
| *A61K 31/427* | (2006.01) | |

(52) U.S. Cl.
CPC ........ *A61K 49/0021* (2013.01); *C07D 277/68* (2013.01); *C07F 5/02* (2013.01); *C07F 5/025* (2013.01); *C07K 7/06* (2013.01); *G01N 33/582* (2013.01); *A61K 31/427* (2013.01); *A61K 49/0017* (2013.01); *G01N 2333/96466* (2013.01)

(58) Field of Classification Search
None
See application file for complete search history.

(56) References Cited

U.S. PATENT DOCUMENTS

| | | | |
|---|---|---|---|
| 6,376,208 B1 * | 4/2002 | Kajiyama | C12Q 1/66 435/23 |
| 2010/0047172 A1 | 2/2010 | Cirillo et al. | |
| 2011/0201781 A1 | 8/2011 | Rao et al. | |
| 2011/0223625 A1 | 9/2011 | Kelts et al. | |

FOREIGN PATENT DOCUMENTS

WO    WO 2006-130551    12/2006

OTHER PUBLICATIONS

Van de Bittner et al. (PNAS 2010, 107, 21316-21321).*
Hampton et al. (FEBS Lett. 1997, 552-556).*
Liang, et al. "A Biocampatible Condensation Reaction for Controlled Assembly of Nanostructures in Live Cells", 2010, Nat Chem.m vol. 2 (1), pp. 54-60.
Takakura, et al., "Aminoluciferins as Functional Bioluminogenic Substrates of Firefly Luciferase", 2011, Chem. Asian J., vol. 6, pp. 1800-1810.

* cited by examiner

*Primary Examiner* — Michael G. Hartley
*Assistant Examiner* — Melissa J Perreira
(74) *Attorney, Agent, or Firm* — Bozicevic Field & Francis, LLP; Paula A. Borden

(57) ABSTRACT

The present disclosure features a condensation reaction and a luciferin-unmasking reaction that can be carried out under physiological conditions. In general, the condensation reaction involves reacting a bicyclic reactant with an aminothiol derivative, generating a luciferin or luciferin derivative. A luciferin can provide detectable luminescence. A luciferin derivative can be unmasked to provide detectable luminescence in a luciferin-unmasking reaction. The present disclosure provides bicyclic reactants and aminothiol derivatives suitable for use in the condensation reaction. The condensation and luciferin-unmasking reactions find use in a variety of applications, which are also provided.

7 Claims, 18 Drawing Sheets

LUCIFERIN DERIVATIVES FROM BICYCLIC REACTANTS AND AMINOTHIOL DERIVATIVES AND METHODS OF USE THEREOF

CROSS-REFERENCE

This application is a divisional of U.S. patent application Ser. No. 13/742,190, filed Jan. 15, 2013, which application claims the benefit of U.S. Provisional Patent Application No. 61/587,490, filed Jan. 17, 2012, which applications are incorporated herein by reference in their entirety.

STATEMENT REGARDING FEDERALLY SPONSORED RESEARCH

This invention was made with government support under Grant No. GM079465 and Grant No. GM 058867 awarded by the National Institutes of Health. The government has certain rights in the invention.

BACKGROUND

Luminescence is produced in certain organisms as a result of a luciferase-mediated oxidation reaction. Luminescence is produced by firefly luciferase and other enzymes when those enzymes are mixed with certain synthetic substrates.

Luciferases can also generate light via the oxidation of enzyme-specific substrates, e.g., luciferins. For firefly luciferase and all other beetle luciferases, light generation occurs in the presence of luciferin, magnesium ions, oxygen, and ATP. Luminescence, if any, can be measured using a luminometer or any suitable radiant energy-measuring device. A luminescence assay can be very rapid and sensitive.

SUMMARY

The present disclosure features a condensation reaction and a luciferin-unmasking reaction that can be carried out under physiological conditions or ex vivo prior to addition to cells or animals. In general, the condensation reaction involves reacting a bicyclic reactant with an aminothiol derivative, generating a luciferin or luciferin derivative. A luciferin can provide detectable luminescence. A luciferin derivative can be unmasked to provide detectable luminescence in a luciferin-unmasking reaction. The present disclosure provides bicyclic reactants and aminothiol derivatives suitable for use in the condensation reaction. The condensation and luciferin-unmasking reactions find use in a variety of applications, which are also provided.

Representative image of PC3M-luc cells with PCL-2, D-cysteine, and $H_2O_2$ in DMEM, log scale. Statistical analyses were performed with a two-tailed Student's t-test. *P<0.01 (D and E: n=6) and error bars are ±SEM.

Figure 7:
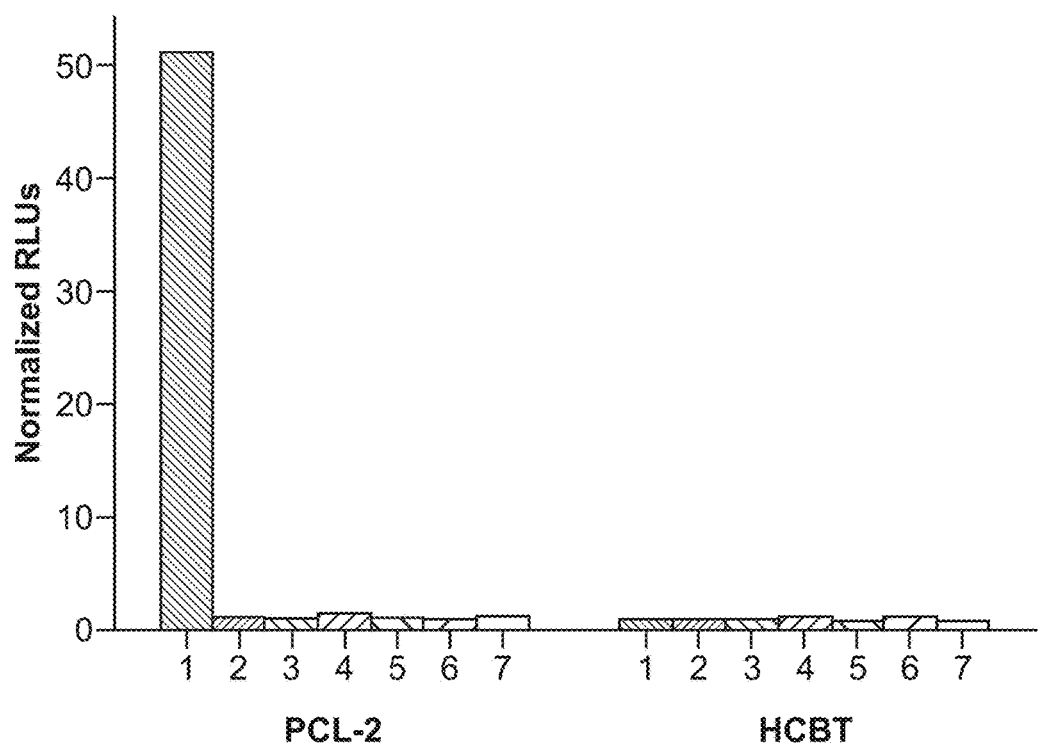

FIG. 7 shows a comparison of bioluminescent signal from PCL-2 and HCBT incubated with various ROS. Relative total bioluminescent signal, integrated over 10 or 45 min, from PCL-2 and HCBT (5 μM) incubated with 100 μM of various ROS (1: $H_2O_2$, 2: TBHP, 3: $HOCl^-$, 4: NO, 5: OH, 6: OtBu, or 7: $O_2^-$) for 60 min. Signals normalized to signal from PCL-2 or HCBT in the absence of any ROS. For luciferin detection, PCL-2/HCBT solutions were incubated with D-cysteine (5 μM) for 15 min, prior to addition of 100 μg/mL luciferase in 50 mM Tris buffer with 10 mM $MgCl_2$, 0.1 mM $ZnCl_2$, and 2 mM ATP (pH 7.4).

Figure 8:
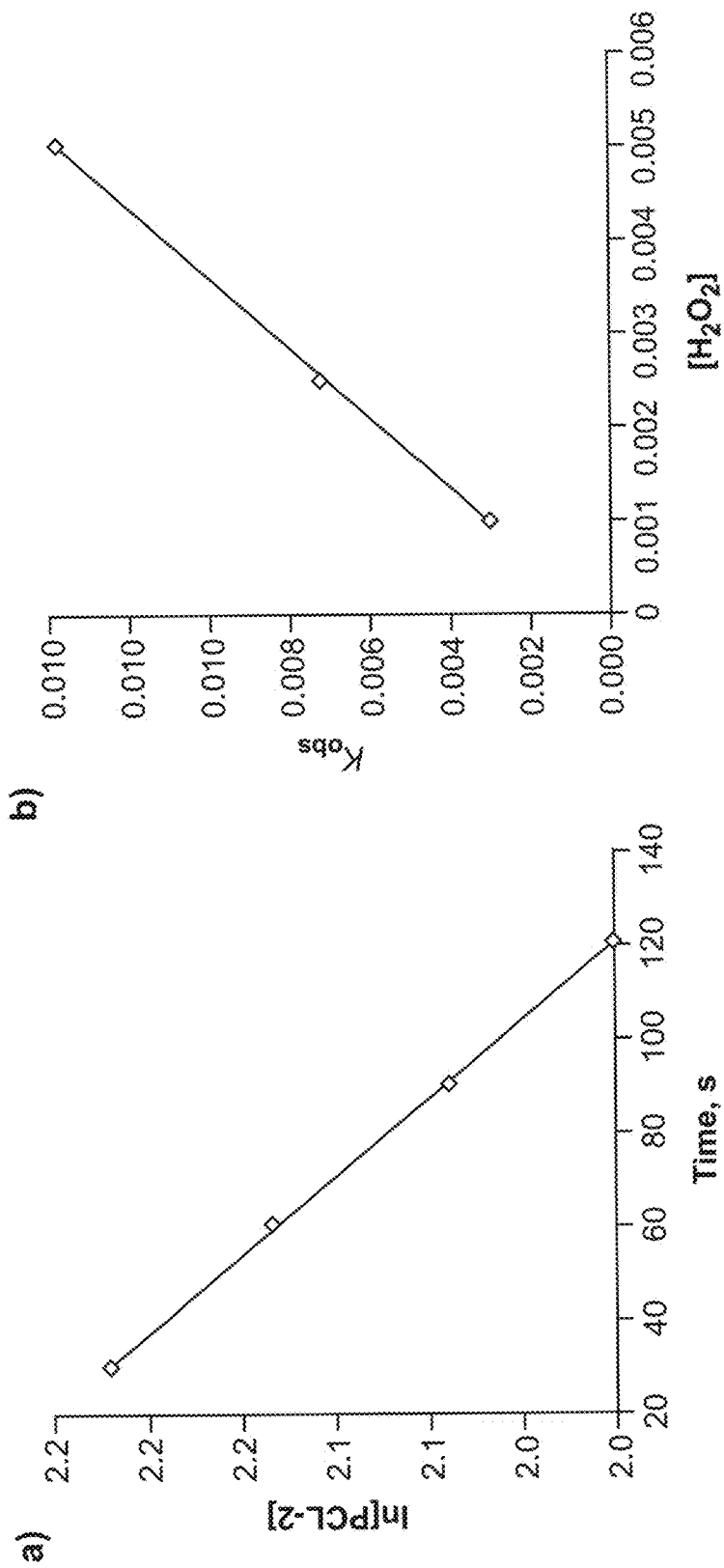

FIG. 8 depicts a kinetic studies for determination of the second-order rate constant for the reaction between PCL-2 and $H_2O_2$. (a) Representative plot of ln[PCL-2] versus time for the pseudo-first-order reaction between PCL-2 and $H_2O_2$ for determination of $k_{obs}$. (b) Plot of $k_{obs}$ versus $[H_2O_2]$ for determination of the second-order rate constant.

Figure 9:
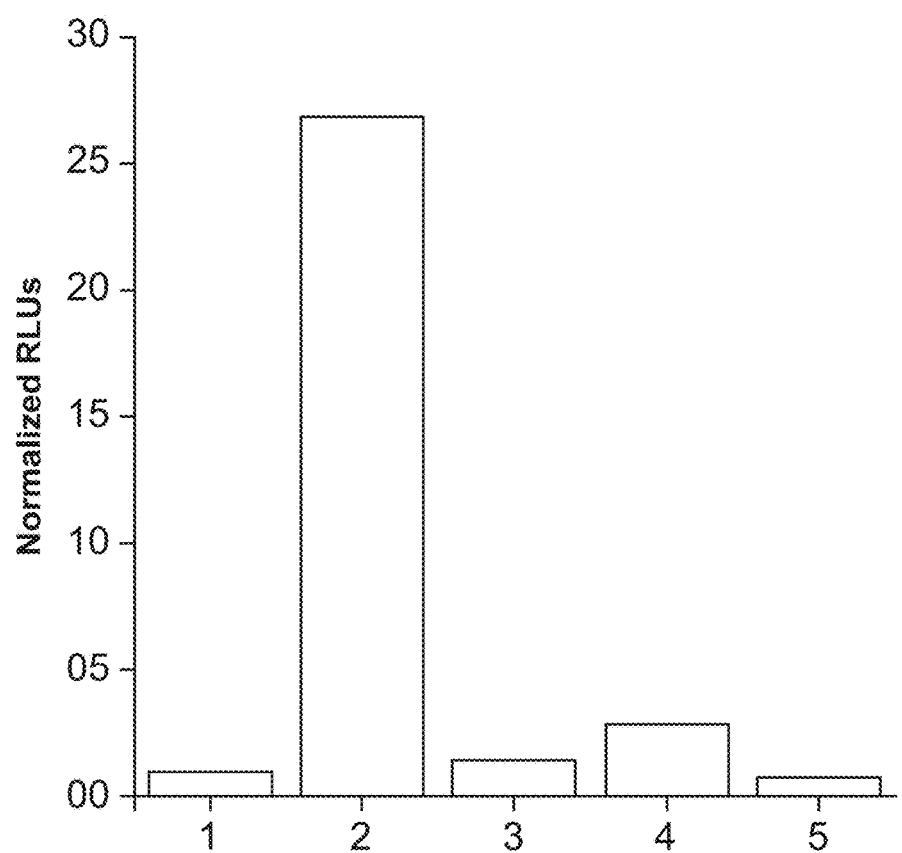

FIG. 9 shows the selective and sensitive bioluminescent detection of Caspase 8 activity by IETDC. Total bioluminescent signal, integrated over 10 min, from IETDC (5 μM) and HCBT (5 μM) alone or incubated with various caspase enzymes (3 and 8:1 unit; 9:0.001 unit) or caspase 8 and Q-VD-OPh (10 μM) for 60 min. From left to right, 1: IETDC and HCBT; 2: IETDC, HCBT, and caspase 8; 3: IETDC, HCBT, caspase 8, and Q-VD-OPh; 4: IETDC, HCBT, and caspase 3; 5: IETDC, HCBT, and caspase 9. Signals normalized to signal from IETDC and HCBT in the absence of the caspase enzymes. To quantify luciferin formation, 100 μg/mL luciferase in 50 mM Tris buffer with 10 mM $MgCl_2$, 0.1 mM $ZnCl_2$, and 2 mM ATP (pH 7.4) was added to 100 μL of each IETDC/HCBT solution.

Figure 10:
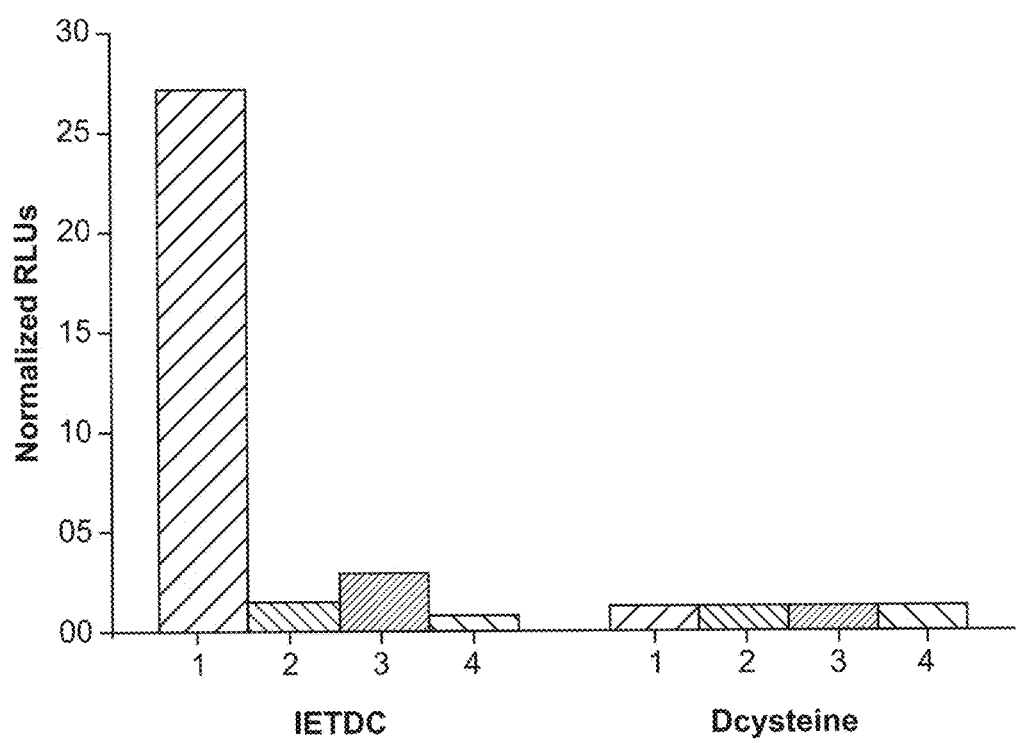

FIG. 10 depicts a comparison of bioluminescent signal from IETDC and D-cysteine incubated with various caspase enzymes. Relative total bioluminescent signal, integrated over 10 min, from IETDC and D-cysteine (5 μM) incubated with various caspase enzymes and caspase 8 plus Q-VD-OPh for 60 min (1: caspase 8, 2: caspase 8+inhibitor, 3: caspase 3, 4: caspase 9). Signals normalized to signal from IETDC or D-cysteine in the absence of any caspase enzymes and Q-VD-OPh. For luciferin detection, 100 μg/mL luciferase in 50 mM Tris buffer with 10 mM $MgCl_2$, 0.1 mM $ZnCl_2$, and 2 mM ATP (pH 7.4) was added to the IETDC and D-cysteine solutions, which also contained HCBT (5 μM).

Figure 11:
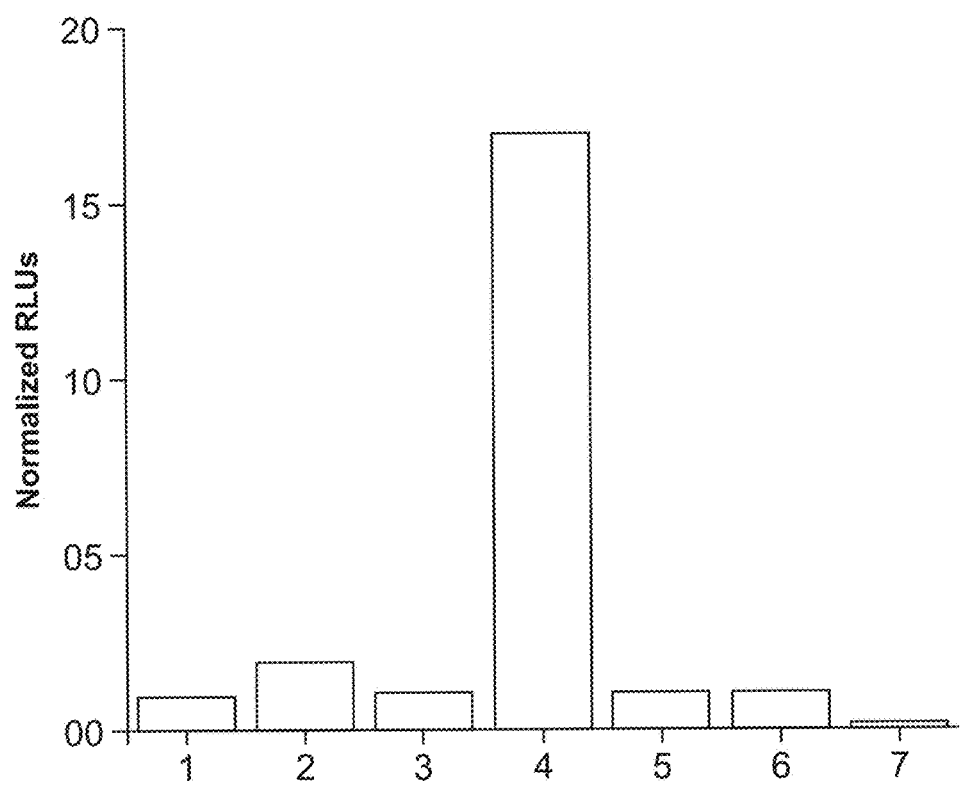

FIG. 11 depicts the dual detection of $H_2O_2$ and Caspase 8 via in situ luciferin formation. Total bioluminescent signal, integrated over 10 min, from PCL-2 (10 μM) and IETDC (10 μM) alone or incubated with $H_2O_2$ (250 μM) and caspase 8 (1 unit) in the presence or absence of catalase (1 unit) and/or Q-VD-OPh (10 μM). From left to right, 1: PCL-2 and IETDC; 2: PCL-2, IETDC, and $H_2O_2$; 3: PCL-2, IETDC, and caspase 8; 4: PCL-2, IETDC, $H_2O_2$, and caspase 8; 5: PCL-2, IETDC, $H_2O_2$, caspase 8, and catalase; 6: PCL-2, IETDC, $H_2O_2$, caspase 8, and Q-VD-OPh; 7: PCL-2, IETDC, $H_2O_2$, caspase 8, catalase, and Q-VD-OPh. Signals normalized to signal from PCL-2 and IETDC in the absence of $H_2O_2$ and caspase 8. To quantify luciferin formation, 100 μg/mL luciferase in 50 mM Tris buffer with 10 mM $MgCl_2$, 0.1 mM $ZnCl_2$, and 2 mM ATP (pH 7.4) was added to the PCL-2/IETDC solutions.

Figure 12:
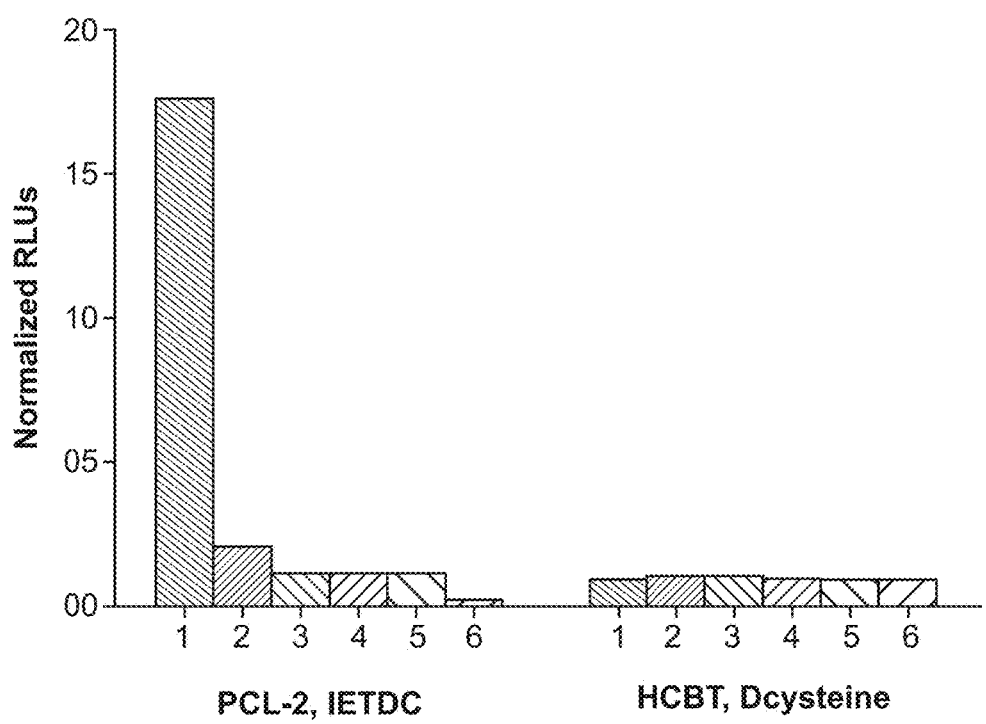

FIG. 12 depicts a comparison of bioluminescent signal from PCL-2/IETDC and HCBT/D-cysteine for in vitro dual-analyte detection. On left, total bioluminescent signal, integrated over 10 min, from PCL-2 (10 μM) and IETDC (10 μM) alone or incubated with $H_2O_2$ (250 μM) and caspase 8 (1 unit) in the presence or absence of catalase (1 unit) and/or Q-VD-OPh (10 μM). From left to right, 1: PCL-2, IETDC, $H_2O_2$, and caspase 8; 2: PCL-2, IETDC, $H_2O_2$, and caspase 8; 3: PCL-2, IETDC, and caspase 8; 4: PCL-2, IETDC, $H_2O_2$, caspase 8, and catalase; 5: PCL-2, IETDC, $H_2O_2$, caspase 8, and Q-VD-OPh; 6: PCL-2, IETDC, $H_2O_2$, caspase 8, catalase, and Q-VD-OPh. On right, total bioluminescent signal, integrated over 45 min, from HCBT (5 μM) and D-cysteine (5 μM) alone or incubated with $H_2O_2$ (250 μM) and/or caspase 8 (1 unit) in the presence or absence of catalase (1 unit) and/or Q-VD-OPh (10 μM). From left to right, 1: HCBT, D-cysteine, $H_2O_2$, and caspase 8; 2: HCBT, D-cysteine, and $H_2O_2$; 3: HCBT, D-cysteine, and caspase 8; 4: HCBT, D-cysteine, $H_2O_2$, caspase 8, and catalase; 5: HCBT, D-cysteine, $H_2O_2$, caspase 8, and Q-VD-OPh; 6: HCBT, D-cysteine, $H_2O_2$, caspase 8, catalase, and Q-VD-OPh. Signals normalized to signal from PCL-2/IETDC or HCBT/D-cysteine alone. To quantify luciferin formation, 100 μg/mL luciferase in 50 mM Tris buffer with 10 mM $MgCl_2$, 0.1 mM $ZnCl_2$, and 2 mM ATP (pH 7.4) was added to the PCL-2/IETDC or HCBT/D-cysteine solutions.

Figure 13:
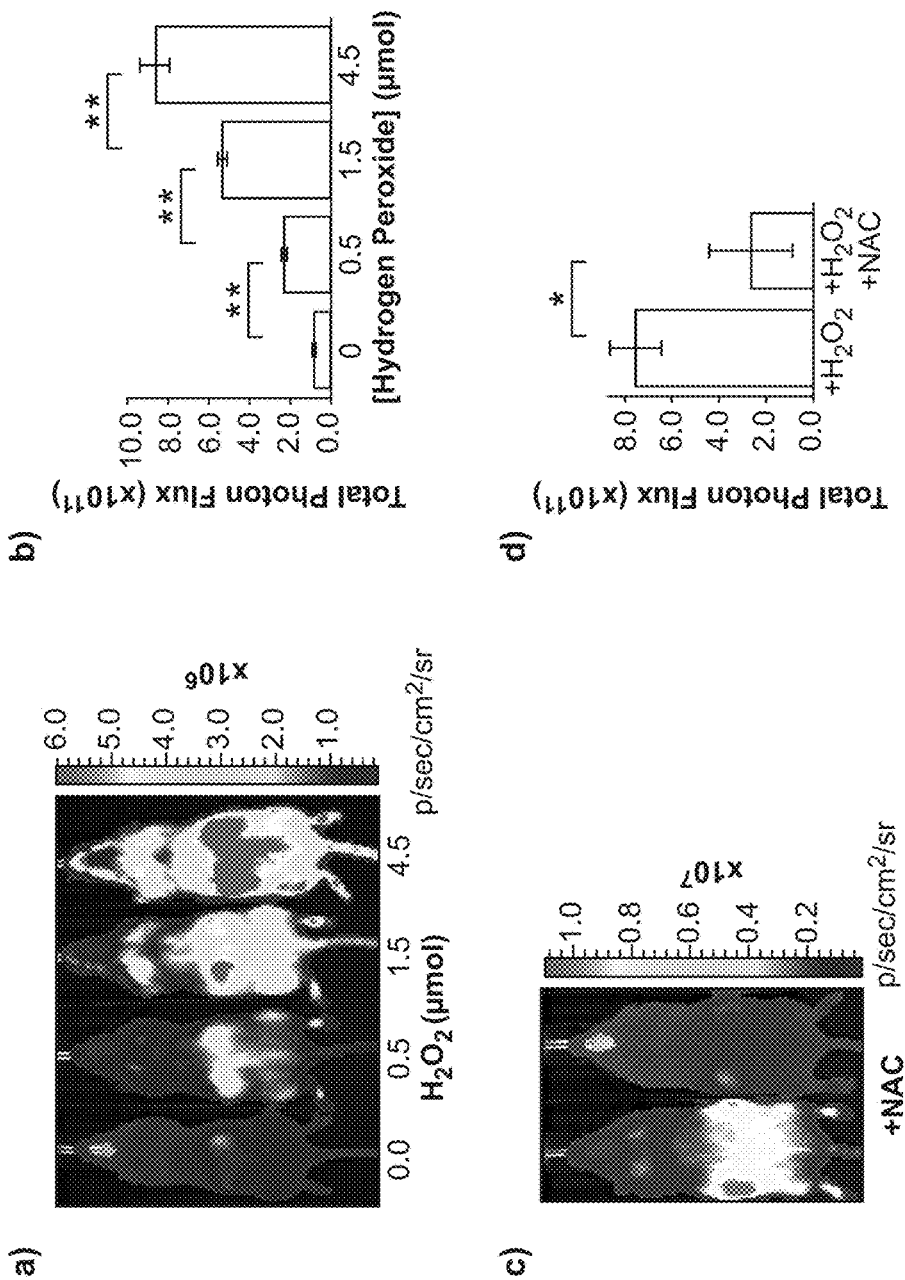

FIG. 13 depicts the Bioluminescent response of PCL-2 to $H_2O_2$ in FVB-luc$^+$ mice. (a) Representative image (10 min post-injection) for mice injected with a mixture of PCL-2 and D-cysteine (IP, 0.05 μmol each, in 50 μL of 1:1 DMSO:PBS) immediately prior to injection of $H_2O_2$ (IP, 0, 0.5, 1.5, or 4.5 μmol, left to right, in 100 μL of PBS). (b) Total photon flux, 0-15 min post-injection, for mice injected with PCL-2 and D-cysteine±$H_2O_2$. (c) Representative image (10 min post-injection) for mice injected with NAC (IP, 10 mg/kg in 25 μL of PBS, pH 7-8) or PBS (IP, 25 μL) two min prior to injection of a mixture of PCL-2 and D-cysteine (IP, 0.05 μmol each, in 50 μL of 1:1 DMSO:PBS) and a solution of $H_2O_2$ (IP, 1.5 μmol in 75 μL of PBS). (d) Total photon flux, 0-15 min post-injection, for mice injected with PCL-2 and $H_2O_2$ in the presence or absence of NAC. Statistical analyses were performed with a two-tailed Student's t-test. *P<0.05, **P<0.01 (B: n=4, D: n=3) and error bars are ±SEM.

Figure 14:
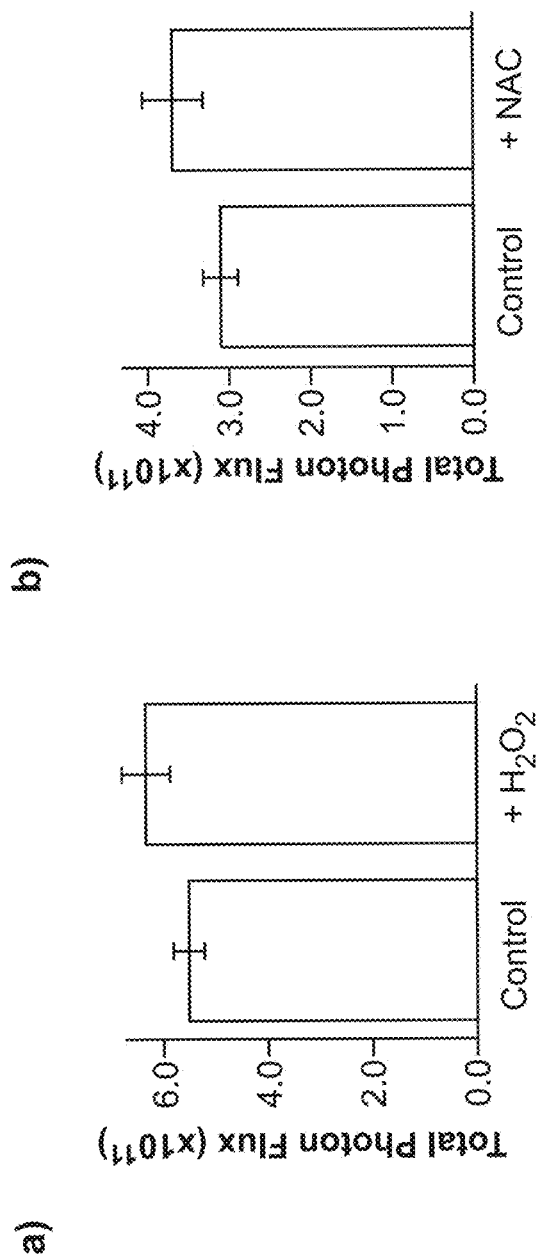

FIG. 14 depicts bioluminescent signals from HCBT and D-cysteine with $H_2O_2$ and NAC in FVB-luc$^+$ mice. (a) Total photon fluxes, 0-15 min post-injection, for mice (n=4-5) injected with a mixture of HCBT and D-cysteine (IP, 0.01 μmol each, in 50 μL of 1:1 DMSO:PBS) immediately prior to injection of $H_2O_2$ (IP, 4.5 μmol in 100 μL PBS) or vehicle (IP, 100 μL PBS). (b) Total photon fluxes, 0-15 min post-injection, for mice (n=3) injected with a mixture of HCBT and D-cysteine (IP, 0.01 μmol each, in 50 μL of 1:1 DMSO:PBS) immediately prior to injection of NAC (IP, 10 mg/kg in 100 μL PBS) or vehicle (IP, 100 μL PBS). Error bars are ±SEM.

Figure 15:
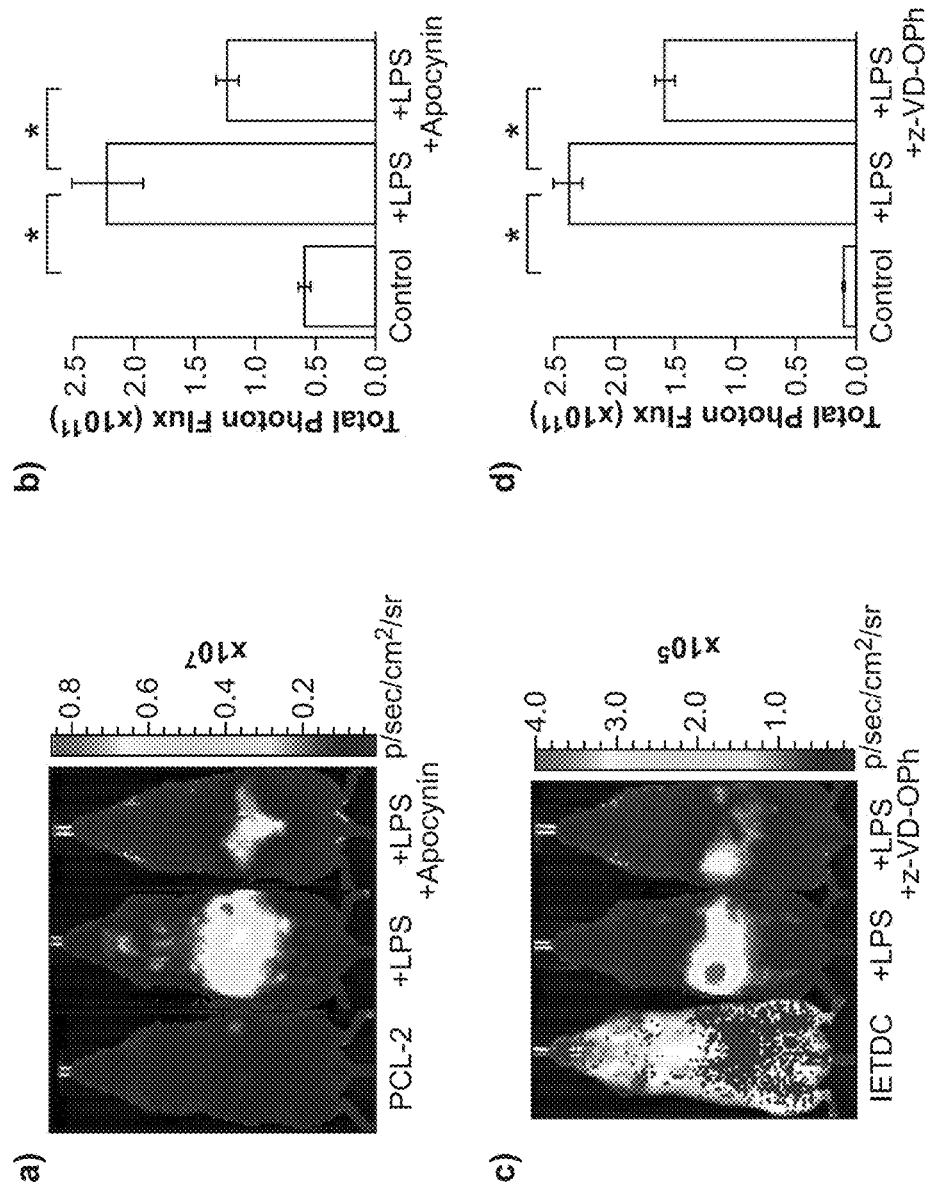

FIG. 15 depicts the bioluminescent signal from PCL-2 and IETDC following lipopolysaccharide challenge. (a) Representative image (10 min post-injection) of mice 6 h after injection of LPS (IP, 3 mg/kg in 50 μL of saline) or saline vehicle (IP, 50 μL). Two minutes prior to imaging, mice were treated with apocynin (IP, 10 mg/kg in 20 μL of DMSO) or vehicle (IP, 20 μL DMSO). Imaging was started following injection of a mixture of PCL-2 and D-cysteine (IP, 0.05 μmol each, in 50 μL of 1:1 DMSO:PBS). (b) Total photon flux, 0-15 min post-injection, for mice injected with PCL-2 and D-cysteine, ±LPS, and ±apocynin. (c) Representative image (30 min post-injection) of mice 6 h after injection of LPS (IP, 3 mg/kg in 50 μL of saline) or vehicle (IP, 50 μL saline). Thirty minutes prior to imaging, mice were treated with z-VD(OMe)-OPh (IP, 1 μmol in 20 μL of DMSO) or vehicle (IP, 20 μL DMSO). Imaging was started following injection of a mixture of IETDC and HCBT (IP, 0.05 μmol each, in 50 μL of 1:1 DMSO:PBS). (d) Total photon flux, 15-45 min post-injection, for mice injected with IETDC and HCBT, ±LPS, and ±z-VD(OMe)-OPh. Statistical analyses were performed with a two-tailed Student's t-test. *P<0.05 (B and D: n=3-4) and error bars are ±SEM.

Figure 16:
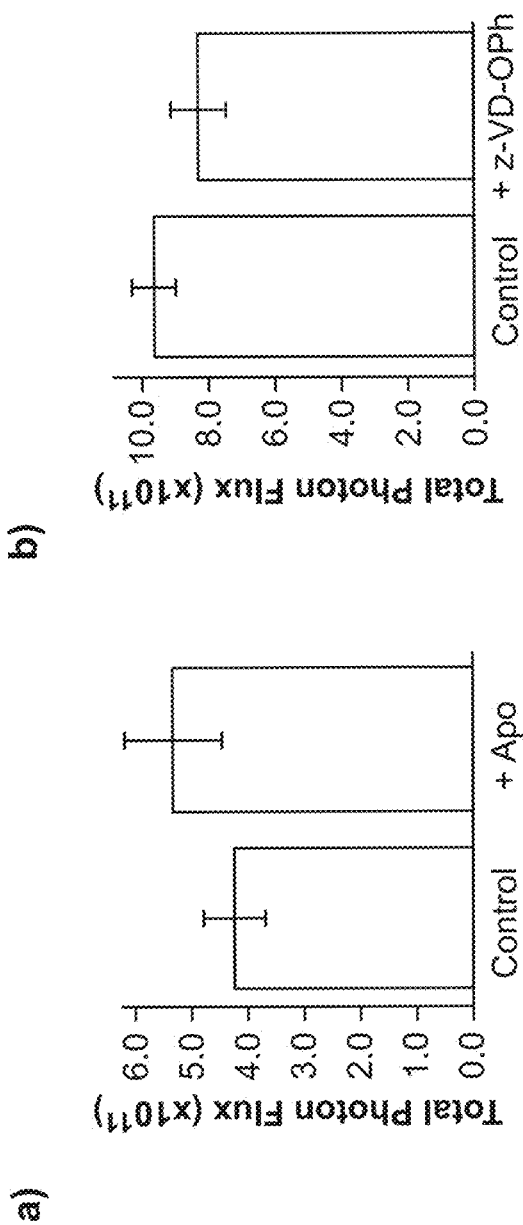

FIG. 16 shows bioluminescent signals from HCBT and D-cysteine with apocynin and z-VD(OMe)-OPh in FVB-luc+ mice. (a) Total photon fluxes, 0-15 min post-injection, for mice (n=3) injected with apocynin (IP, 10 mg/kg in 20 μL DMSO) or vehicle (IP, 20 μL DMSO) two min prior to injections of a mixture of HCBT and D-cysteine (IP, 0.01 μmol each, in 50 μL of 1:1 DMSO:PBS). (b) Total photon fluxes, 15-45 min post-injection, for mice (n=3) injected with z-VD(OMe)-OPh (IP, 1 μmol in 20 μL DMSO) or vehicle (IP, 20 μL DMSO) 30 min prior to injections of a mixture of HCBT and D-cysteine (IP, 0.01 μmol each, in 50 μL of 1:1 DMSO:PBS). Error bars are ±SEM.

Figure 17:
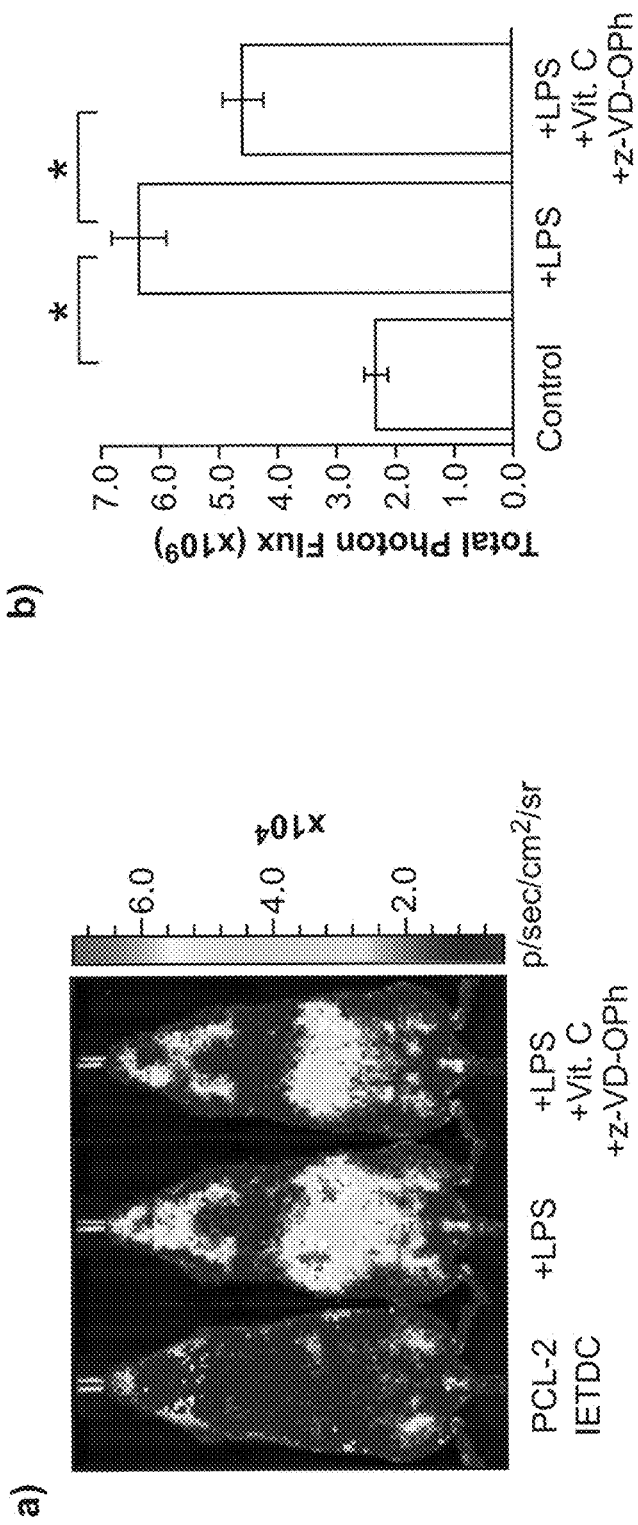

FIG. 17 shows dual imaging of $H_2O_2$ and Caspase 8 following lipopolysaccharide challenge. (a) Representative image (45 min post-injection) of mice following injection of ascorbic acid (IP, 200 mg/kg in 30 μL of saline), LPS (IP, 3 mg/kg in 50 μL of saline), z-VD(OMe)-OPh (IP, 1 μmol in 20 μL of DMSO), and/or their respective vehicles (IP, 30 or 50 μL saline or 20 μL DMSO). Mice were treated with ascorbic acid or vehicle 4.5 h prior to imaging, LPS or vehicle 4 h prior to imaging, and z-VD(OMe)-OPh or vehicle 2 h prior to imaging. Imaging was started following injection of a mixture of PCL-2 and IETDC (IP, 0.05 μmol each, in 50 μL of 7:3 DMSO:PBS). (b) Total photon flux, 30-60 min post-injection, for mice injected with PCL-2 and IETDC, ±LPS, ±z-VD(OMe)-OPh, and ±ascorbic acid. Statistical analyses were performed with a two-tailed Student's t-test. *P<0.05 (B and D: n=3-4) and error bars are ±SEM.

Figure 18:
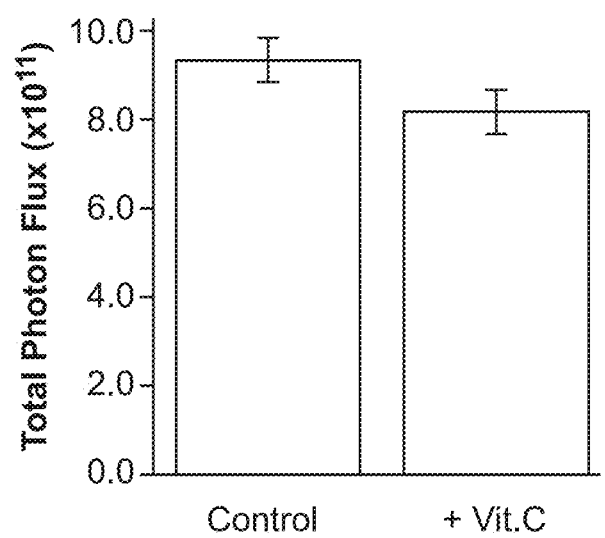

FIG. 18 depicts bioluminescent signals from HCBT and D-cysteine with ascorbic acid in FVB-luc+ mice. Total photon fluxes, 30-60 min post-injection, for mice (n=3-4) injected with ascorbic acid (IP, 200 mg/kg in 30 μL saline) or vehicle (IP, 30 μL saline) 4.5 h prior to injections of a mixture of HCBT and D-cysteine (IP, 0.01 μmol each, in 50 μL of 1:1 DMSO:PBS). Error bars are ±SEM.

DEFINITIONS

The following terms have the following meanings unless otherwise indicated. Any undefined terms have their art recognized meanings.

The term "cell" in the context of in vivo and ex vivo applications is meant to encompass eukaryotic and prokaryotic cells of any genus or species. e.g., eukaryotic cells including mammalian cells. "Cell" is also meant to encompass both normal cells and diseased cells, e.g., cancerous cells. In many embodiments, the cells are living cells. In many embodiments, the cells are nucleated cells.

The term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

The term "luciferase" refers to an enzyme that oxidizes a corresponding luciferin, thereby causing bioluminescence. Luciferase enzymes can be found in bacteria, fireflies, fish, squid, dinoflagellates, and other organisms capable of bioluminescence.

The term "physiological conditions" is meant to encompass those conditions compatible with living cells, e.g., predominantly aqueous conditions of a temperature, pH, salinity, etc. that are compatible with living cells.

The term "reaction partner" is meant describe a molecule or molecular moiety that specifically reacts with another reaction partner. Exemplary reaction partners are those of a subject reaction, i.e., a bicyclic reactant and an aminothiol derivative.

The term "substantially purified" refers to a compound that is removed from its natural environment or its synthetic environment and is at least 60% free, at least 75% free, at least 90% free, at least 95% free, at least 98% free, or at least 99% free from other components with which it is naturally associated, or is at least 60% free, at least 75% free, at least 90% free, at least 95% free, at least 98% free, or at least 99% free from contaminants associated with synthesis of the compound.

The term "derivative" refers, for example, to compounds that are derived from another compound and maintain the same general structure as the compound from which they are derived.

"Alkyl" refers to monovalent saturated aliphatic hydrocarbyl groups having from 1 to 10 carbon atoms, e.g., from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2$—), and neopentyl (($CH_3$)$_3$CCH$_2$—).

"Substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups, e.g., having from 1 to 6 carbon atoms (e.g., from 1 to 3 carbon atoms) that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

"Alkane" refers to alkyl group and alkylene group, as defined herein.

"Alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

"Alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

"Substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkoxyamino" refers to the group —NH-alkoxy, wherein alkoxy is defined herein.

"Haloalkoxy" refers to the groups alkyl-O— wherein one or more hydrogen atoms on the alkyl group have been substituted with a halo group and include, by way of examples, groups such as trifluoromethoxy, and the like.

"Haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

"Alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms, e.g., from 2 to 4 carbon atoms; and having at least 1, e.g., from 1 to 2, sites of double bond unsaturation. This term includes, by way of example, bi-vinyl, allyl, and but-3-en-1-yl. Included within this term are the cis and trans isomers or mixtures of these isomers.

"Substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms, e.g., 2 to 3 carbon atoms, and having at least 1 (e.g., from 1 to 2) sites of triple bond unsaturation. Examples of such alkynyl groups include acetylenyl (—C≡CH), and propargyl (—$CH_2$C≡CH).

"Substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3$C(O)—

"Acylamino" refers to the groups —$NR^{20}$C(O)alkyl, —$NR^{20}$C(O) substituted alkyl, N $R^{20}$C(O)cycloalkyl, —$NR^{20}$C(O) substituted cycloalkyl, —$NR^{20}$C(O)cycloalkenyl, —$NR^{20}$C(O) substituted cycloalkenyl, —$NR^{20}$C(O) alkenyl, —$NR^{20}$C(O) substituted alkenyl, —$NR^{20}$C(O) alkynyl, —$NR^{20}$C(O) substituted alkynyl, —$NR^{20}$C(O)aryl, —$NR^{20}$C(O) substituted aryl, —$NR^{20}$C(O)heteroaryl, —$NR^{20}$C(O) substituted heteroaryl, —$NR^{20}$C(O)heterocyclic, and —$NR^{20}$C(O) substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}$C(O) $NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

"Alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

"Aminocarbonylalkoxy" refers to the group —O—C(O)NRR where each R is independently hydrogen, alkyl, substituted alkyl, aryl, heteroaryl, or heterocyclyl wherein alkyl, substituted alkyl, aryl, heteroaryl, and heterocyclyl are as defined herein.

"Acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O— substituted aryl, —O—C(O)O-cycloalkyl, —O—C(O)O-substituted cycloalkyl, —O—C(O)O— cycloalkenyl, —O—C(O)O-substituted cycloalkenyl, —O—C(O)O-heteroaryl, —O—C(O)O— substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

"Substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond, e.g., from 1 to 2 double bonds.

"Substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

"Heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$- moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

"Heterocyclylthio" refers to the group heterocyclic-S—.

"Heterocyclene" refers to the diradical group formed from a heterocycle, as defined herein.

"Hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

"Substituted thioalkoxy" refers to the group —S-substituted alkyl.

"Thioaryloxy" refers to the group aryl-S— wherein the aryl group is as defined herein including optionally substituted aryl groups also defined herein.

"Thioheteroaryloxy" refers to the group heteroaryl-S— wherein the heteroaryl group is as defined herein including optionally substituted aryl groups as also defined herein.

"Thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O) NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C (O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the present disclosure and the other a typical counter ion such as chloride, or two ionized compounds disclosed herein can serve as counter ions for such divalent alkali earth ions, or a doubly ionized compound of the present disclosure can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$ (M$^+$)$_2$, -P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$) NR$^{80}$R$^{80}$, —OC(O)R$^{70}$, —OC(S)R$^{70}$, —O CO$_2$$^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C (NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$ O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$) R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

A "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

A "salt thereof" means a compound formed when the hydrogen of an acid is replaced by a cation, such as a metal cation or an organic cation and the like. Where applicable, the salt is a pharmaceutically acceptable salt, although this is not required for salts of compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH-ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cyanobenzothiazole derivative" includes a plurality of such derivatives and reference to "the luciferin" includes reference to one or more luciferins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure features a condensation reaction and a luciferin-unmasking reaction that can be carried out under physiological conditions or ex vivo prior to addition to cells or animals. In general, the condensation reaction involves reacting a bicyclic reactant (in protected or deprotected version) with an aminothiol derivative (in protected or deprotected version), generating a luciferin or luciferin derivative. A luciferin can provide detectable luminescence. A luciferin derivative can be unmasked to provide detectable luminescence in a luciferin-unmasking reaction. The present disclosure provides bicyclic reactants and aminothiol derivatives suitable for use in the condensation reaction and luciferin-unmasking reaction to generate a luciferin or luciferin derivative. The condensation and luciferin-unmasking reactions find use in a variety of applications, which are also provided.

In certain embodiments, the bicyclic reactants and aminothiol derivatives can comprise protecting group moieties involved in detection of one or more biological processes or biomolecules. For example, deprotection or release of protecting group moieties on a bicyclic reactant and an aminothiol derivative can allow a condensation reaction to proceed to produce a luciferin or luciferin derivative. Luciferin can provide detectable luminescence.

If a luciferin derivative is formed from the condensation reaction, the luciferin derivative comprises a protecting group moiety in manner such that the luciferin derivative does not provide detectable luminescence. Upon deprotection or release of the protecting group moiety from the luciferin derivative in a luciferin-unmasking reaction, a luciferin is formed and can provide detectable luminescence.

An example of condensation and luciferin-unmasking reactions is shown below.

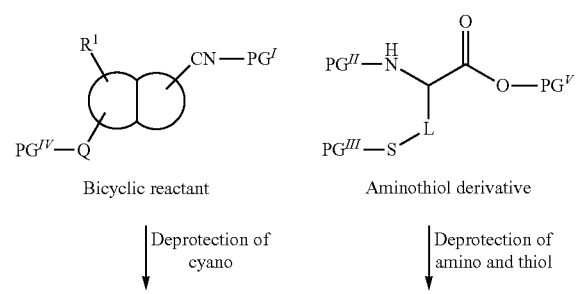

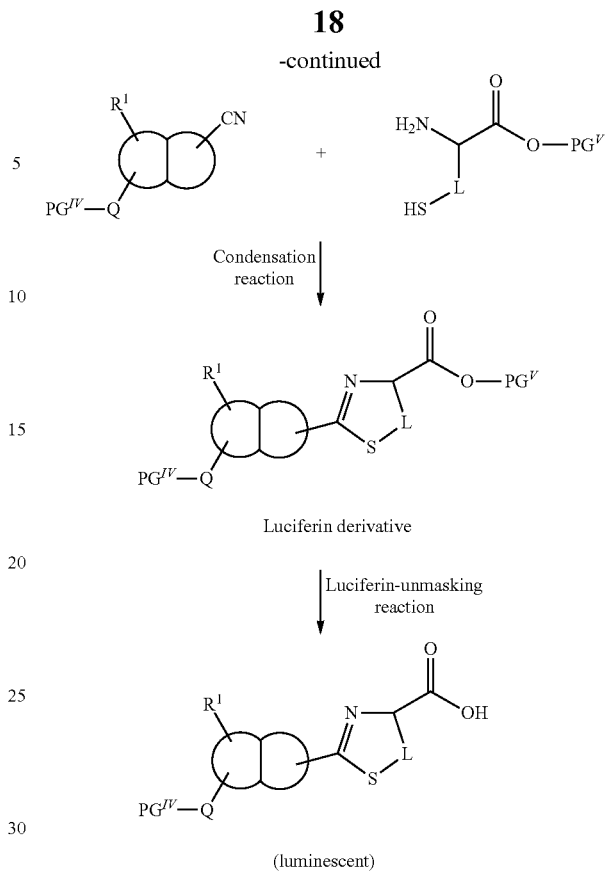

In certain embodiments, the deprotection or release of the protecting group moiety in the luciferin-unmasking reaction can occur before the condensation reaction. The protecting groups for heteroatom functional group or carboxyl substituents of the reactants are deprotected before deprotection or release of protecting group moieties for the condensation reaction. Thus, upon occurrence of the condensation reaction, a luciferin is generated.

An example of luciferin-unmasking and condensation reactions is shown below.

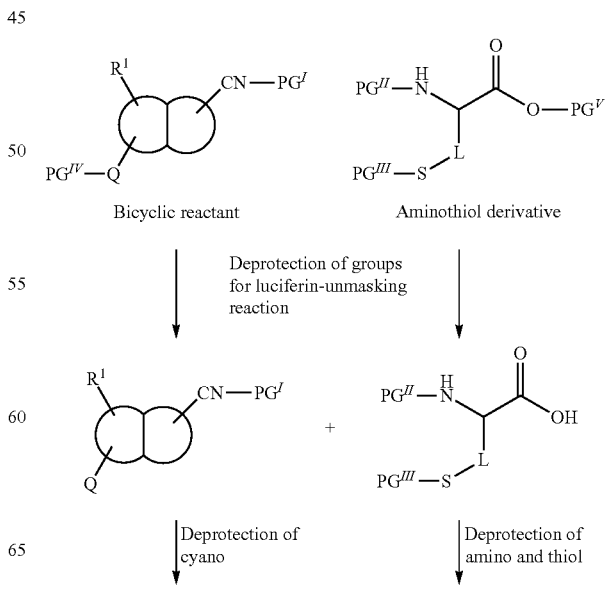

-continued

[Chemical scheme: R¹-bicyclic-CN with Q substituent + H₂N-CH(L-SH)-COOH → Condensation reaction → luciferin-type product (luminescent)]

The selectivity of the reaction and its compatibility with aqueous environments provides for its application in vivo and in vitro. The reaction is compatible with living cells.

The condensation reaction and luciferin-unmasking reaction can serve as an assay for the detection of one or more biological processes or biomolecules. Luminescence can be detected if luciferin is formed from the condensation reaction and luciferin-unmasking reaction. The condensation reaction and luciferin-unmasking reaction are dependent on the deprotection and release of protecting group moieties. Thus, under certain biological conditions or in the presence of certain biomolecules, the protecting group moieties are deprotected or released and the condensation reaction and/or luciferin-unmasking reaction can occur and result in detectable luminescence. On the other hand, if the biological conditions or biomolecules are not present, the protecting group moieties would remain on the bicyclic reactant, aminothiol derivative and/or luciferin derivative, and there would be no substantial detectable luminescence.

The reaction partners, bicyclic reactants and aminothiol derivatives, for the condensation reaction are discussed in more detail below. In the description, reference to formula with a Roman numeral, such as (I), is meant to include the formulae with the Roman numeral and letter, e.g. (Ia) and (Ib).

The disclosure then discusses protecting groups for the reaction partners, the condensation reaction and reaction products thereof, assays using the condensation reaction and luciferin-unmasking reaction, compositions comprising the disclosed compounds, and utility of the disclosed compounds.

Bicyclic Reactants

Formula I

The present disclosure provides bicyclic reactants and composition comprising the bicyclic reactants. In certain embodiments, the present disclosure provides cyanobenzothiazole (CBT) derivatives and composition comprising the CBT derivatives. Cyanobenzothiazole (CBT) has the following structure:

[Structure of cyanobenzothiazole: benzothiazole with CN]

The embodiments provide compounds of Formula Ia and composition comprising the compounds.

(Ia)

[Structure: $PG^{IV}-Q^1$-benzothiazole-CN-$PG^I$, with $R^1$ substituent]

wherein $Q^1$ is a heteroatom functional group selected from —O— and —$NR^{Q1}$—;

$R^{Q1}$ is selected from hydrogen, alkyl, and substituted alkyl;

$PG^{IV}$ is hydrogen or a protecting group for the heteroatom functional group;

$R^1$ is selected from hydrogen, halogen hydroxyl, alkyl, substituted alkyl, alkoxy, amino, and substituted amino; and $PG^I$ is an optional protecting group for cyano group.

The embodiments provide compounds of Formula Ib and composition comprising the compounds.

(Ib)

[Structure: $PG^{IV}-Q^1$-benzothiazole-CN-$PG^I$, with $R^1$ substituent at different position]

wherein $Q^1$ is a heteroatom functional group selected from —O— and —$NR^{Q1}$—;

$R^{Q1}$ is selected from hydrogen, alkyl, and substituted alkyl;

$PG^{IV}$ is hydrogen or a protecting group for the heteroatom functional group;

$R^1$ is selected from hydrogen, halogen hydroxyl, alkyl, substituted alkyl, alkoxy, amino, and substituted amino; and $PG^I$ is an optional protecting group for cyano group.

The embodiments provide compounds of Formula Ic and composition comprising the compounds.

(Ic)

[Structure: $PG^{IV}-Q^1$-benzothiazole-CN, with $R^1$ substituent]

wherein $Q^1$ is a heteroatom functional group selected from —O— and —$NR^{Q1}$—;

$R^{Q1}$ is selected from hydrogen, alkyl, and substituted alkyl;

$PG^{IV}$ is a protecting group for the heteroatom functional group; and $R^1$ is selected from hydrogen, halogen hydroxyl, alkyl, substituted alkyl, alkoxy, amino, and substituted amino.

The embodiments provide compounds of Formula Id and composition comprising the compounds.

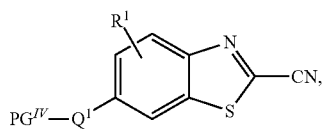

wherein $Q^1$ is a heteroatom functional group selected from —O— and —NR$^{Q1}$—;

R$^{Q1}$ is selected from hydrogen, alkyl, and substituted alkyl;

PG$^{IV}$ is a protecting group for the heteroatom functional group; and

R$^1$ is selected from hydrogen, halogen hydroxyl, alkyl, substituted alkyl, alkoxy, amino, and substituted amino.

In formula I, $Q^1$ is a heteroatom functional group selected from —O— and —NR$^{Q1}$—. In certain embodiments, $Q^1$ is —O—. In certain embodiments, $Q^1$ is —NR$^{Q1}$—. In formula I, when $Q^1$ is —NR$^{Q1}$—, R$^{Q1}$ is selected from hydrogen, alkyl, and substituted alkyl. In certain embodiments, R$^{Q1}$ is hydrogen. In certain embodiments, R$^{Q1}$ is alkyl. In certain embodiments, R$^{Q1}$ is substituted alkyl.

In formula I, PG$^{IV}$ is hydrogen or a protecting group for the heteroatom functional group. In certain embodiments, PG$^{IV}$ is hydrogen. In certain embodiments, PG$^{IV}$ is a protecting group for the heteroatom functional group.

In certain embodiments, PG$^{IV}$ is selected from hydrogen, alkyl, substituted alkyl, alkenyl, substituted alkenyl, alkynyl, substituted alkynyl, aryl, substituted aryl, acyl, aminoacyl, carboxyl ester, aminosulfonyl, sulfonyl, alkoxycarbonylamino, and aminocarbonylalkoxy.

In certain embodiments, PG$^{IV}$ is selected from hydrogen, alkyl, substituted alkyl, acyl, aminoacyl, and carboxyl ester. In certain embodiments, PG$^{IV}$ is hydrogen. In certain embodiments, PG$^{IV}$ is alkyl. In certain embodiments, PG$^{IV}$ is substituted alkyl. In certain embodiments, PG$^{IV}$ is acyl. In certain embodiments, PG$^{IV}$ is aminoacyl. In certain embodiments, PG$^{IV}$ is carboxyl ester. In certain embodiments, PG$^{IV}$ is alkoxycarbonylamino. In certain embodiments, PG$^{IV}$ is aminocarbonylalkoxy.

In formula I, $R^1$ is selected from hydrogen, halogen hydroxyl, alkyl, substituted alkyl, alkoxy, amino, and substituted amino.

In certain embodiments, $R^1$ is hydrogen. In certain embodiments, $R^1$ is halogen. In certain embodiments, $R^1$ is hydroxyl. In certain embodiments, $R^1$ is alkyl or substituted alkyl. In certain embodiments, $R^1$ is alkoxy. In certain embodiments, $R^1$ is amino or substituted amino.

In formula I, PG$^I$ is an optional protecting group for cyano group. In certain embodiments, PG$^I$ is not present. In certain embodiments, PG$^I$ is present.

In formula I, if PG$^I$ is present, there is a masked cyano group. A masked cyano group is a chemically protected form of a cyano group, in which the cyano group is in the form of a protected or protecting group (also known as a masked or masking group or a blocked or blocking group). In certain embodiments, PG$^I$ is present such that the masked cyano group is —C(O)NH$_2$, —C(O)NRR, and —C=NOH (aldoxime); wherein R is independently selected from hydrogen and alkyl.

In formula I, in certain embodiments, at least one of PG$^I$ and PG$^{IV}$ is a protecting group. In certain embodiments, PG$^I$ is a protecting group. In certain embodiments, PG$^{IV}$ is a protecting group.

In certain embodiments, the compound of formula I has the following formula:

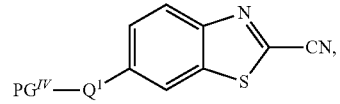

wherein

-Q$^1$-PG$^{IV}$ is selected from the following:

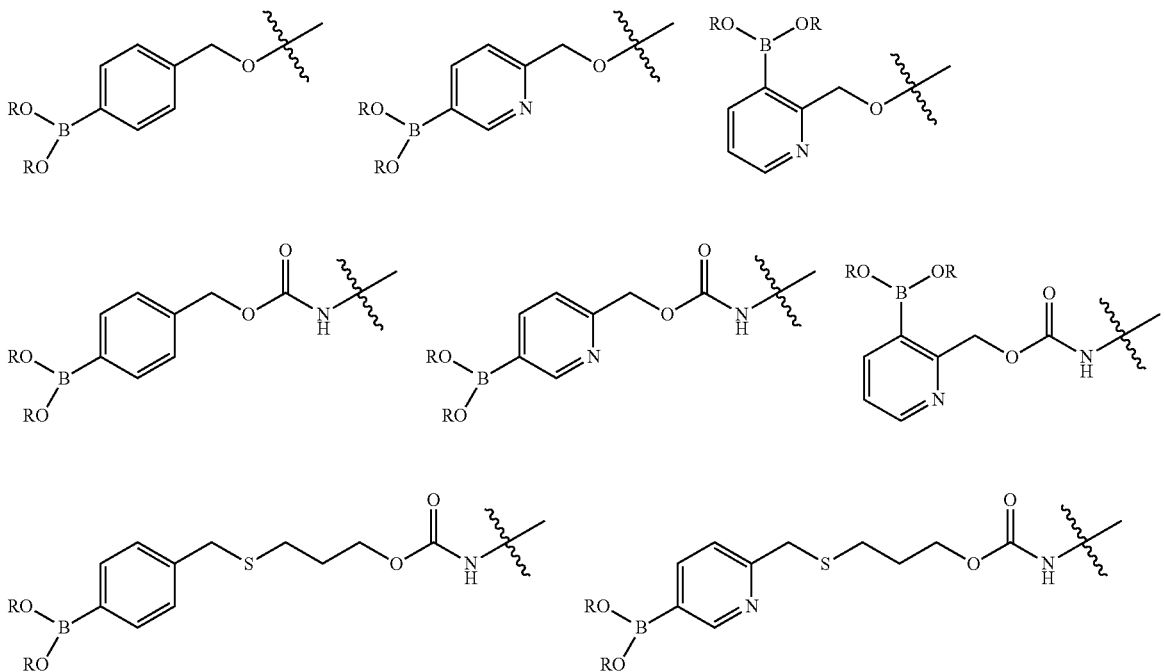

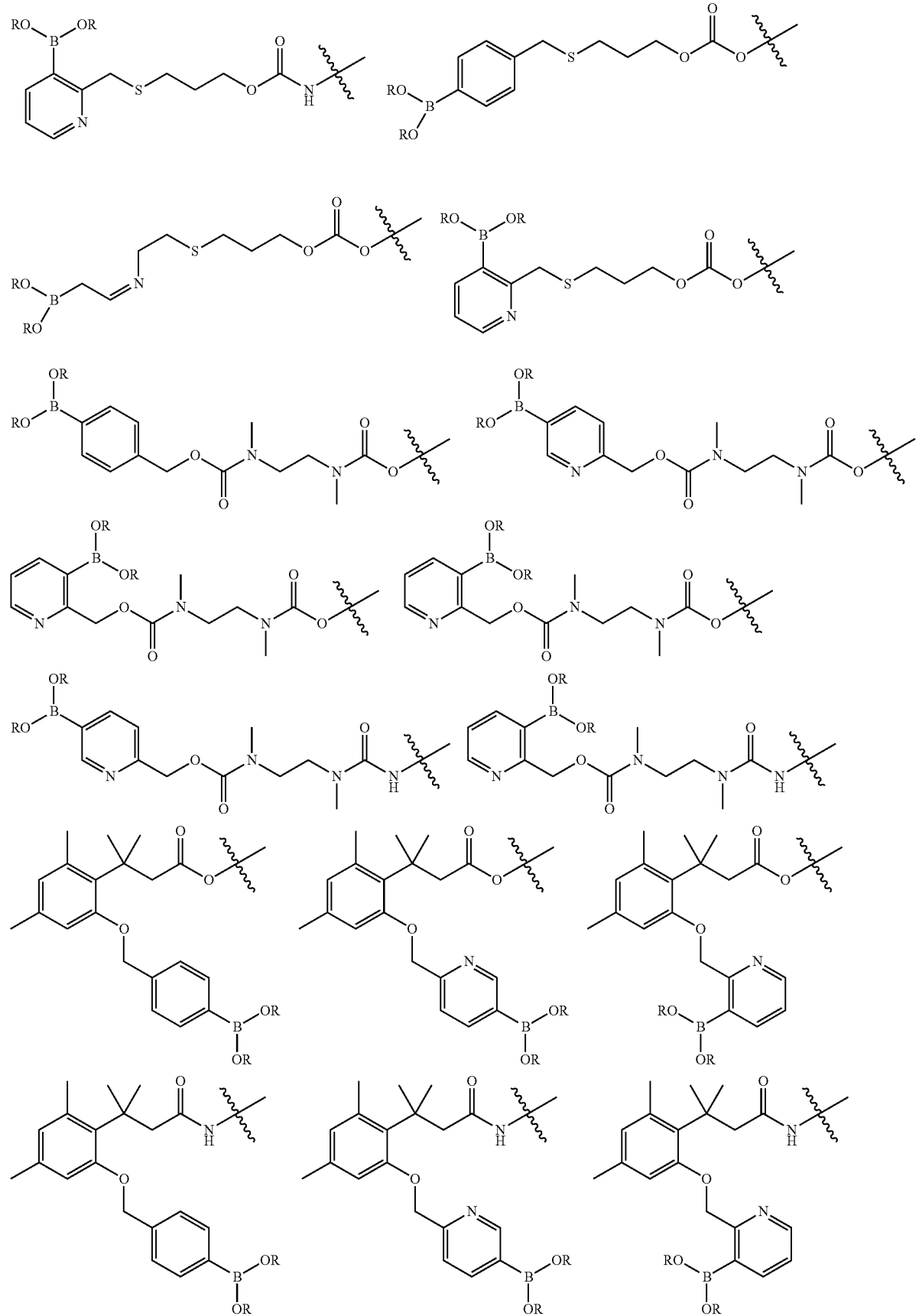

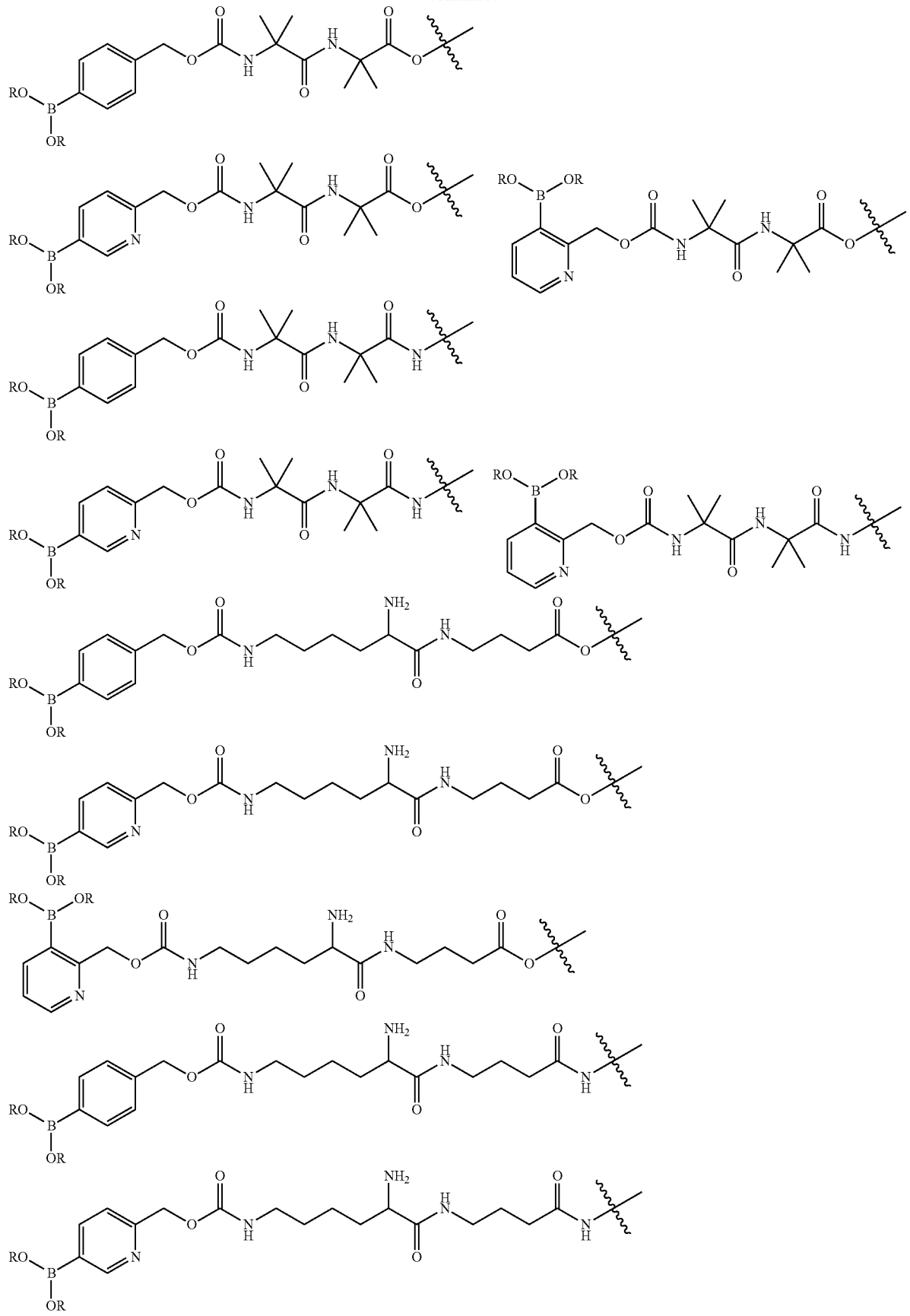

-continued
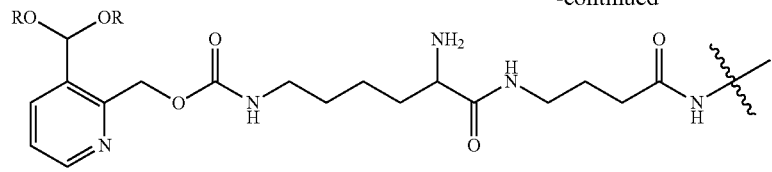
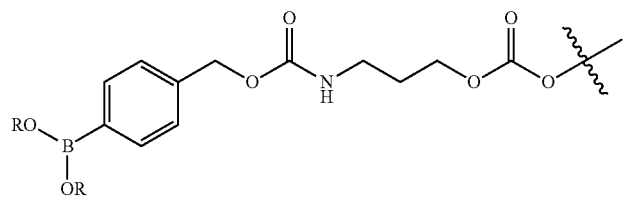
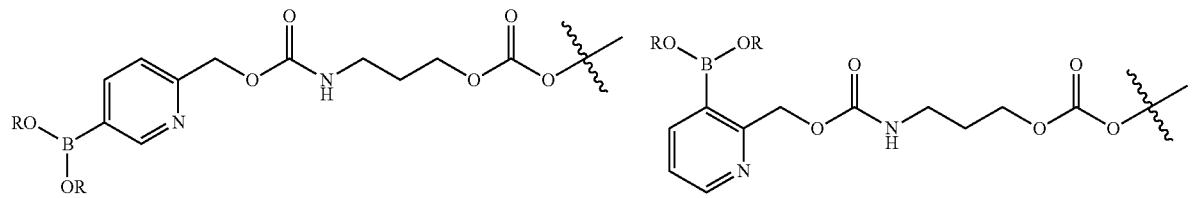
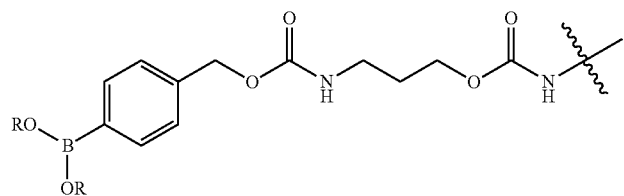
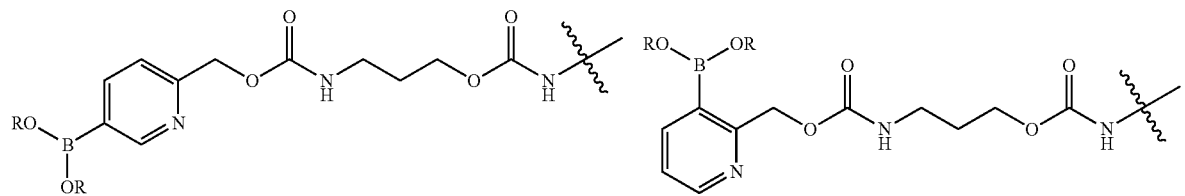
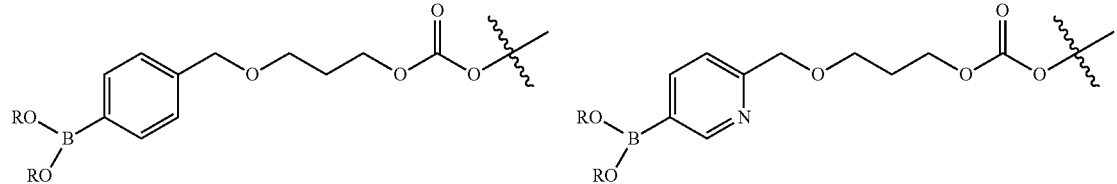
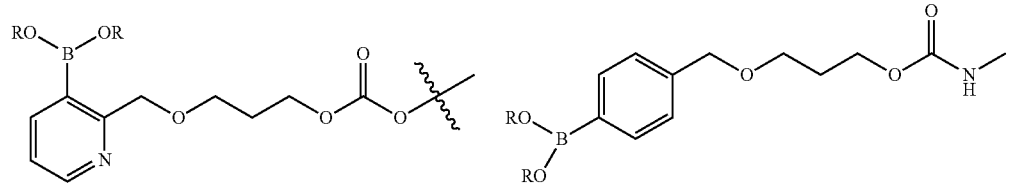
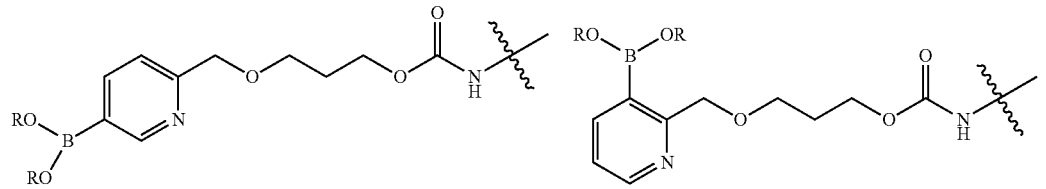
wherein R is hydrogen or alkyl.

In certain embodiments, R is selected from the following. Both the alkyl group and resulting boronic ester are shown below:

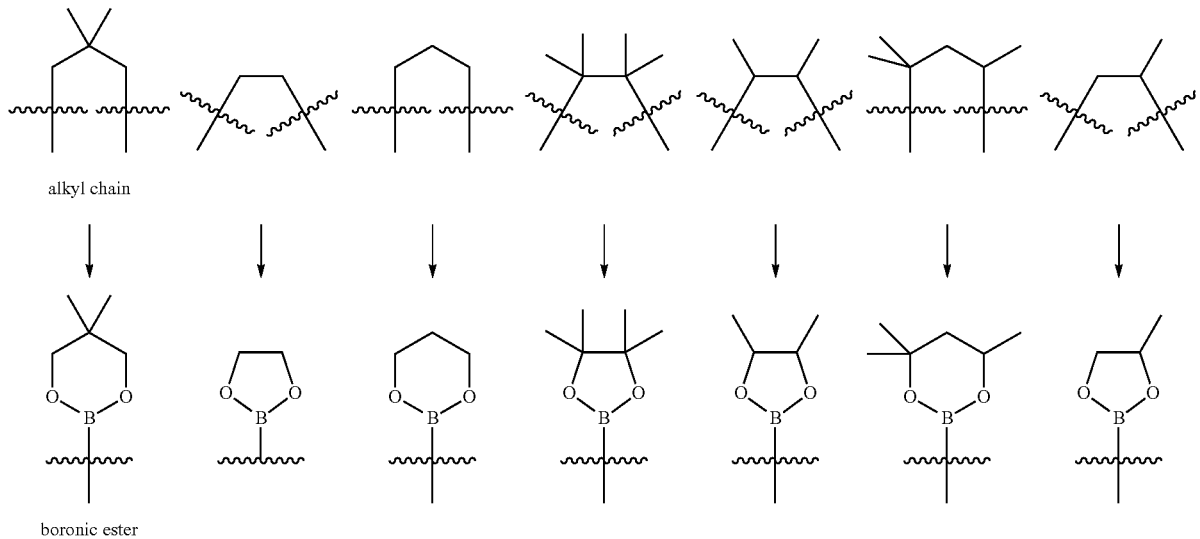

alkyl chain boronic ester

Formula II

The embodiments provide compounds of Formula IIa and composition comprising the compounds.

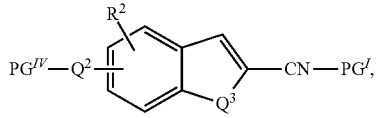

(IIa)

wherein $Q^2$ is a heteroatom functional group selected from —O— and —NR$^{Q2}$—;

$R^{Q2}$ is selected from hydrogen, alkyl, and substituted alkyl;

$PG^{IV}$ is hydrogen or a protecting group for the heteroatom functional group;

$R^2$ is selected from hydrogen, halogen hydroxyl, alkyl, substituted alkyl, alkoxy, amino, and substituted amino;

$Q^3$ is —O— or —S—; and $PG^I$ is an optional protecting group for cyano group.

The embodiments provide compounds of Formula IIb and composition comprising the compounds.

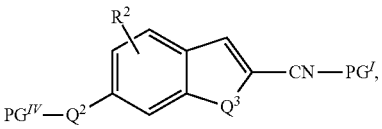

(IIb)

wherein $Q^2$ is a heteroatom functional group selected from —O— and —NR$^{Q2}$—;

$R^{Q2}$ is selected from hydrogen, alkyl, and substituted alkyl;

$PG^{IV}$ is hydrogen or a protecting group for the heteroatom functional group;

$R^2$ is selected from hydrogen, halogen hydroxyl, alkyl, substituted alkyl, alkoxy, amino, and substituted amino;

$Q^3$ is —O— or —S—; and $PG^I$ is an optional protecting group for cyano group.

In formula II, $Q^2$ is a heteroatom functional group selected from —O— and —NR$^{Q2}$—. In certain embodiments, $Q^2$ is —O—. In certain embodiments, $Q^2$ is —NR$^{Q2}$—. In formula I, when $Q^2$ is —NR$^{Q2}$—, $R^{Q2}$ is selected from hydrogen, alkyl, and substituted alkyl. In certain embodiments, $R^{Q2}$ is hydrogen. In certain embodiments, $R^{Q2}$ is alkyl. In certain embodiments, $R^{Q2}$ is substituted alkyl.

In formula II, $PG^{IV}$ is hydrogen or a protecting group for the heteroatom functional group. In certain embodiments, $PG^{IV}$ is hydrogen. In certain embodiments, $PG^{IV}$ is a protecting group for the heteroatom functional group.

In certain embodiments, $PG^{IV}$ is selected from hydrogen, alkyl, substituted alkyl, alkenyl, substituted alkenyl, alkynyl, substituted alkynyl, aryl, substituted aryl, acyl, aminoacyl, carboxyl ester, aminosulfonyl, sulfonyl, alkoxycarbonylamino, and aminocarbonylalkoxy.

In certain embodiments, $PG^{IV}$ is selected from hydrogen, alkyl, substituted alkyl, acyl, aminoacyl, and carboxyl ester. In certain embodiments, $PG^{IV}$ is hydrogen. In certain embodiments, $PG^{IV}$ is alkyl. In certain embodiments, $PG^{IV}$ is substituted alkyl. In certain embodiments, $PG^{IV}$ is acyl. In certain embodiments, $PG^{IV}$ is aminoacyl. In certain embodiments, $PG^{IV}$ is carboxyl ester. In certain embodiments, $PG^{IV}$ is alkoxycarbonylamino. In certain embodiments, $PG^{IV}$ is aminocarbonylalkoxy.

In formula II, $R^2$ is selected from hydrogen, halogen hydroxyl, alkyl, substituted alkyl, alkoxy, amino, and substituted amino.

In certain embodiments, $R^2$ is hydrogen. In certain embodiments, $R^2$ is halogen. In certain embodiments, $R^2$ is hydroxyl. In certain embodiments, $R^2$ is alkyl or substituted alkyl. In certain embodiments, $R^2$ is alkoxy. In certain embodiments, $R^2$ is amino or substituted amino.

In formula II, $Q^3$ is —O— or —S—. In certain embodiments, $Q^3$ is —O—. In certain embodiments, $Q^3$ is —S—.

In formula II, $PG^I$ is an optional protecting group for cyano group. In certain embodiments, $PG^I$ is not present. In certain embodiments, $PG^I$ is present.

In formula II, if $PG^I$ is present, there is a masked cyano group. A masked cyano group is a chemically protected form of a cyano group, in which the cyano group is in the form of a protected or protecting group (also known as a masked or masking group or a blocked or blocking group). In certain embodiments, $PG^I$ is present such that the masked cyano group is —C(O)NH$_2$, —C(O)NRR, and —C=NOH (aldoxime); wherein R is independently selected from hydrogen and alkyl.

In formula II, in certain embodiments, at least one of $PG^I$ and $PG^{IV}$ is a protecting group. In certain embodiments, $PG^I$ is a protecting group. In certain embodiments, $PG^{IV}$ is a protecting group.

Formula III

The embodiments provide compounds of Formula IIIa and composition comprising the compounds.

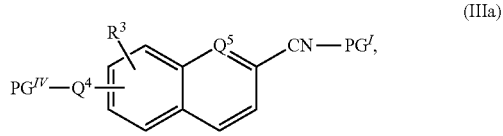

(IIIa)

wherein $Q^4$ is a heteroatom functional group selected from —O— and —NR$^{Q4}$—;

$R^{Q4}$ is selected from hydrogen, alkyl, and substituted alkyl;

$PG^{IV}$ is hydrogen or a protecting group for the heteroatom functional group;

$R^3$ is selected from hydrogen, halogen hydroxyl, alkyl, substituted alkyl, alkoxy, amino, and substituted amino;

$Q^5$ is —N— or —CH—; and $PG^I$ is an optional protecting group for cyano group.

The embodiments provide compounds of Formula IIIb and composition comprising the compounds.

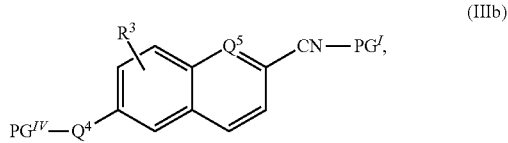

(IIIb)

wherein $Q^4$ is a heteroatom functional group selected from —O— and —NR$^{Q4}$—;

$R^{Q4}$ is selected from hydrogen, alkyl, and substituted alkyl;

$PG^{IV}$ is hydrogen or a protecting group for the heteroatom functional group; and $R^3$ is selected from hydrogen, halogen hydroxyl, alkyl, substituted alkyl, alkoxy, amino, and substituted amino;

$Q^5$ is —N— or —CH—; and $PG^I$ is an optional protecting group for cyano group.

In formula III, $Q^4$ is selected from —O— and —NR$^{Q4}$—. In certain embodiments, $Q^4$ is —O—. In certain embodiments, $Q^4$ is —NR$^{Q4}$—. In formula III, when $Q^4$ is —NR$^{Q4}$—, $R^{Q4}$ is selected from hydrogen, alkyl, and substituted alkyl. In certain embodiments, $R^{Q4}$ is hydrogen. In certain embodiments, $R^{Q4}$ is alkyl. In certain embodiments, $R^{Q4}$ is substituted alkyl.

In formula III, $PG^{IV}$ is hydrogen or a protecting group for the heteroatom functional group. In certain embodiments, $PG^{IV}$ is hydrogen. In certain embodiments, $PG^{IV}$ is a protecting group for the heteroatom functional group.

In certain embodiments, $PG^{IV}$ is selected from hydrogen, alkyl, substituted alkyl, alkenyl, substituted alkenyl, alkynyl, substituted alkynyl, aryl, substituted aryl, acyl, aminoacyl, carboxyl ester, aminosulfonyl, sulfonyl, alkoxycarbonylamino, and aminocarbonylalkoxy.

In certain embodiments, $PG^{IV}$ is selected from hydrogen, alkyl, substituted alkyl, acyl, aminoacyl, and carboxyl ester. In certain embodiments, $PG^{IV}$ is hydrogen. In certain embodiments, $PG^{IV}$ is alkyl. In certain embodiments, $PG^{IV}$ is substituted alkyl. In certain embodiments, $PG^{IV}$ is acyl. In certain embodiments, $PG^{IV}$ is aminoacyl. In certain embodiments, $PG^{IV}$ is carboxyl ester. In certain embodiments, $PG^{IV}$ is alkoxycarbonylamino. In certain embodiments, $PG^{IV}$ is aminocarbonylalkoxy.

In formula III, $R^3$ is selected from hydrogen, halogen hydroxyl, alkyl, substituted alkyl, alkoxy, amino, and substituted amino.

In certain embodiments, $R^3$ is hydrogen. In certain embodiments, $R^3$ is halogen. In certain embodiments, $R^3$ is hydroxyl. In certain embodiments, $R^3$ is alkyl or substituted alkyl. In certain embodiments, $R^3$ is alkoxy. In certain embodiments, $R^3$ is amino or substituted amino.

In formula III, $Q^5$ is —N— or —CH—. In certain embodiments, $Q^5$ is —N—. In certain embodiments, $Q^5$ is —CH—.

In formula III, $PG^I$ is an optional protecting group for cyano group. In certain embodiments, $PG^I$ is not present. In certain embodiments, $PG^I$ is present.

In formula III, if $PG^I$ is present, there is a masked cyano group. A masked cyano group is a chemically protected form of a cyano group, in which the cyano group is in the form of a protected or protecting group (also known as a masked or masking group or a blocked or blocking group). In certain embodiments, $PG^I$ is present such that the masked cyano group is —C(O)NH$_2$, —C(O)NRR, and —C=NOH (aldoxime); wherein R is independently selected from hydrogen and alkyl.

In formula III, in certain embodiments, at least one of $PG^I$ and $PG^{IV}$ is a protecting group. In certain embodiments, $PG^I$ is a protecting group. In certain embodiments, $PG^{IV}$ is a protecting group.

Formula IV

The embodiments provide compounds of Formula IVa and composition comprising the compounds.

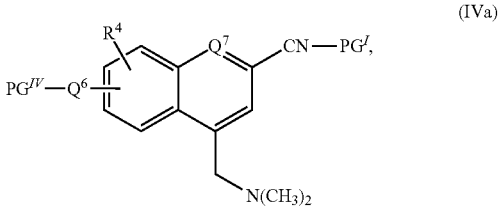

(IVa)

wherein $Q^6$ is a heteroatom functional group selected from —O— and —NR$^{Q6}$—;

$R^{Q6}$ is selected from hydrogen, alkyl, and substituted alkyl;

$PG^{IV}$ is hydrogen or a protecting group for the heteroatom functional group;

$R^4$ is selected from hydrogen, halogen hydroxyl, alkyl, substituted alkyl, alkoxy, amino, and substituted amino;

$Q^7$ is —N— or —CH—; and $PG^I$ is an optional protecting group for cyano group.

The embodiments provide compounds of Formula IVb and composition comprising the compounds.

(IVb)

$R^4$, $Q^7$, CN—PG$^I$, PG$^{IV}$—Q$^6$, N(CH$_3$)$_2$ wherein
Q$^6$ is a heteroatom functional group selected from —O— and —NR$^{Q6}$—;
R$^{Q6}$ is selected from hydrogen, alkyl, and substituted alkyl;
PG$^{IV}$ is hydrogen or a protecting group for the heteroatom functional group;
R$^4$ is selected from hydrogen, halogen hydroxyl, alkyl, substituted alkyl, alkoxy, amino, and substituted amino;
Q$^7$ is —N— or —CH—; and
PG$^I$ is an optional protecting group for cyano group.

In formula IV, Q$^6$ is selected from —O— and —NR$^{Q6}$—. In certain embodiments, Q$^6$ is —O—. In certain embodiments, Q$^6$ is —NR$^{Q6}$—. In formula IV, when Q$^6$ is —NR$^{Q6}$—, R$^{Q6}$ is selected from hydrogen, alkyl, and substituted alkyl. In certain embodiments, R$^{Q6}$ is hydrogen. In certain embodiments, R$^{Q6}$ is alkyl. In certain embodiments, R$^{Q6}$ is substituted alkyl.

In formula IV, PG$^{IV}$ is hydrogen or a protecting group for the heteroatom functional group. In certain embodiments, PG$^{IV}$ is hydrogen. In certain embodiments, PG$^{IV}$ is a protecting group for the heteroatom functional group.

In certain embodiments, PG$^{IV}$ is selected from hydrogen, alkyl, substituted alkyl, alkenyl, substituted alkenyl, alkynyl, substituted alkynyl, aryl, substituted aryl, acyl, aminoacyl, carboxyl ester, aminosulfonyl, sulfonyl, alkoxycarbonylamino, and aminocarbonylalkoxy.

In certain embodiments, PG$^{IV}$ is selected from hydrogen, alkyl, substituted alkyl, acyl, aminoacyl, and carboxyl ester. In certain embodiments, PG$^{IV}$ is hydrogen. In certain embodiments, PG$^{IV}$ is alkyl. In certain embodiments, PG$^{IV}$ is substituted alkyl. In certain embodiments, PG$^{IV}$ is acyl. In certain embodiments, PG$^{IV}$ is aminoacyl. In certain embodiments, PG$^{IV}$ is carboxyl ester. In certain embodiments, PG$^{IV}$ is alkoxycarbonylamino. In certain embodiments, PG$^{IV}$ is aminocarbonylalkoxy.

In formula IV, R$^4$ is selected from hydrogen, halogen hydroxyl, alkyl, substituted alkyl, alkoxy, amino, and substituted amino.

In certain embodiments, R$^4$ is hydrogen. In certain embodiments, R$^4$ is halogen. In certain embodiments, R$^4$ is hydroxyl. In certain embodiments, R$^4$ is alkyl or substituted alkyl. In certain embodiments, R$^4$ is alkoxy. In certain embodiments, R$^4$ is amino or substituted amino.

In formula IV, Q$^7$ is —N— or —CH—. In certain embodiments, Q$^7$ is —N—. In certain embodiments, Q$^7$ is —CH—.

In formula IV, PG$^I$ is an optional protecting group for cyano group. In certain embodiments, PG$^I$ is not present. In certain embodiments, PG$^I$ is present.

In formula IV, if PG$^I$ is present, there is a masked cyano group. A masked cyano group is a chemically protected form of a cyano group, in which the cyano group is in the form of a protected or protecting group (also known as a masked or masking group or a blocked or blocking group). In certain embodiments, PG$^I$ is present such that the masked cyano group is —C(O)NH$_2$, —C(O)NRR, and —C=NOH (aldoxime); wherein R is independently selected from hydrogen and alkyl.

In formula IV, in certain embodiments, at least one of PG$^I$ and PG$^{IV}$ is a protecting group. In certain embodiments, PG$^I$ is a protecting group. In certain embodiments, PG$^{IV}$ is a protecting group.

Formula V

The embodiments provide compounds of Formula Va and composition comprising the compounds.

(Va)

$R^5$, $Q^9$, CN—PG$^I$, PG$^{IV}$—Q$^8$ wherein
Q$^8$ is a heteroatom functional group selected from —O— and —NR$^{Q8}$—;
R$^{Q8}$ is selected from hydrogen, alkyl, and substituted alkyl;
PG$^{IV}$ is hydrogen or a protecting group for the heteroatom functional group;
R$^5$ is selected from hydrogen, halogen hydroxyl, alkyl, substituted alkyl, alkoxy, amino, and substituted amino;
Q$^9$ is —N— or —CH—; and
PG$^1$ is an optional protecting group for cyano group.

The embodiments provide compounds of Formula Vb and composition comprising the compounds.

(Vb)

$R^5$, $Q^9$, CN—PG$^I$, PG$^{IV}$—Q$^8$ wherein
Q$^8$ is a heteroatom functional group selected from —O— and —NR$^{Q8}$—;
R$^{Q8}$ is selected from hydrogen, alkyl, and substituted alkyl;
PG$^{IV}$ is hydrogen or a protecting group for the heteroatom functional group;
R$^5$ is selected from hydrogen, halogen hydroxyl, alkyl, substituted alkyl, alkoxy, amino, and substituted amino;
Q$^9$ is —N— or —CH—; and
PG$^1$ is an optional protecting group for cyano group.

In formula V, Q$^8$ is selected from —O— and —NR$^{Q8}$—. In certain embodiments, Q$^8$ is —O—. In certain embodiments, Q$^8$ is —NR$^{Q8}$—. In formula V, when Q$^8$ is —NR$^{Q8}$—, R$^{Q8}$ is selected from hydrogen, alkyl, and substituted alkyl. In certain embodiments, R$^{Q8}$ is hydrogen. In certain embodiments, R$^{Q8}$ is alkyl. In certain embodiments, R$^{Q8}$ is substituted alkyl.

In formula V, PG$^{IV}$ is hydrogen or a protecting group for the heteroatom functional group. In certain embodiments, PG$^{IV}$ is hydrogen. In certain embodiments, PG$^{IV}$ is a protecting group for the heteroatom functional group.

In certain embodiments, PG$^{IV}$ is selected from hydrogen, alkyl, substituted alkyl, alkenyl, substituted alkenyl, alkynyl, substituted alkynyl, aryl, substituted aryl, acyl, aminoacyl, carboxyl ester, aminosulfonyl, sulfonyl, alkoxycarbonylamino, and aminocarbonylalkoxy.

In certain embodiments, $PG^{IV}$ is selected from hydrogen, alkyl, substituted alkyl, acyl, aminoacyl, and carboxyl ester. In certain embodiments, $PG^{IV}$ is hydrogen. In certain embodiments, $PG^{IV}$ is alkyl. In certain embodiments, $PG^{IV}$ is substituted alkyl. In certain embodiments, $PG^{IV}$ is acyl. In certain embodiments, $PG^{IV}$ is aminoacyl. In certain embodiments, $PG^{IV}$ is carboxyl ester. In certain embodiments, $PG^{IV}$ is alkoxycarbonylamino. In certain embodiments, $PG^{IV}$ is aminocarbonylalkoxy.

In formula V, $R^5$ is selected from hydrogen, halogen hydroxyl, alkyl, substituted alkyl, alkoxy, amino, and substituted amino.

In certain embodiments, $R^5$ is hydrogen. In certain embodiments, $R^5$ is halogen. In certain embodiments, $R^5$ is hydroxyl. In certain embodiments, $R^5$ is alkyl or substituted alkyl. In certain embodiments, $R^5$ is alkoxy. In certain embodiments, $R^5$ is amino or substituted amino.

In formula V, $Q^9$ is —N— or —CH—. In certain embodiments, $Q^9$ is —N—. In certain embodiments, $Q^9$ is —CH—.

In formula V, $PG^I$ is an optional protecting group for cyano group. In certain embodiments, $PG^I$ is not present. In certain embodiments, $PG^I$ is present.

In formula V, if $PG^I$ is present, there is a masked cyano group. A masked cyano group is a chemically protected form of a cyano group, in which the cyano group is in the form of a protected or protecting group (also known as a masked or masking group or a blocked or blocking group). In certain embodiments, $PG^I$ is present such that the masked cyano group is —C(O)NH$_2$, —C(O)NRR, and —C═NOH (aldoxime); wherein R is independently selected from hydrogen and alkyl.

In formula V, in certain embodiments, at least one of $PG^I$ and $PG^{IV}$ is a protecting group. In certain embodiments, $PG^I$ is a protecting group. In certain embodiments, $PG^{IV}$ is a protecting group.

Aminothiol Derivatives

Aminothiol is a compound that comprises both an amino group and a thiol group.

In certain embodiments, as used herein, aminothiol is 2-aminoethanethiol, as shown below:

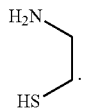

The term "derivative" refers, for example, to compounds that are derived from another compound and maintain the same general structure as the compound from, which they are derived.

The embodiments provide aminothiol derivatives and composition comprising the compounds. A subject aminothiol derivative is compound of formula:

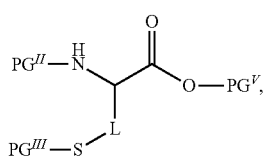

(VIa)

wherein $PG^{II}$ is hydrogen or a protecting group for an amino group;

$PG^{III}$ is hydrogen or a protecting group for a thiol group;

$PG^V$ is hydrogen or a protecting group for a carboxyl group; and

L is $C_{1-2}$ alkylene, $C_{1-2}$ alkenylene, or $C_{1-2}$ alkynylene.

The embodiments provide aminothiol derivatives and composition comprising the compounds. A subject aminothiol derivative is compound of formula:

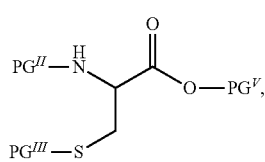

(VIb)

wherein $PG^{II}$ is hydrogen or a protecting group for an amino group;

$PG^{III}$ is hydrogen or a protecting group for a thiol group;

$PG^V$ is hydrogen or a protecting group for a carboxyl group; and wherein at least one of $PG^{II}$, $PG^{III}$, and $PG^V$ is a protecting group.

The embodiments provide aminothiol derivatives and composition comprising the compounds. A subject aminothiol derivative is compound of formula:

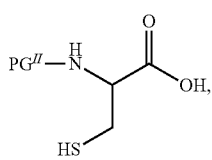

(VIc)

wherein $PG^{II}$ is a protecting group for an amino group.

The embodiments provide aminothiol derivatives and composition comprising the compounds. A subject aminothiol derivative is compound of formula:

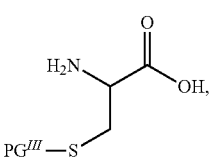

(VId)

wherein $PG^{III}$ is a protecting group for a thiol group.

The embodiments provide aminothiol derivatives and composition comprising the compounds. A subject aminothiol derivative is compound of formula:

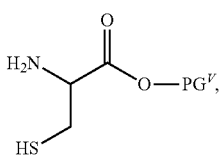

(VIe)

wherein $PG^V$ is a protecting group for a carboxyl group.

In formula VI, in certain embodiments, at least one of $PG^{II}$, $PG^{III}$, and $PG^V$ is a protecting group.

In formula VI, L is $C_{1-2}$ alkylene, $C_{1-2}$ alkenylene, or $C_{1-2}$ alkynylene. In certain embodiments, L is $C_{1-2}$ alkylene. In certain embodiments, L is $C_{1-2}$ alkenylene. In certain embodiments, L is $C_{1-2}$ alkynylene.

In formula VI, $PG^{II}$ is hydrogen or a protecting group for an amino group.

In certain embodiments, $PG^{II}$ is hydrogen.

In certain embodiments, $PG^{II}$ is a protecting group for an amino group. In formula VI, if $PG^{II}$ is present, there is a masked amino group. A masked amino group is a chemically protected form of an amino group, in which the amino group is in the form of a protected or protecting group (also known as a masked or masking group or a blocked or blocking group). Examples of masked amino groups can be found in Protective Groups in Organic Synthesis (T. Green and P. Wuts; 3rd Edition; John Wiley and Sons, 1999, for example at pages 494-659). In certain embodiments, a masked amino group is a carbamate or an amide.

In certain embodiments, $PG^{II}$ is present to form a masked amino group, wherein the amino group is connected to an amino acid, peptide, or protein. In certain embodiments, the amino acid, amino acid, peptide, or protein can be cleaved due to specific conditions.

In certain embodiments, $PG^{II}$ is selected from hydrogen, alkyl, substituted alkyl, alkenyl, substituted alkenyl, alkynyl, substituted alkynyl, alkoxy, substituted alkoxy, aryl, substituted aryl, acyl, aminoacyl, aminosulfonyl, and sulfonyl. In certain embodiments, $PG^{II}$ is hydrogen or alkyl. In certain embodiments, $PG^{II}$ is hydrogen. In certain embodiments, $PG^{II}$ is alkyl. In certain embodiments, $PG^{II}$ is acyl.

In formula VI, $PG^{III}$ is hydrogen or a protecting group for a thiol group.

In certain embodiments, $PG^{III}$ is hydrogen.

In certain embodiments, $PG^{III}$ is a protecting group for a thiol group. In formula VI, if $PG^{III}$ is present, there is a masked thiol group. A masked thiol group is a chemically protected form of a thiol group, in which the thiol group is in the form of a protected or protecting group (also known as a masked or masking group or a blocked or blocking group). Examples of masked thiol groups can be found in Protective Groups in Organic Synthesis (T. Green and P. Wuts; 3rd Edition; John Wiley and Sons, 1999, for example at pages 454-493). In certain embodiments, a masked thiol group is a thioether or thioester.

In certain embodiments, $PG^{III}$ is hydrogen, alkyl, substituted alkyl, alkenyl, substituted alkenyl, alkynyl, substituted alkynyl, alkoxy, substituted alkoxy, aryl, substituted aryl, acyl, aminoacyl, aminosulfonyl, or sulfonyl. In certain embodiments, $PG^{III}$ is hydrogen or alkyl. In certain embodiments, $PG^{III}$ is hydrogen. In certain embodiments, $PG^{III}$ is alkyl. In certain embodiments, $PG^{III}$ is acyl.

In formula VI, $PG^V$ is hydrogen or a protecting group for a carboxyl group.

In certain embodiments, $PG^V$ is hydrogen.

In certain embodiments, $PG^V$ is a protecting group for a carboxyl group. In formula VI, if $PG^V$ is present, there is a masked carboxyl group. A masked carboxyl group is a chemically protected form of a carboxyl group, in which the carboxyl group is in the form of a protected or protecting group (also known as a masked or masking group or a blocked or blocking group). Examples of masked carboxyl groups can be found in Protective Groups in Organic Synthesis (T. Green and P. Wuts; 3rd Edition; John Wiley and Sons, 1999, for example at pages 369-463). In certain embodiments, a masked carboxyl group is an ester, an amide, or a hydrazide.

In certain embodiments, $PG^V$ is selected from hydrogen, alkyl, substituted alkyl, alkenyl, substituted alkenyl, alkynyl, substituted alkynyl, alkoxy, substituted alkoxy, aryl, substituted aryl, acyl, aminoacyl, aminosulfonyl, and sulfonyl. In certain embodiments, $PG^V$ is hydrogen or alkyl. In certain embodiments, $PG^V$ is hydrogen. In certain embodiments, $PG^V$ is alkyl.

Protecting Groups for Bicyclic Reactants and Aminothiol Derivatives

The present disclosure provide for a bicyclic reactant and an aminothiol derivative, wherein each of these compounds can comprise protecting groups for various functional groups on the bicyclic reactant and amino derivative.

As discussed above, the bicyclic reactant can comprise protecting groups for the heteroatom functional group and/or cyano group. The aminothiol derivative can comprise protecting groups for the amino group, thiol group, and/or carboxyl group.

Examples of protecting groups for each of the heteroatom functional group, cyano group, amino group, thiol group, and carboxyl group can be found in Protective Groups in Organic Synthesis (T. Green and P. Wuts; 3rd Edition; John Wiley and Sons, 1999), which is hereby incorporated by reference in its entirety.

In certain embodiments, the protecting group for amino group or hydroxyl group on the bicyclic reactant can be a cleavable linker group that provides for release of the bicyclic moiety upon reaction.

Examples of protecting groups and cleavable linkers, including conditions for their deprotection, are discussed more detail below in section titled "Assays using condensation reaction and luciferin-unmasking reaction."

Condensation Reaction and Reaction Products Thereof

The present disclosure features a condensation reaction that can be carried out under physiological conditions or ex vivo prior to addition to cells or animal. In general, the condensation reaction involves reacting a bicyclic reactant with an aminothiol derivative, generating a luciferin or luciferin derivative. The term "luciferin" is used generically to refer to any light-emitting molecule utilized by a luciferase. A luciferin can provide detectable luminescence. A luciferin derivative can be unmasked to provide detectable luminescence in a luciferin-unmasking reaction.

The condensation reaction proceeds with reaction of an unprotected cyano group of a bicyclic reactant and an unprotected amino group and an unprotected thiol group of an aminothiol derivative. If any of the cyano, amino, or thiol groups is protected, the condensation reaction will not likely proceed. Thus, the condensation reaction can be controlled by addition and removal of protecting groups on any of the cyano, amino, or thiol groups.

In a certain embodiment, a condensation reaction is shown with a bicyclic reactant that is a compound of Formula Ia (unprotected form) and a compound of Formula VIa (unprotected form) to form a compound of Formula VIIa.

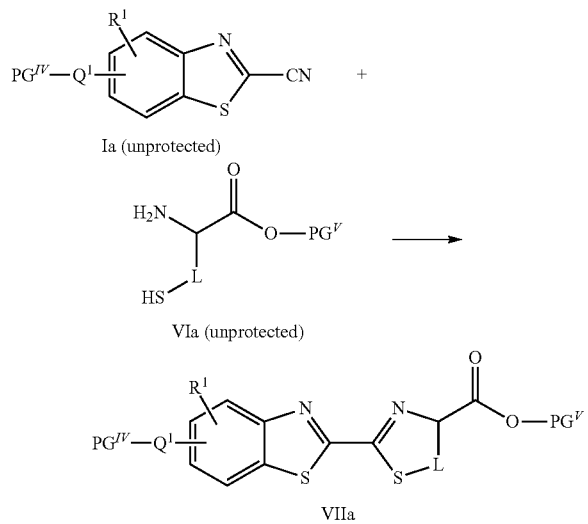

Ia (unprotected)

VIa (unprotected)

VIIa

The embodiments provide luciferin derivatives and composition comprising the compounds. A subject luciferin derivative is compound of formula:

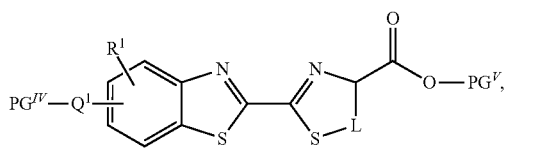

(VIIa)

wherein $Q^1$ is a heteroatom functional group selected from —O— and —NR$^{Q1}$—;

R$^{Q1}$ is selected from hydrogen, alkyl, and substituted alkyl;

PG$^{IV}$ is hydrogen or a protecting group for the heteroatom functional group;

$R^1$ is selected from hydrogen, halogen, hydroxyl, alkyl, substituted alkyl, alkoxy, amino, and substituted amino;

PG$^V$ is hydrogen or a protecting group for a carboxyl group; and

L is C$_{1-2}$, alkylene, C$_{1-2}$, alkenylene, or C$_{1-2}$, alkynylene.

In a certain embodiment, a condensation reaction is shown with a bicyclic portion that is a compound of Formula IIa (unprotected form) and a compound of Formula VIa (unprotected form) to form a compound of Formula VIIIa.

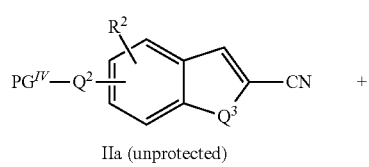

IIa (unprotected)

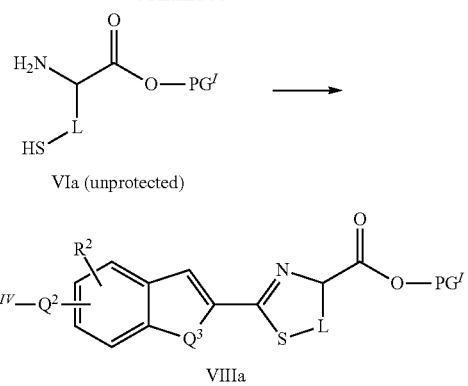

VIa (unprotected)

VIIIa

The embodiments provide luciferin derivatives and composition comprising the compounds. A subject luciferin derivative is compound of formula:

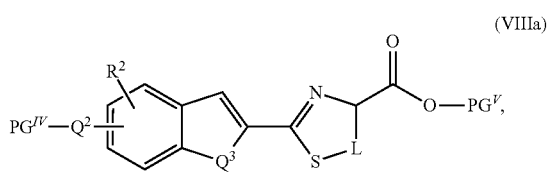

(VIIIa)

wherein $Q^2$ is a heteroatom functional group selected from —O— and —NR$^{Q2}$—;

R$^{Q2}$ is selected from hydrogen, alkyl, and substituted alkyl;

PG$^{IV}$ is hydrogen or a protecting group for the heteroatom functional group;

$R^2$ is selected from hydrogen, halogen hydroxyl, alkyl, substituted alkyl, alkoxy, amino, and substituted amino;

$Q^3$ is —O— or —S—;

PG$^V$ is hydrogen or a protecting group for a carboxyl group; and

L is C$_{1-2}$ alkylene, C$_{1-2}$ alkenylene, or C$_{1-2}$ alkynylene.

In a certain embodiment, a condensation reaction is shown with a bicyclic portion that is a compound of Formula Ma (unprotected form) and a compound of Formula VIa (unprotected form) to form a compound of Formula IXa.

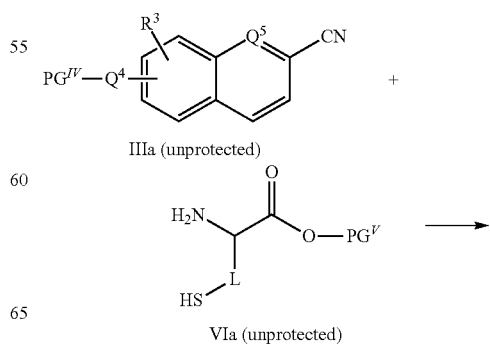

IIIa (unprotected)

VIa (unprotected)

-continued

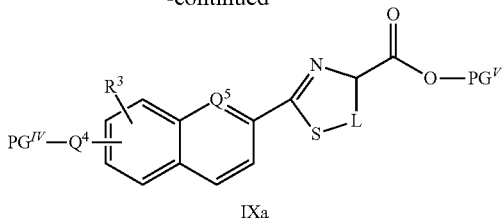

IXa

The embodiments provide luciferin derivatives and composition comprising the compounds. A subject luciferin derivative is compound of formula:

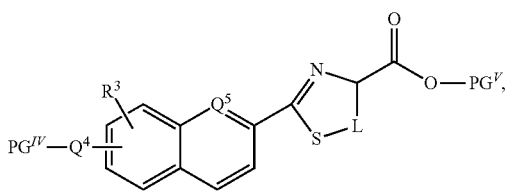

(IXa)

wherein $Q^4$ is a heteroatom functional group selected from —O— and —NR$^{Q4}$—;

R$^{Q4}$ is selected from hydrogen, alkyl, and substituted alkyl;

PG$^{IV}$ is hydrogen or a protecting group for the heteroatom functional group;

$R^3$ is selected from hydrogen, halogen hydroxyl, alkyl, substituted alkyl, alkoxy, amino, substituted amino, a moiety that comprises a reactive group that facilitates covalent attachment of a molecule of interest; and a molecule of interest;

$Q^5$ is —N— or —CH—;

PG$^V$ is hydrogen or a protecting group for a carboxyl group; and

L is $C_{1-2}$ alkylene, $C_{1-2}$ alkenylene, or $C_{1-2}$ alkynylene.

In a certain embodiment, a condensation reaction is shown with a bicyclic portion that is a compound of Formula IVa (unprotected form) and a compound of Formula VIa (unprotected form) to form a compound of Formula Xa.

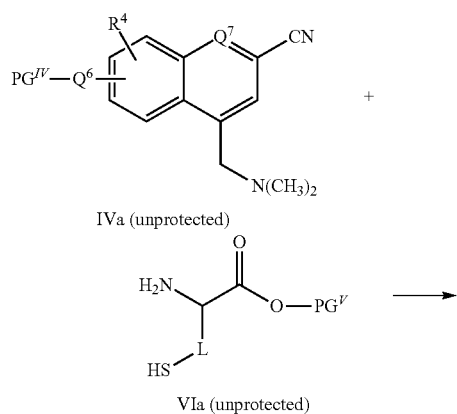

IVa (unprotected)

VIa (unprotected)

-continued

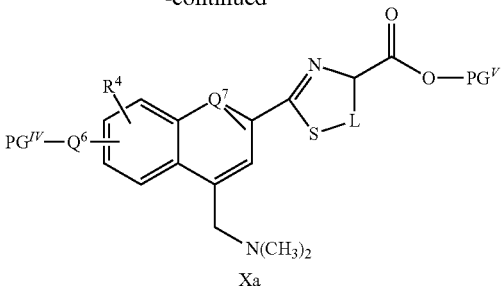

Xa

The embodiments provide luciferin derivatives and composition comprising the compounds. A subject luciferin derivative is compound of formula:

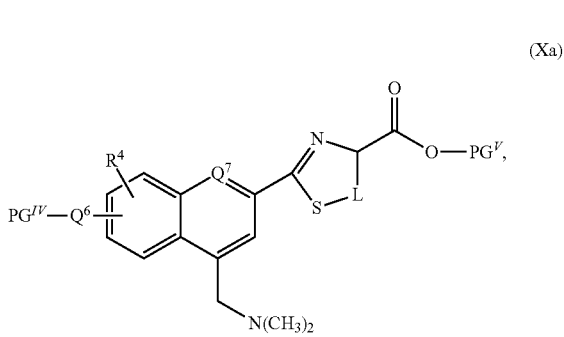

(Xa)

wherein $Q^6$ is a heteroatom functional group selected from —O— and —NR$^{Q6}$—;

R$^{Q6}$ is selected from hydrogen, alkyl, and substituted alkyl;

PG$^{IV}$ is hydrogen or a protecting group for the heteroatom functional group;

$R^4$ is selected from hydrogen, halogen hydroxyl, alkyl, substituted alkyl, alkoxy, amino, and substituted amino;

$Q^7$ is —N— or —CH—;

PG$^V$ is hydrogen or a protecting group for a carboxyl group; and

L is $C_{1-2}$ alkylene, $C_{1-2}$ alkenylene, or $C_{1-2}$ alkynylene.

In a certain embodiment, a condensation reaction is shown with a bicyclic portion that is a compound of Formula Va (unprotected form) and a compound of Formula VIa (unprotected form) to form a compound of Formula XIa.

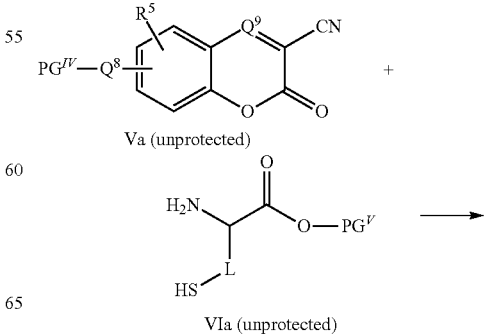

Va (unprotected)

VIa (unprotected)

-continued

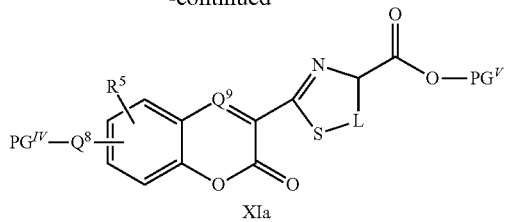

XIa

The embodiments provide luciferin derivatives and composition comprising the compounds. A subject luciferin derivative is compound of formula:

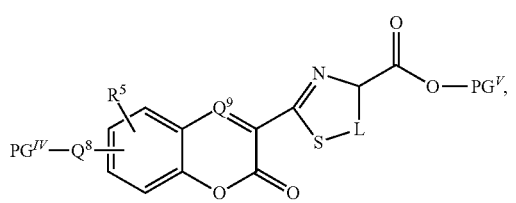

(XIa)

wherein
$Q^8$ is a heteroatom functional group selected from —O— and —NR$^{Q8}$—;
$R^{Q8}$ is selected from hydrogen, alkyl, and substituted alkyl;
$PG^{IV}$ is hydrogen or a protecting group for the heteroatom functional group;
$R^5$ is selected from hydrogen, halogen hydroxyl, alkyl, substituted alkyl, alkoxy, amino, and substituted amino;
$Q^9$ is —N— or —CH—;
$PG^V$ is hydrogen or a protecting group for a carboxyl group; and
L is $C_{1-2}$ alkylene, $C_{1-2}$ alkenylene, or $C_{1-2}$ alkynylene.

Assays Using Condensation Reaction and Luciferin-Unmasking Reaction

In general, the condensation reaction involves reacting a bicyclic reactant (in protected or deprotected version) with an aminothiol derivative (in protected or deprotected version), generating a luciferin or luciferin derivative. A luciferin can provide detectable luminescence. A luciferin derivative can be unmasked to provide detectable luminescence in a luciferin-unmasking reaction.

As discussed above, in certain embodiments, the bicyclic reactants and aminothiol derivatives can comprise protecting group moieties involved in detection of one or more biological processes or biomolecules. For example, deprotection or release of protecting group moieties on a bicyclic reactant and an aminothiol derivative can allow a condensation reaction to proceed to produce a luciferin or luciferin derivative. Luciferin can provide detectable luminescence.

If a luciferin derivative is formed from the condensation reaction, the luciferin derivative comprises a protecting group moiety in manner such that the luciferin derivative does not provide detectable luminescence. Upon deprotection or release of the protecting group moiety from the luciferin derivative in a luciferin-unmasking reaction, a luciferin is formed and can provide detectable luminescence.

An example of condensation and luciferin-unmasking reactions is shown below.

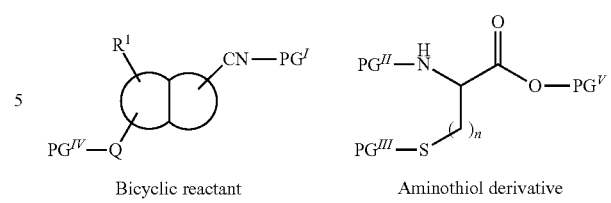

Bicyclic reactant         Aminothiol derivative

Deprotection of cyano     Deprotection of amino and thiol

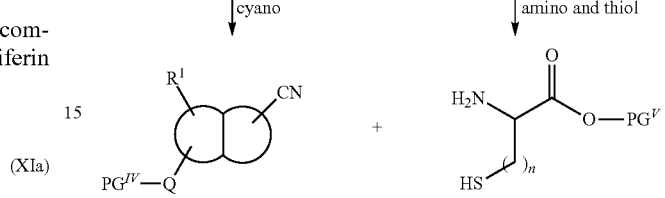

Condensation reaction

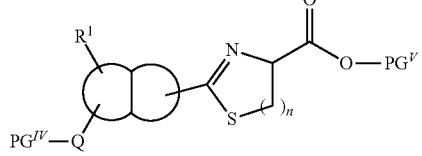

Luciferin derivative

Luciferin-unmasking reaction

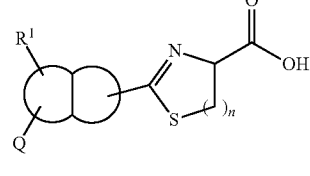

(luminescent)

In certain embodiments, the deprotection or release of the protecting group moiety in the luciferin-unmasking reaction can occur before the condensation reaction. The protecting groups for heteroatom functional group or carboxyl substituents of the reactants are deprotected before deprotection or release of protecting group moieties for the condensation reaction. Thus, upon occurrence of the condensation reaction, a luciferin is generated. An example of luciferin-unmasking and condensation reactions is shown below.

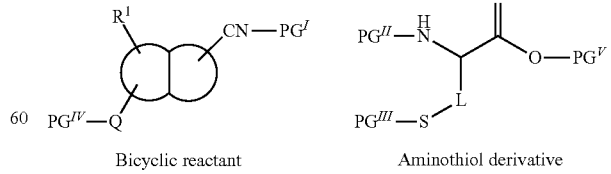

Bicyclic reactant         Aminothiol derivative

Deprotection of groups for luciferin-unmasking reaction

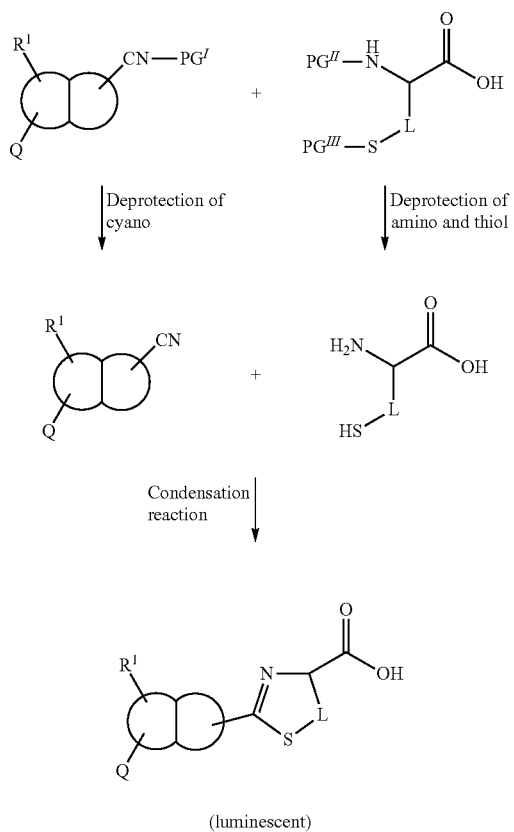

(luminescent)

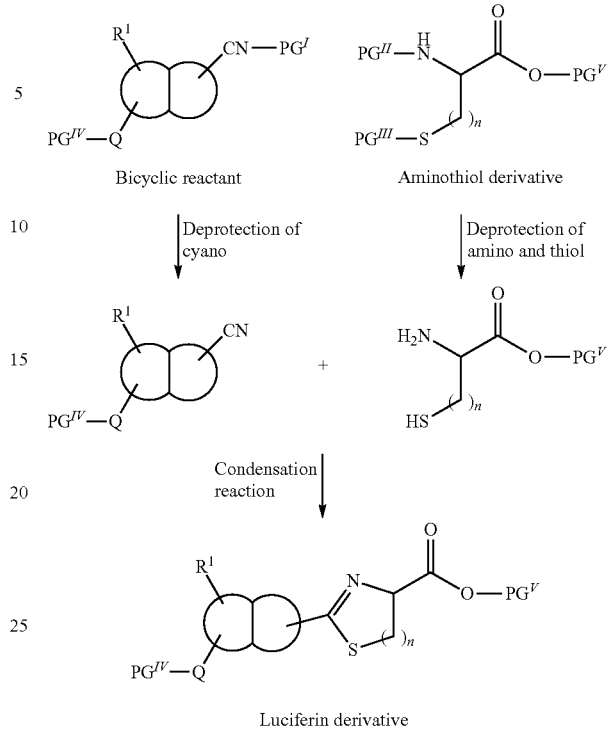

Bicyclic reactant · Aminothiol derivative

Luciferin derivative

The condensation reaction and luciferin-unmasking reaction can serve as an assay for the detection of one or more biological processes or biomolecules. Luminescence can be detected if luciferin is formed from the condensation and luciferin-unmasking reactions. The condensation and luciferin-unmasking reactions are dependent on the deprotection and release of protecting group moieties. Thus, under certain biological conditions or in the presence of certain biomolecules, the protecting group moieties are deprotected or released and the condensation and/or luciferin-unmasking reaction can occur and result in detectable luminescence. On the other hand, if the biological conditions or biomolecules are not present, the protecting group moieties would remain on the bicyclic reactant, aminothiol derivative and/or luciferin derivative, and there would be no substantial detectable luminescence.

Condensation Reaction

As discussed above, the condensation reaction proceeds with reaction of an unprotected cyano group of a bicyclic reactant and an unprotected amino group and an unprotected thiol group of an aminothiol derivative. If any of the cyano, amino, or thiol groups is protected, the condensation reaction will not likely proceed. Thus, the condensation reaction can be controlled by addition and removal of protecting groups on any of the cyano, amino, or thiol groups. An example of the condensation reaction is shown below.

For the bicyclic reactant, the compound can comprise a cyano group or a masked cyano group. A masked cyano group is a chemically protected form of a cyano group, in which the cyano group is in the form of a protected or protecting group (also known as a masked or masking group or a blocked or blocking group). In certain embodiments, a masked cyano group is —C(O)NH$_2$, —C(O)NRR, and —C=NOH (aldoxime).

Deprotection of the masked cyano group to present a cyano group facilitates the condensation reaction. In certain embodiments, deprotection of the masked cyano group can occur in vitro, in vivo, or ex vivo.

For the aminothiol derivative, the compound can comprise a thiol group or a masked thiol group. A masked thiol group is a chemically protected form of a thiol group, in which the thiol group is in the form of a protected or protecting group (also known as a masked or masking group or a blocked or blocking group). Examples of masked thiol groups can be found in Protective Groups in Organic Synthesis (T. Green and P. Wuts; 3rd Edition; John Wiley and Sons, 1999, for example at pages 454-493). In certain embodiments, a masked thiol group is a thioether, thioester, or disulfide.

Deprotection of the masked thiol group to present a thiol group facilitates the condensation reaction. In certain embodiments, deprotection of the masked thiol group can occur in vitro, in vivo, or ex vivo.

For the aminothiol derivative, the compound can comprise an amino group or a masked amino group. A masked amino group is a chemically protected form of an amino group, in which the amino group is in the form of a protected or protecting group (also known as a masked or masking group or a blocked or blocking group). Examples of masked amino groups can be found in Protective Groups in Organic Synthesis (T. Green and P. Wuts; 3rd Edition; John Wiley and Sons, 1999, for example at pages 494-659). In certain embodiments, a masked amino group is a carbamate or an amide.

In certain embodiments, the masked amino group is presented such that the amino group is connected to an amino acid, peptide, or protein. In certain embodiments, the amino acid, amino acid, peptide, or protein can be cleaved due to specific conditions.

Deprotection of the masked amino group to present an amino group facilitates the condensation reaction. In certain embodiments, deprotection of the masked amino group can occur in vitro, in vivo, or ex vivo.

Luciferin-Unmasking Reaction

For a luciferin-unmasking reaction, a luciferin derivative provides a carboxyl group and a heteroatom functional group in which either of the groups can be protected. In certain embodiments, the heteroatom functional group is —OH or —NH$_2$. If any of the carboxyl group or heteroatom functional groups is protected, the luminescence reaction will not likely proceed. Thus, the luminescence reaction can be controlled by addition and removal of protecting groups on any of the carboxyl group and heteroatom functional groups. An example of the luciferin-unmasking reaction is shown below.

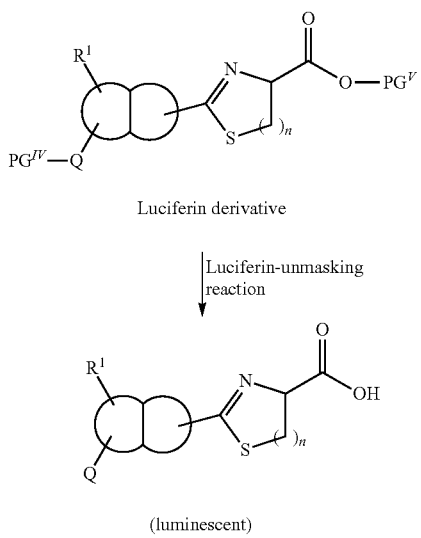

Luciferin derivative

Luciferin-unmasking reaction (luminescent)

For the luciferin derivative, the compound can comprise a carboxyl or a masked carboxyl group. A masked carboxyl group is a chemically protected form of a carboxyl group, in which the carboxyl group is in the form of a protected or protecting group (also known as a masked or masking group or a blocked or blocking group). Examples of masked carboxyl groups can be found in Protective Groups in Organic Synthesis (T. Green and P. Wuts; 3rd Edition; John Wiley and Sons, 1999, for example at pages 369-463). In certain embodiments, a masked carboxyl group is an ester, an amide, or a hydrazide.

In certain embodiments, the masked carboxyl group is presented such that the carboxyl group is connected to an amino acid, peptide, or protein. In certain embodiments, the amino acid, amino acid, peptide, or protein can be cleaved due to specific conditions.

Deprotection of the masked carboxyl group to present a carboxyl group facilitates the luminescence reaction. In certain embodiments, deprotection of the masked carboxyl group can occur in vitro, in vivo, or ex vivo.

For the luciferin derivative, the compound can comprise a heteroatom functional group or a masked heteroatom functional group, in which the heteroatom functional group is —OH or —NH$_2$. As shown in the formula above, the heteroatom functional group this is protected is -Q-PG$^{IV}$. Deprotection of the heteroatom functional group can be performed with procedures in Protective Groups in Organic Synthesis (T. Green and P. Wuts; 3rd Edition; John Wiley and Sons, 1999). In certain embodiments, a masked hydroxyl group is an ether or ester. In certain embodiments, a masked amino group is a carbamate or an amide.

In certain embodiments, the masked amino group is presented such that the amino group is connected to an amino acid, peptide, or protein. In certain embodiments, the amino acid, amino acid, peptide, or protein can be cleaved due to specific conditions.

Deprotection of the masked heteroatom functional group to present a heteroatom functional group facilitates the luminescence reaction. In certain embodiments, deprotection of the masked heteroatom functional group can occur in vitro, in vivo, or ex vivo.

Orthogonal Protecting Groups

In the presence of certain biomolecules or certain biological processes or changes in biological conditions, the protecting groups can be removed and the condensation reaction and/or luciferin-unmasking reaction can proceed to produce a luciferin, which can provide detectable luminescence. Thus, the condensation reaction and luciferin-unmasking reaction can serve as a detection system for certain biomolecules or certain biological processes or changes in biological conditions.

Multiple protecting groups can be utilized in the condensation reaction and luciferin-unmasking reaction. With orthogonal protecting groups, detection of presence of different biomolecules or different biological processes or different changes in biological conditions can be determined.

The bicyclic reactant and aminothiol derivative are shown below.

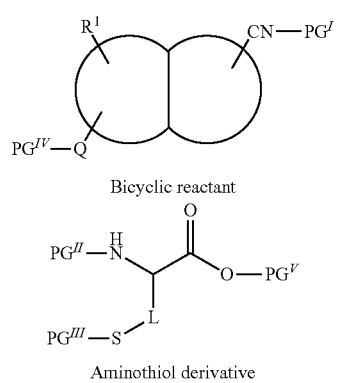

Bicyclic reactant

Aminothiol derivative

The reaction partners comprise up to five protecting groups: PG$^{I}$, PG$^{II}$, PG$^{III}$, PG$^{IV}$, and PG$^{V}$. In order for the condensation reaction and luciferin-unmasking reaction to occur to form luciferin with detectable luminescence, the protecting groups are removed from the reaction partners and resulting luciferin derivative.

Thus, each protecting group and up to five protecting groups can serve as a detection system for certain biomolecules or certain biological processes or changes in biological conditions. Examples are shown in Table 1, below.

TABLE 1

|  | Functional group to be protected | Examples of functional group as masked groups |
|---|---|---|
| PG$^I$ | Cyano | —C(O)NH$_2$, —C(O)NRR, and —C=NOH (aldoxime) |
| PG$^{II}$ | Amino | carbamate and amide (amino acid, amino acid, peptide, and protein) |
| PG$^{III}$ | Thiol | thioether, thioester, and disulfide |
| PG$^{IV}$ | Hydroxyl | ether and ester |
|  | Amino | carbamate and amide (amino acid, amino acid, peptide, and protein) |
|  | Thiol | thioether and thioester |
| PG$^V$ | Carboxyl | ester, amide, and hydrazide (amino acid, amino acid, peptide, and protein) |

Each of the protecting groups can have different conditions for deprotection. Thus, for example, while one protecting group can be removed under one set of conditions; another protecting group can be removed under another set of conditions. The conditions for deprotection of the protecting groups can be associated with certain biomolecules or certain biological processes or changes in biological conditions, thus serving as a detection system for these biomolecules, biological processes, or changes in biological conditions. In certain embodiments, removal of the protecting groups can be performed under general conditions (such a pH or the like) or certain conditions (such as in the presence of certain enzymes with certain cleavage sites).

The table below shows protecting groups that can be used in the compounds herein. The protecting group can be removed from the compound with certain biomolecules. Certain biomolecules are present in certain conditions or pathologies and thus are associated with certain conditions or pathologies. Examples are shown in Table 2, below.

TABLE 2

| Protecting group moiety | Functional group to be protected | Biomolecule for deprotection | Condition/Pathology |
|---|---|---|---|
| Aryl Boronate/aryl boronic acid (as part of protecting group) | cyano, amino, thiol, hydroxyl, carboxyl | H$_2$O$_2$ | Inflammation, cancer, neurodegeneration, diabetes, cardiovascular disease, ageing |
| z-LETD-, z-IETD- | Amino | Caspase-8 | Inflammation, apoptosis, sepsis, neurodegenerative disease |
| Pro-X-X-Hy (where X represents an arbitrary residue; Hy, a hydrophobic residue; e.g., Pro-Leu/Gln-Gly-Met-Thr-Ser or Pro-Leu/Gln-Gly-Met-Thr; or SPQGIAGQRNFN) | Amino | MMP-9 | Conditions/diseases where the extracellular maxtrix is broken down, cancer, embryonic development, reproduction, tissue remodeling (wound repair), arthritis, atherosclerosis, abdominal aortic aneurysm, inflammation |
| plasminogen activator cleavage site, e.g., a uPA or a tissue plasminogen activator (tPA) cleavage site; e.g., sequences comprising Val-Gly-Arg | Amino | uPA tPA | activated during thrombolyis or fibrinolysis, involved in extracellular matrix degradation, cancer, vascular diseases, stroke |
| SLLKSRMVPNFN or SLLIARRMPNFN | Amino | Cathepsin B | Cancer, stroke, neuro-degeneration, arthritis, ebola, chronic obstructive pulmonary disease, chronic peridontitis, ocular disorders, myocardial infarction |
| RPKPQQFFGLMN | Amino | MMP-3 (stromelysin) | Conditions/diseases where the extracellular maxtrix is broken down, cancer, embryonic development, reproduction, tissue re-modeling (wound repair), arthritis, atherosclerosis, abdominal aortic aneurysm, inflammation |
| SLRPLALWRSFN | Amino | MMP-7 (matrilysin) | Conditions/diseases where the extracellular maxtrix is broken down, cancer, embryonic development, reproduction, tissue remodeling (wound repair), arthritis, atherosclerosis, abdominal aortic aneurysm, inflammation |
| DVDERDVRGFASFL | Amino | Thermolysin-like MMP | Conditions/diseases where the extracellular maxtrix is broken down, cancer, embryonic development, reproduction, tissue |

TABLE 2-continued

| Protecting group moiety | Functional group to be protected | Biomolecule for deprotection | Condition/Pathology |
|---|---|---|---|
| SLPLGLWAPNFN | Amino | MMP-2 | remodeling (wound repair), arthritis, atherosclerosis, abdominal aortic aneurysm, inflammation Conditions/diseases where the extracellular maxtrix is broken down, cancer, embryonic development, reproduction, tissue remodeling (wound repair), arthritis, atherosclerosis, abdominal aortic aneurysm, inflammation |
| SLLIFRSWANFN | Amino | Cathepsin-L | Cancer, stroke, neuro-degeneration, arthritis, ebola, chronic obstructive pulmonary disease, chronic peridontitis, ocular disorders, myocardial infarction |
| SGVVIATVIVIT | Amino | Cathepsin-D | Cancer, stroke, neuro-degeneration, arthritis, ebola, chronic obstructive pulmonary disease, chronic peridontitis, ocular disorders, myocardial infarction |
| SLGPQGIWGQFN | Amino | MMP-1 | Conditions/diseases where the extracellular maxtrix is broken down, cancer, embryonic development, reproduction, tissue remodeling (wound repair), arthritis, atherosclerosis, abdominal aortic aneurysm, inflammation |
| KKSPGRVVGGSV | Amino | urokinase-type plasminogen activator | activated during thrombolyis, involved in extracellular matrix degradation, cancer, vascular diseases, stroke |
| PQGLLGAPGILG | Amino | membrane type 1 matrixmetalloproteinase | Conditions/diseases where the extracellular maxtrix is broken down, cancer, embryonic development, reproduction, tissue remodeling (wound repair), arthritis, atherosclerosis, abdominal aortic aneurysm, inflammation, emphysema, cirrhosis |
| HGPEGLRVGFYESDVMGRGHARLVHVEEPHT | Amino | MMP-11 (stromelysin-3) | Conditions/diseases where the extracellular maxtrix is broken down, cancer, embryonic development, reproduction, tissue remodeling (wound repair), arthritis, atherosclerosis, abdominal aortic aneurysm, inflammation, emphysema, cirrhosis |
| GPQGLAGQRGIV | Amino | MMP-13 (collagenase-3) | Conditions/diseases where the extracellular maxtrix is broken down, cancer, embryonic development, restructuring collagen matrix, reproduction, tissue remodeling (wound repair), arthritis, osteoarthritis, atherosclerosis, abdominal aortic aneurysm, inflammation |
| GGSGQRGRKALE | Amino | tissue-type plasminogen activator | activated during thrombolyis, involved in extracellular matrix degradation, cancer, vascular diseases, stroke, |

TABLE 2-continued

| Protecting group moiety | Functional group to be protected | Biomolecule for deprotection | Condition/Pathology |
|---|---|---|---|
| SLSALLSSDIFN | Amino | Human prostate-specific antigen | Prostate cancer, male ejaculate, prostate disorders, obesity (decreased levels), prostatitis, benign prostatic hyperplasia, ageing (increased in older men), found in breast milk and amniotic fluid, breast, lung, renal, and uterine cancer |
| SLLGIAVPGNFN | Amino | Neutrophil elastase | Inflammation, cyclic neutropenia, severe congenital neutropenia, neutrophil differentiation, emphysema |
| FFKNIVTPRTPP | Amino | calpain (calcium activated neutral protease) | Muscular dystrophy, necrosis, colon polyp formation, diabetes, cell mobility, cell cycle progression, cancer, long-term potentiation/memory, cell fusion, blood clotting, apoptosis, vascular disease, skeletal muscle protein breakdown (following exercise, during altered nutritional states), Alzheimer's disease, cataract formation. Causes degeneration following myocardial ischemia, cerebral ischemia, traumatic brain injury, and spinal cord injury. Causes cardiac contractile dysfunction following myocardial ischemia |
| $OPO_3Na_2$ | hydroxyl | Alkaline phosphatases | Increased levels when bile ducts are blocked, increased levels in children and pregnant women, during bone formation, and in seminomas, polycythemia vera, primary myelofibrosis. Decreased levels in hypophosphatasia, malnutrition, hypothyroidism, anemia, achondroplasia, cretinism, leukemia, Wilson's disease, hemoglobinuria, and following heart surgery. |
| Beta-D-galactoside | Hydroxyl | B-galactosidase activity | Decreased levels in galactosialidosis and Morquio B syndrome. Increased in senescent cells. |
| Ac-RRKY-, Ac-Arg-X-(Lys/Arg)-Arg- X = any amino acid residue | Amino | Furin activity | Cancer, juvenile hemochromatosis, viral pathogenesis, maintenance of immune tolerance |
| z-DEVD | Amino | Caspase 3/7 activity | Inflammation, apoptosis, sepsis, neurodegenerative disease |
| z-LEHD | Amino | Caspase-9 activity | Inflammation, apoptosis, sepsis, neurodegenerative disease |
| GP-, VP- | Amino | Dipeptidyl peptidase activity | Immune regulation, apoptosis, glucose metabolism, cancer, diabetes |
| Suc-LLVY, Z-QEVY- | Amino | Calpain- and chymotrypsin-like activity | Muscular dystrophy, necrosis, colon polyp formation, diabetes, cell mobility, cell cycle progression, cancer, long-term potentiation/memory, cell fusion, blood clotting, apoptosis, vascular disease, skeletal muscle protein breakdown |

TABLE 2-continued

| Protecting group moiety | Functional group to be protected | Biomolecule for deprotection | Condition/Pathology |
|---|---|---|---|
| | | | (following exercise, during altered nutritional states), Alzheimer's disease, cataract formation. Causes degeneration following myocardial ischemia, cerebral ischemia, traumatic brain injury, and spinal cord injury. Causes cardiac contractile dysfunction following myocardial ischemia. Inflammation, asthma, bronchitis, lung disease, infections, liver damage, wound repair, cystic fibrosis, food digestion |
| X-LRR- | Amino | Trypsin-like activity | Cystic fibrosis, renal disease, food digestion, pancreatic disease, chronic inflammatory bowel disease, Crohn's disease, cancer |
| Z-nLPnLD- | Amino | Caspase-like activity | Inflammation, apoptosis, sepsis, neurodegenerative disease |
| Z-VDVAD- | Amino | Caspase-2 activity | Inflammation, apoptosis, sepsis, neurodegenerative disease, DNA repair, tumor suppression, increased longevity |
| Z-VEID- | Amino | Caspase-6 activity | Inflammation, apoptosis, sepsis, neurodegenerative disease |
| Z-ATAD- | Amino | Caspase-12 activity | Inflammation, apoptosis, sepsis |
| Z-IEPD- | Amino | Granzyme B | Inflammation, apoptosis, sepsis, infection, immune response, |
| Z-IETD- | Amino | Granzyme B and Caspase 6 | Inflammation, apoptosis, sepsis, infection, immune response, neurodegenerative disease |
| Z-TSAVLQ-, Z-VNSTLQ- | Amino | SARS protease | Severe acute respiratory syndrome |
| Z-FR- | Amino | Cathepsins B/L | Cancer, stroke, neuro-degeneration, arthritis, ebola, chronic obstructive pulmonary disease, chronic peridontitis, ocular disorders, myocardial infarction |
| Boc-VPR- | Amino | Kallikrein or thrombin | Cancer, blood pressure regulation, semen liquefaction, skin desquamation, inflammation, neuronal plasticity, coagulation, autoimmune disease, vasospasm, subarachnoid hemorrhage, cerebral ischemia, stroke, atherosclerosis, apoptosis, angiogenesis |
| Z-GGR-, Z-Leu-Val-Pro-Arg-Gly-Ser | Amino | thrombin | Coagulation, autoimmune disease, vasospasm, subarachnoid hemorrhage, cerebral ischemia, stroke, inflammation, atherosclerosis, apoptosis, angiogenesis |
| Ac-K- | Amino | trypsin | Cystic fibrosis, renal disease, food digestion, pancreatic disease, chronic inflammatory bowel disease, Crohn's disease, cancer |
| AAF- | Amino | amino-peptidase | Digestion, kidney disease/disorders, infection, leukemia, lymphoma, liver damage, cancer, cholesterol gallstone disease, angiogenesis, |

TABLE 2-continued

| Protecting group moiety | Functional group to be protected | Biomolecule for deprotection | Condition/Pathology |
|---|---|---|---|
| Suc-AAPF- | Amino | Serine amino-peptidase | Digestion, kidney disease/disorders, infection, leukemia, lymphoma, liver damage, cancer, cholesterol gallstone disease, angiogenesis, |
| Z-PRNK- | Amino | tryptase | Mast cell activation, allergic response, anaphylaxis, |
| 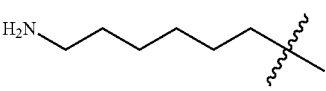 [SMILES: *CCCCCCN] | Amino, hydroxyl | N-acetyl-transferase 2 | Cancer, response to xenobiotic ompounds |
| 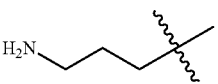 [SMILES: *CCCN] | Amino, hydroxyl | Monoamine oxidase | Psychiatric and neurological disorders, including depression, schizophrenia, Alzheimer's disease, and Parkinson's disease, |
| 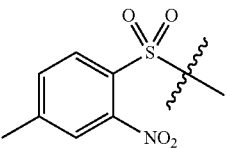 [SMILES: *S(=O)(=O)c1ccc(C)cc1[N+](=O)[O-]] | Amino, hydroxyl | Detection of reduced glutathione | Inflammation, oxidative stress, detoxification of xenobiotics, immune deficiency, sepsis, burns, HIV/AIDS, hepatitis, myalgic encephalomyelitis chronic fatigue syndrome, cancer, cataracts, Alzheimer's disease, Parkinson's disease, chronic obstructive pulmonary disease, asthma, radiation poisoning, mal-nutritive states, arduous physical stress, schizophrenia, bipolar disorder, major depressive disorder, traumatic brain injury, and aging |
| 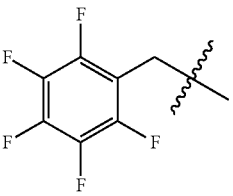 [SMILES: *Cc1c(F)c(F)c(F)c(F)c1F] | Amino, hydroxyl | 3A isozymes of the cytochrome P450 enzyme | Drug and steroid metabolism, testosterone metabolism |
| 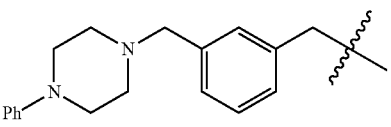 [SMILES: *Cc1cccc(CN2CCN(c3ccccc3)CC2)c1] | Amino, hydroxyl | CYP3A activity | Drug and steroid metabolism, testosterone metabolism |
| 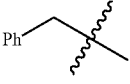 | Amino, hydroxyl | CYP3A4 and 3A7 isozyme of P450 family | Drug and steroid metabolism, testosterone metabolism |
| H (hydrogen) | | CYP2C9 activity, hydroxyl radical | Drug and steroid metabolism |
| 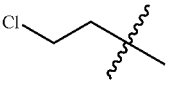 [SMILES: *CCCl] | Amino, hydroxyl | CYP1A1 and CYP1B1 activity | Drug and steroid metabolism, estrogen metabolism |
|  | hydrooxyl | CYP1A2, CYP4A, and CYP2C8 activity | Drug and steroid metabolism, estrogen metabolism, arachidonic acid metabolism, fatty acid metabolism |

TABLE 2-continued

| Protecting group moiety | Functional group to be protected | Biomolecule for deprotection | Condition/Pathology |
|---|---|---|---|
| 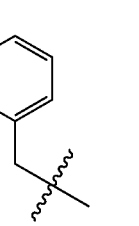 | Amino, hydroxyl | CYP3A7 activity | Drug and steroid metabolism, testosterone metabolism |
| 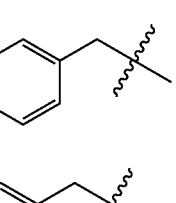 | Amino, hydroxyl | CYP4F2 and CYP4F3 activity | arachidonic acid metabolism, fatty acid metabolism |
|  | Amino, hydroxyl | CYP4F12 activity | arachidonic acid metabolism, fatty acid metabolism |
| 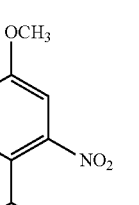 | Amino, hydroxyl | CYP4F12 and CYP2J2 activity | Drug and steroid metabolism, arachidonic acid metabolism, fatty acid metabolism |
| 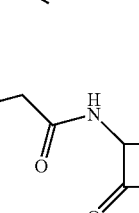 | Amino, hydroxyl | Light, esterases | |
| 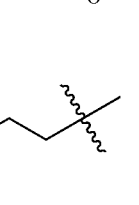 | Amino, hydroxyl | Beta-lactamase activity | bacteria levels/activity, bacterial resistance |
| 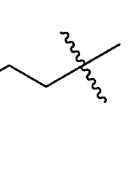 | Amino, hydroxyl | Monoamine oxidase | Psychiatric and neurological disorders, including depression, schizophrenia, Alzheimer's disease, and Parkinson's disease, |
|  | Amino, hydroxyl | Monoamine oxidase | Psychiatric and neurological disorders, including depression, schizophrenia, Alzheimer's disease, and Parkinson's disease, |

TABLE 2-continued

| Protecting group moiety | Functional group to be protected | Biomolecule for deprotection | Condition/Pathology |
|---|---|---|---|
| (dimethylaminoisopentyl structure) | Amino, hydroxyl | Monoamine oxidase | Psychiatric and neurological disorders, including depression, schizophrenia, Alzheimer's disease, and Parkinson's disease, |
| (phenylthioethyl and ethylthioethyl structures); (ethylsulfinylethyl and methylaminopentyl structures) | Amino, hydroxyl | Flavin-containing mono-oxygenase | Metabolism of xenobiotics, tri-methylaminuria, redox cycling of glutathione |
| (various nitro- and trifluoromethyl-substituted benzyl and sulfonyl structures) | Amino, hydroxyl | Glutathione S-transferase | Xenobiotic metabolism, drug metabolism, metabolism of endogenous compounds, cancer, DNA damage, kidney damage, |

TABLE 2-continued

| Protecting group moiety | Functional group to be protected | Biomolecule for deprotection | Condition/Pathology |
|---|---|---|---|
| 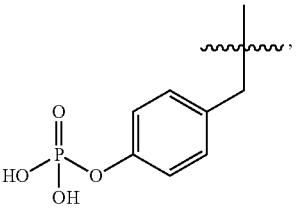 [SMILES: *Cc1ccc(OP(=O)(O)O)cc1] | Amino, hydroxyl | Alkaline phosphatases | Increased levels when bile ducts are blocked, increased levels in children and pregnant women, during bone formation, and in seminomas, polycythemia vera, primary myelofibrosis. Decreased levels in hypophosphatasia, malnutrition, hypothyroidism, anemia, achondroplasia, cretinism, leukemia, Wilson's disease, hemoglobinuria, and following heart surgery. |
| 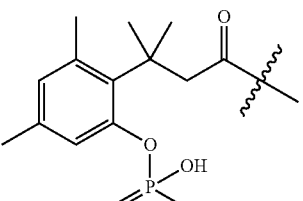 | | | |
| 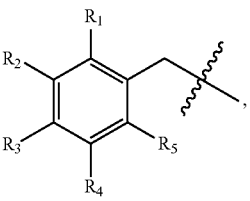<br>$R_1$-$R_5$ are independently H, F, alkyl, aryl, hydroxyalkyl, or short PEG. | Amino, hydroxyl | CYP3A4 activity, other P450 enzymes | Drug and steroid metabolism, testosterone metabolism, arachidonic acid metabolism, fatty acid metabolism, steroid biosynthesis, cholesterol biosynthesis |
| 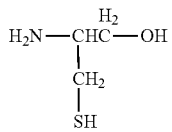<br>(instead of D-cysteine) | Replacement of carboxyl group on D-cysteine | Alcohol dehydrogenase | Alcohol metabolism, drug and alcohol dependence, Parkinson's disease, retinoid and dopamine metabolism, liver disease, hepatitis |
| Boc-Orn(Ac)O—, Boc-Lys(Ac)HN— | Hydroxyl, amino | Histone deacetylase | Psychiatric and neurological disorders, cancer, chronic myeloid leukemia, schizophrenia, cell growth and death, neurodegenerative diseases, HIV, inflammation, polycythemia vera, essential thrombocythemia, myelofibrosis, heart disease, and myocardial infarction |
| Z-KKR-SEVNLDAEFR-HN- | Amino | B-secretase | Alzheimer's disease, down syndrome |
| AAF-HN- | Amino | Proteases | Food digestion, blood clotting, apoptosis, immune response, inflammation, infection, bacterial and viral pathogenesis and virulence, hormone regulation, cell regulation and differentiation, extracelluar matrix remodeling, atherosclerosis, emphysema |
| Z-FR-HN- | Amino | Cathepsin B, L | Cancer, stroke, neurodegeneration, arthritis, ebola, chronic obstructive pulmonary disease, chronic peridontitis, ocular disorders, myocardial infarction |

TABLE 2-continued

| Protecting group moiety | Functional group to be protected | Biomolecule for deprotection | Condition/Pathology |
|---|---|---|---|
| Z-GGR-HN-<br>Z-GPR-HN- | Amino | Thrombin assay | Coagulation, autoimmune disease, vasospasm, subarachnoid hemorrhage, cerebral ischemia, stroke, inflammation, atherosclerosis, apoptosis, angiogenesis |
| Z-1EPD-HN- | Amino | Cytotoxic response CTL, Granzyme B | Cancer, inflammation, apoptosis, sepsis, infection, immune response, hepatitis B, arthritis |
| N-acetyl-2,3-dihydroluciferin<br>D-cysteine-CO$_2$-amino acid, D-cysteine-CO$_2$-peptide | carboxyl | HRP substrate<br>Mycoplasma carboxypeptidase | Food digestion, post-translational modification, biosynthesis of neuro-endocrine peptides (e.g. insulin), diabetes, blood clotting, growth factor production, wound healing, reproduction, |
| 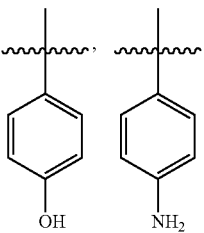 | Hydroxyl, amino | Reactive oxygen species (hydroxyl radical, peroxynitrite, hypochlorite) | Inflammation, ageing, neurodegenerative disease, cardiovascular disease, diabetes, cancer |
| 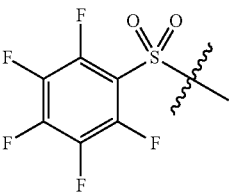 [SMILES: *S(=O)(=O)c1c(F)c(F)c(F)c(F)c1F] | Hydroxyl, amino | Hydrogen peroxide | Inflammation, ageing, neurodegenerative disease, cardiovascular disease, diabetes, cancer |

Cleavable Linkers

In certain embodiments, the protecting group for amino group or hydroxyl group on the bicyclic reactant can be or can comprise a cleavable linker group that provides for release of the bicyclic moiety upon reaction. The protecting group can include a reactive group linked to the bicyclic reactant by a cleavable linker. Once the reactive group is removed, the linked can be cleaved.

As used herein, the term "cleavable linker group" refers to a linker that can be selectively cleaved to produce at least two products. Application of suitable cleavage conditions to a molecule containing a cleavable linker that is cleaved by the cleavage conditions will produce the byproducts. A cleavable linker of the embodiments is stable, e.g. to physiological conditions, until the molecule is contacted with a cleavage-inducing stimulus, such as a cleavage-inducing agent.

In certain embodiments, in the bicyclic reactant, PG$^{IV}$ can be

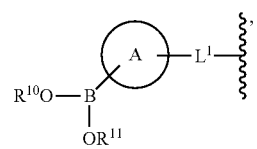

wherein

R$^{10}$ and R$^{11}$ are selected from hydrogen and alkyl; or R$^{10}$ and R$^{11}$ together form a boronic ester ring or substituted boronic ester ring;

A ring is selected from aryl, substituted aryl, heteroaryl, and substituted heteroaryl;

L$^1$ is cleavable linker group that provides for release of the bicyclic reactant upon reaction of the —B(OR$^1$)(OR$^2$) group with a reactive oxygen species.

Thus, the disclosure provides a compound of formula:

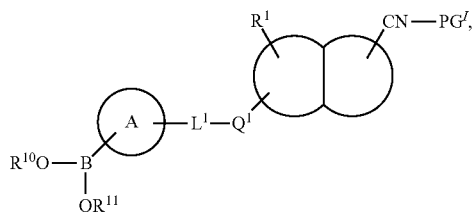

wherein $R^{10}$ and $R^{11}$ are selected from hydrogen and alkyl; or $R^{10}$ and $R^{11}$ together form a boronic ester ring or substituted boronic ester ring;

A ring is selected from aryl, substituted aryl, heteroaryl, and substituted heteroaryl;

$L^1$ is cleavable linker group that provides for release of the bicyclic reactant upon reaction of the —$B(OR^1)(OR^2)$ group with a reactive oxygen species;

and $Q^1$, $R^1$ and $PG^1$ are defined as herein.

In certain instances, $R^{10}$ and $R^{11}$ can be selected from hydrogen and alkyl; or $R^{10}$ and $R^{11}$ together can form a boronic ester ring or substituted boronic ester ring. In certain instances, both $R^{10}$ and $R^{11}$ are hydrogen. In certain instances, both $R^{10}$ and $R^{11}$ are alkyl, such as, for example, methyl, ethyl, propyl, isopropyl, and butyl. In certain instances, $R^{10}$ and $R^{11}$ together form a boronic ester ring or substituted boronic ester ring. In certain instances, $R^1$ and $R^2$ together form a boronic ester ring. In certain instances, $R^{10}$ and $R^{11}$ together form a substituted boronic ester ring. In certain instances, the —$B(OR^{10})(OR^{11})$ group is selected from the following:

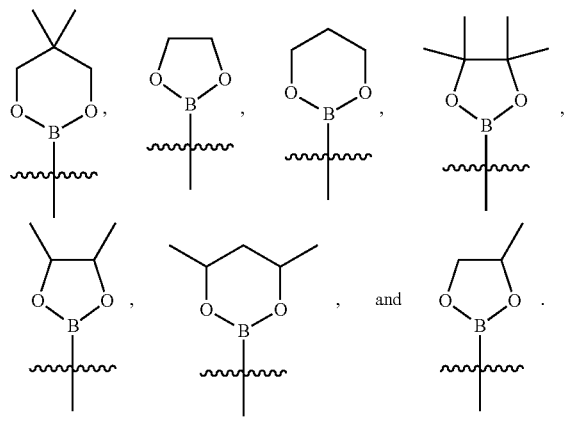

In certain embodiments, the A ring can be selected from aryl, substituted aryl, heteroaryl, and substituted heteroaryl. In certain instances, the A ring is aryl. In certain instances, the A ring is substituted aryl. In certain instances, the A ring is phenyl. In certain instances, the A ring is substituted phenyl. In certain instances, the A ring is heteroaryl. In certain instances, the A ring is substituted heteroaryl. In certain instances, the A ring is pyridinyl. In certain instances, the A ring is substituted pyridinyl. The A ring connects the —$B(OR^{10})(OR^{11})$ group and $L^1$. The arrangement of these groups on the A ring is at any suitable ring positions that provides for electronic communication between the two groups (e.g., delocalization of a lone pair of electrons from one group to the other). For example, when A is a phenyl ring, arrangement of the —$B(OR^{10})(OR^{11})$ group and $L^1$ group either ortho- or para- to each other provides for delocalization of a lone pair of electrons from the site of —$B(OR^{10})(OR^{11})$ group oxidation to the cleavable bond of the cleavable linker.

In certain embodiments, $L^1$ is cleavable linker group that provides for release of a bicyclic reactant upon reaction of the —$B(OR^1)(OR^2)$ group with a reactive oxygen species, where release of a bicyclic reactant includes cleavage of a cleavable bond to release a leaving group.

For example, upon reaction (e.g., a hydroboration-oxidation reaction) of the aryl or heteroaryl —$B(OR^1)(OR^2)$ group with a reactive oxygen species (e.g., $H_2O_2$), the cleavable bond of the cleavable linking group $L^1$ is spontaneously cleaved to release the leaving group and a bicyclic reactant. The cleavable bond connects the leaving group to an adjacent carbon atom that is conjugated to the aryl boronate group that is oxidized. A cascade occurs in which an electron pair is donated from the site of oxidation through the aryl or heteroaryl group to the carbon atom adjacent to the leaving group of the linker, thereby cleaving the cleavable bond. The $L^1$ linker group provides for release of a bicyclic reactant by fragmentation or cleavage of the linker with the donation of the electron pair. The $L^1$ linker group comprises segments of atoms, in which the segments can be displaced into two byproducts after a cleavage-inducing stimulus (e.g., reaction of the —$B(OR^1)(OR^2)$ group with a reactive oxygen species).

The $L^1$ linker group can include one or more groups such as, but not limited to, alkyl, ether, carbamate, carbonate, carbamide (urea), ester, thioester, aryl, amide, imines, phosphate esters, hydrazones, acetals, orthoesters, and combinations thereof. In some embodiments, the $L^1$ linker group is described the following structure:

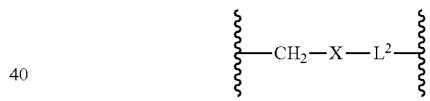

where X is a leaving group and $L^2$ is a linking group, wherein the bond that connects X to the adjacent —$CH_2$— group (e.g., $CH_2$—X) is a cleavable bond. In some embodiments X is oxygen or sulfur. In some embodiments, the leaving group is a carbamate, a carbonate, a thiol, an alcohol, an amino (e.g., an aryl amino) or a phenol group.

In certain embodiments, the linking group $L^2$ is a covalent bond or a chain of between 1 and 12 atoms in length (e.g., between 1 and 10, 1 and 8, 1 and 6 or 1 and 4 atoms in length). In some cases, $L^2$ is a chain of between 1 and 12 atoms in length that further includes a second leaving group adjacent to the bicyclic reactant (e.g., $L^2$ has a structure $L^3$-$X^2$ where $L^3$ is a linking group and $X^2$ is the second leaving group, e.g., O, NH or NR where R is an alkyl), such that upon cleavage of the cleavable bond ($CH_2$—X), a moiety is released (e.g., HX-$L^3$-$X^2$-$Q^1$) that includes both the first leaving group (X), $L^3$-$X^2$ and the bicyclic reactant. In such cases, the released moiety (e.g., HX-$L^3$-$X^2$-$Q^1$) may undergo further cleavage or fragmentation (e.g., via an intramolecular cyclization-release) to release $HX^2$-$Q^1$. In some embodiments, $L^2$ is a covalent bond, such that upon cleavage of the cleavable bond ($CH_2$—X), a moiety is released (e.g., HX-$Q^1$) that includes both the leaving group and the bicyclic reactant. When referring to the bicyclic moiety that is released, it is understood that the leaving group and segments of the linker may be attached to the released bicyclic moiety being described. It is understood that in any of the embodiments described herein that upon cleavage of the cleavable bond of the linker, a bicyclic moiety is released that may undergo further cleavage/fragmentation (e.g., via an intramolecular cyclization-release).

In certain instances, the -L¹-Q¹-group is selected from the following:

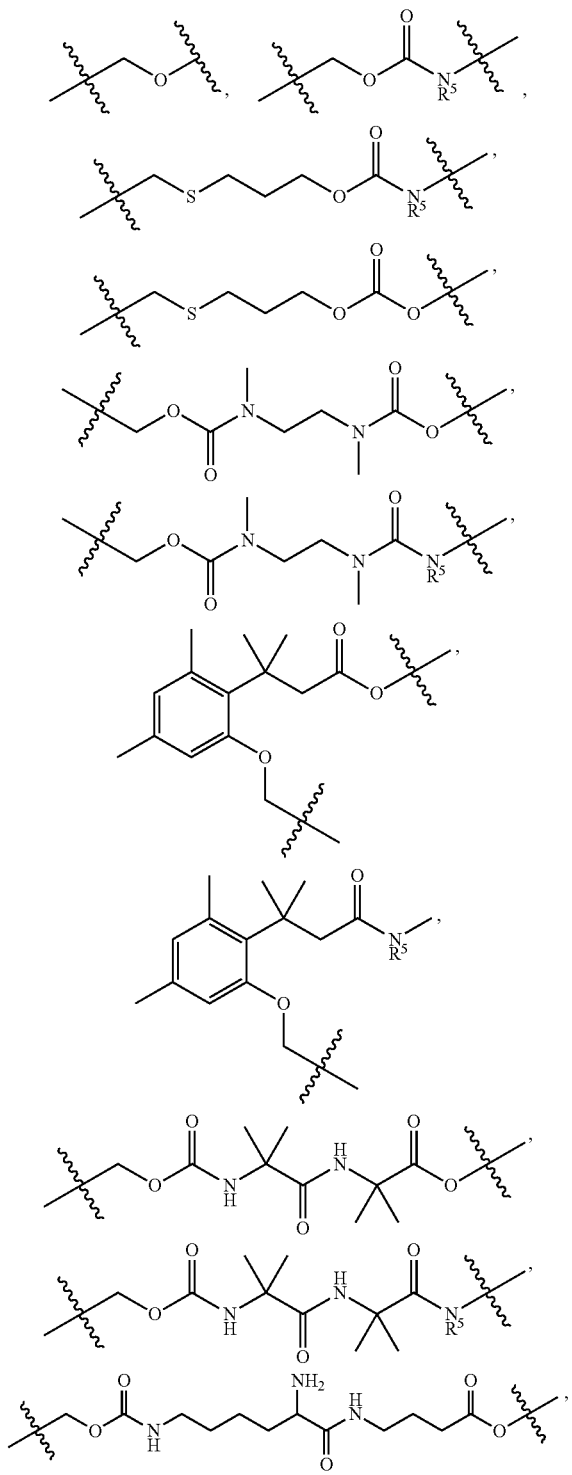

where $R^5$ is hydrogen, alkyl, substituted alkyl or alkoxy, where optionally $R^5$ may be covalently connected to the bicyclic reactant (e.g., to form a fused ring system).

In certain embodiments, the disclosure provides a method for detection of a biological process or biomolecule in a test subject, the method comprising contacting test subject with a compound of any of Formula I-V and a compound of Formula VI. The method can further comprise monitoring the test subject for luminescence, wherein luminescence indicates the presence of the biological process or biomolecule. In certain embodiments, more than one biological process or biomolecule in a test subject can be monitored. For example, orthogonal protecting groups can be used in the compounds for the condensation reaction and luciferin-unmasking reaction in a manner to allow for monitoring of more than one biological process or biomolecule in a test subject. In certain embodiments, the biological process is any one of the conditions/pathologies in Table 2 above. In certain embodiments, the biological process is cancer, a cardiovascular disorder, diabetes, or a neurodegenerative disease. In certain embodiments, the biological process is an inflammatory response. In certain embodiments, the biomolecule detected is any one of the biomolecules in Table 2 above. In specific embodiments, the biomolecule is caspase-8 and/or $H_2O_2$.

Compositions

The present disclosure provides compositions, including pharmaceutical compositions, comprising a subject compound. Compositions comprising a subject compound can include one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a membrane penetration facilitator; and the like.

The present disclosure provides pharmaceutical compositions comprising a subject compound. A subject compound can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A subject compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. In some cases, a suitable excipient is dimethylsulfoxide (DMSO). In other cases, DMSO is specifically excluded.

For oral preparations, a subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycol monomethyl ethers, which melt at body temperature, yet are solidified at room temperature.

Utility

A subject compound, and a subject composition, finds use in various applications. A subject compound can be used in various diagnostic and detection methods.

Detection of Certain Biomolecules or Certain Biological Processes or Changes in Biological Conditions in a Living Cell In Vitro The present disclosure provides a method of detecting certain biomolecules or certain biological processes or changes in biological conditions in a living cell in vitro. In some embodiments, a subject detection method involves contacting subject compounds with a living cell in vitro, e.g., a subject compound is contacted with cells growing in suspension (e.g., as unicellular entities) or as a monolayer in in vitro cell culture; and detecting a signal generated by reactions of the subject compounds. The cells can be primary cells, non-transformed cells, cells isolated from an individual, immortalized cell lines, transformed cells, etc.

Non-limiting examples of cells are cells of multicellular organisms, e.g., cells of invertebrates and vertebrates, such as myoblasts, neutrophils, erythrocytes, osteoblasts, chondrocytes, basophils, eosinophils, adipocytes, invertebrate neurons (e.g., Helix aspera), vertebrate neurons, mammalian neurons, adrenomedullary cells, melanocytes, epithelial cells, and endothelial cells; tumor cells of all types (e.g., melanoma, myeloid leukemia, carcinomas of the lung, breast, ovaries, colon, kidney, prostate, pancreas and testes); cardiomyocytes, endothelial cells, lymphocytes (T-cell and B cell), mast cells, vascular intimal cells, hepatocytes, leukocytes including mononuclear leukocytes; stem cells such as hematopoietic stem cells, neural, skin, lung, kidney, liver and myocyte stem cells; osteoclasts, connective tissue cells, keratinocytes, melanocytes, hepatocytes, and kidney cells.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable methods of detecting a signal generated by reaction of subject compounds in a living cell in vitro include, e.g., microscopy, fluorescence activated cell sorting, spectroscopy (e.g., a multi-well plate reader that detects luminescence), luminometers, photomultiplier tubes, a charged-coupled device (CCD) camera; a cooled CCD camera, and the like.

Detection of Certain Biomolecules or Certain Biological Processes or Changes in Biological Conditions In Vivo, in a Living Cell In Vivo or in an Extracellular Compartment of a Multicellular Organism The present disclosure provides a method of detecting certain biomolecules or certain biological processes or changes in biological conditions in a living cell in vivo, e.g., in a living multicellular organism. In some embodiments, the method involves administering a compound of the embodiments (or a composition comprising a compound of the embodiments) to a multicellular organism (e.g., an individual such as a mammal); and detecting a signal generated by reaction of the subject compounds in a cell of the multicellular organism (e.g., in a cell of the individual).

A subject detection method can also be carried out ex vivo, e.g., where a tissue or cells are taken from an individual and imaged.

The present disclosure also provides a method of detecting certain biomolecules or certain biological processes or changes in biological conditions in a multicellular organism. In some embodiments, the method involves administering a compound of the embodiments (or a composition comprising a compound of the embodiments) to a multicellular organism (e.g., an individual such as a mammal); and detecting a signal generated by reaction of the subject compounds in the multicellular organism. In certain embodiments, the certain biomolecules or certain biological processes or changes in biological conditions can be present in an extracellular fluid (e.g., cerebrospinal fluid, lymph, plasma, and the like) or other extracellular environment.

Suitable methods of detecting a signal generated by reaction of subject compounds in a living cell in vitro include, e.g., microscopy, fluorescence activated cell sorting, spectroscopy (e.g., a multi-well plate reader that detects luminescence), luminometers, photomultiplier tubes, and the like. Suitable methods of detecting a signal generated by reaction of subject compounds in a living cell in vivo include, e.g., use of a charged-coupled device (CCD) camera; a cooled CCD camera; or any other device capable of bioluminescent imaging. Use of a CCD camera can allow three-dimensional imaging.

A subject detection method can be used to detect certain biomolecules or certain biological processes or changes in biological conditions in a cell (e.g., a single cell in vitro; or a cell in a multicellular organism; or in a fluid in a multicellular organism) over time. For example, the certain biomolecules or certain biological processes is detected at a first time and at a second time; and the levels of the certain biomolecules or certain biological processes detected at the first and second times are compared. In some embodiments, the first time is before treatment with an agent (e.g., a therapeutic agent); and the second time is after treatment with an agent. In these embodiments, the level of the certain biomolecules or certain biological processes can be used to determine the effect of treatment of an individual with the agent. In other embodiments, the first time is at a first age of a multicellular organism; and the second time is at a second age of the multicellular organism. In these embodiments, the change in level of the certain biomolecules or certain biological processes with age can be monitored.

A subject compound can be used to determine the effect that an agent has on the level of the certain biomolecules or certain biological processes in a cell and/or cells (e.g., a single cell in vitro; or a cell in a multicellular organism; or in a fluid in a multicellular organism). Agents that can be tested for an effect on the level of the certain biomolecules or certain biological processes in a cell include, but are not limited to, therapeutic agents; growth factors; neurotransmitters; anesthetics; hormones; metal ions; receptor agonists; receptor antagonists; and any other agent that can be administered to cells and/or multi-cellular organisms.

A subject compound can be administered to an individual via any number of modes and routes of administration. In some embodiments, a subject compound is administered systemically (e.g., via intravenous injection; via oral administration; via intraperitoneal injection etc.). In other embodiments, a subject compound is administered locally. A subject compound can be administered intravenously, intratumorally, peritumorally, orally, topically, subcutaneously, via intraocular injection, rectally, vaginally, or any other enteral or parenteral route of administration.

Detection of Certain Biomolecules or Certain Biological Processes or Changes in Biological Conditions in a Cell-Free Sample The present disclosure provides a method of detecting certain biomolecules or certain biological processes or changes in biological conditions in a cell-free sample in vitro. In some embodiments, a subject detection method involves contacting a subject compound with a cell-free sample in vitro; and detecting a signal generated by reaction of the subject compounds in the cell-free sample. In some embodiments, the cell-free sample is a biological sample.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Syntheses of CBT Derivatives and Aminothiol Derivatives

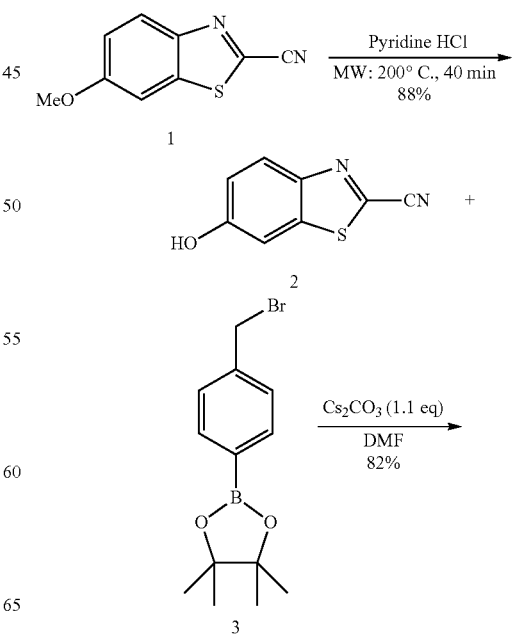

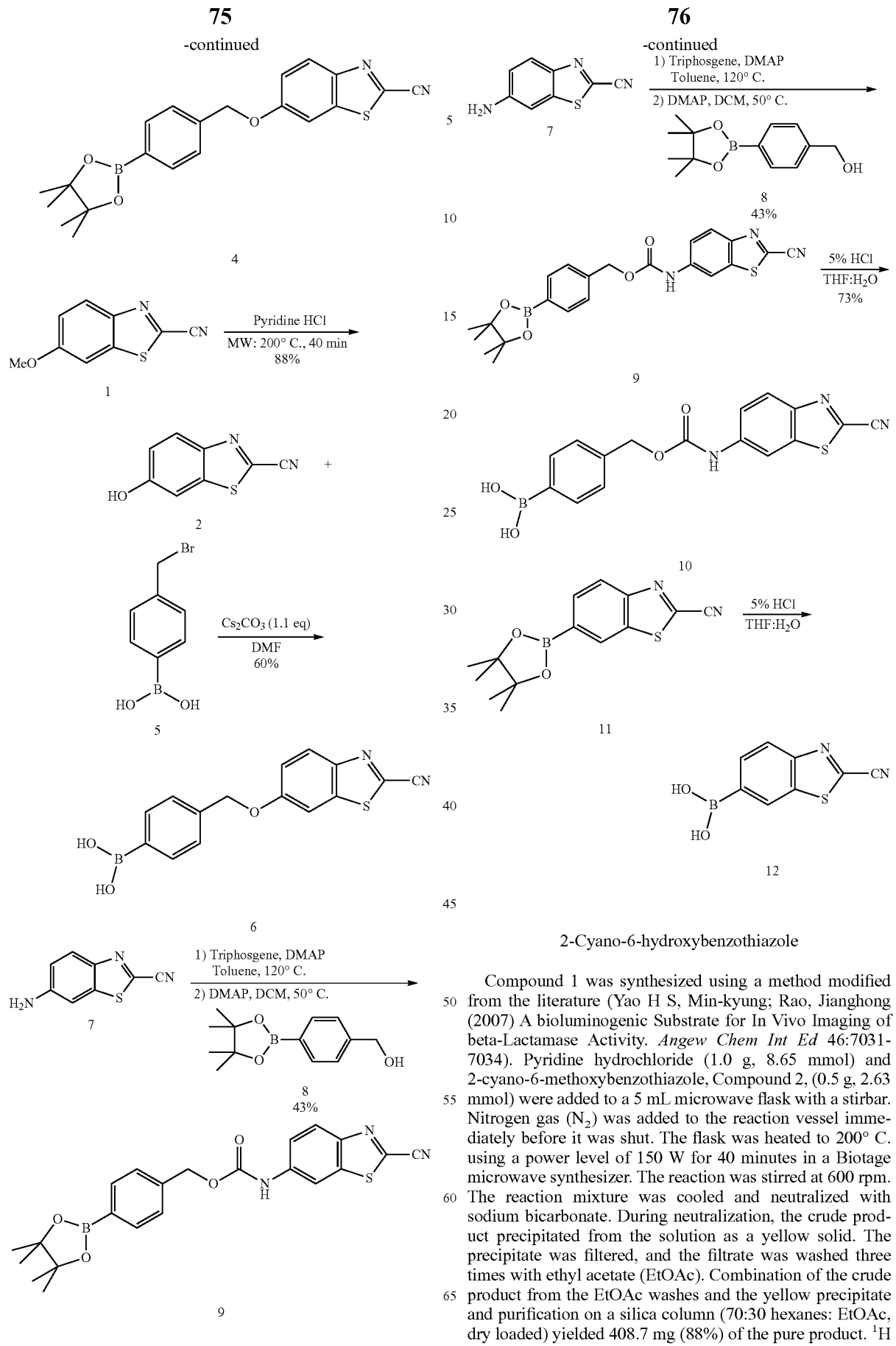

2-Cyano-6-hydroxybenzothiazole

Compound 1 was synthesized using a method modified from the literature (Yao H S, Min-kyung; Rao, Jianghong (2007) A bioluminogenic Substrate for In Vivo Imaging of beta-Lactamase Activity. *Angew Chem Int Ed* 46:7031-7034). Pyridine hydrochloride (1.0 g, 8.65 mmol) and 2-cyano-6-methoxybenzothiazole, Compound 2, (0.5 g, 2.63 mmol) were added to a 5 mL microwave flask with a stirbar. Nitrogen gas ($N_2$) was added to the reaction vessel immediately before it was shut. The flask was heated to 200° C. using a power level of 150 W for 40 minutes in a Biotage microwave synthesizer. The reaction was stirred at 600 rpm. The reaction mixture was cooled and neutralized with sodium bicarbonate. During neutralization, the crude product precipitated from the solution as a yellow solid. The precipitate was filtered, and the filtrate was washed three times with ethyl acetate (EtOAc). Combination of the crude product from the EtOAc washes and the yellow precipitate and purification on a silica column (70:30 hexanes: EtOAc, dry loaded) yielded 408.7 mg (88%) of the pure product. $^1$H NMR (300 MHz, CD$_3$OD): δ 7.13 (1H, dd, J=9 Hz), 7.36 (1H, d, J=2.1 Hz), 7.95 (1H, d, J=9 Hz). LRESI-MS: calculated for [C$_8$H$_4$N$_2$OS] 176.0. found 176.1.

6-(4-(4,4,5,5-Tetramethyl-1,3,2-dioxaborolan-2-yl)benzyloxy)benzo[d]thiazole-2-carbonitrile (4)

2-Cyano-6-hydroxybenzothiazole (300 mg, 1.7 mmol) and 4-(bromomethyl)benzeneboronic acid pinacol ester (505.7 mg, 1.7 mmol) were dissolved in 30 mL dry DMF prior to the addition of cesium carbonate (610.25 mg, 1.87 mmol). The mixture was stirred at 60° C. for 45-50 minutes before it was allowed to cool to room temperature. 100 mL EtOAc was added to the reaction mixture, and the organic phase was washed three times with deionized water (DI H$_2$O). The aqueous layers were combined and washed three times with EtOAc. All of the organic layers were combined, washed twice with brine, dried over sodium sulfate, and concentrated. The crude material was purified on a silica column (90:10 hexanes:ethyl acetate, dry loaded) to give 547.4 mg (82%) of the pure product. $^1$H NMR (400 MHz, CDCl$_3$): δ 1.36 (1H, s), 5.21 (2H, s), 7.32 (1H, d, J=8.8 Hz), 7.40 (1H, s), 7.45 (2H, d, J=7.6 Hz), 7.86 (2H, d, J=7.2 Hz), 8.09 (1H, d, J=9.2 Hz). LRESI-MS: calculated for [C$_{21}$H$_{22}$BN$_2$O$_3$S]$^+$393.1. found 393.1.

4-((2-cyanobenzo[d]thiazol-6-yloxy)methyl)phenylboronic acid (6)

2-Cyano-6-hydroxybenzothiazole (2) (150 mg, 0.85 mmol, 1.1 equiv.) and 4-(hydroxymethyl)benzeneboronic acid (5) (166 mg, 0.77 mmol, 1 equiv.) were dissolved in 15 mL dry dimethylformamide (DMF) prior to the addition of cesium carbonate (277 mg, 0.85 mmol, 1 equiv.). The mixture was stirred at 60° C. for 45-50 minutes before it was allowed to cool to room temperature. 100 mL EtOAc was added to the reaction mixture, and the organic phase was washed three times with DI H$_2$O. The aqueous layers were combined and washed three times with EtOAc. All of the organic layers were combined, washed twice with brine, dried over sodium sulfate, and concentrated. The crude material was purified on a silica column (90:10 EtOAc:methanol, dry loaded) to give 225 mg (94%) of the pure product. $^1$H NMR (400 MHz, d$_6$-Acetone): δ 5.33 (2H, s), 7.23 (2H, s), 7.45 (1H, dd, J=9.0, 2.6 Hz), 7.52 (2H, d, J=8.0 Hz), 7.93 (3H, m), 8.16 (1H, d, J=8.8 Hz).

6-aminobenzo[d]thiazole-2-carbonitrile (7)

Compound 7 was synthesized according to procedures presented in the literature. (Katz L (1951) Antituberculous compounds: 2-benzalhydrazinobenzothiazoles. *J Am Chem Soc* 73:4007) and (White E H, Worther H, Seliger H H, McElroy W D (1966) Amino analogs of firefly luciferin and biological activity thereof. *J Am Chem Soc* 88:2015).

4-(4,4,5,5-Tetramethyl-1,3,2-dioxaborolan-2-yl)benzyl 2-cyanobenzo[d]thiazol-6-ylcarbamate (9)

A flask containing toluene (3.3 mL) was charged with 7 (55 mg, 0.31 mmol, 1 equiv), DMAP (76 mg, 0.62 mmol, 2 equiv), and triphosgene (93 mg, 0.31 mmol, 1 equiv). The flask was heated at 120° C. for three hours before being cooled to room temperature. Compound 8 (77 mg, 0.33 mmol, 1.05 equiv) and DMAP (38 mg, 0.31 mmol, 1 equiv) were added to the reaction vessel prior to addition of 6 mL dry dichloromethane. The flask was heated to 50° C. for 3 hours before being cooled room temperature. The solvent was removed under vacuum, and the product was purified with flash column chromatography using hexanes:EtOAc (80:20). After purification, 59 mg (43%) of the pure product was obtained. $^1$H NMR (CDCl$_3$, 300 MHz): δ 8.43 (1H, s), 8.08 (1H, d, J=9.0 Hz), 7.82 (2H, d, J=8.1 Hz), 7.39 (2H, d, J=8.1 Hz), 7.33 (1H, dd, J$_1$=9.0 Hz, J$_2$=2.1 Hz), 7.13 (1H, s), 5.24 (2H, s), 1.39 (12H, s). ESI-LC/MSD: calculated for [M$^+$] 435.1. found 434.7.

4-((2-cyanobenzo[d]thiazol-6-ylcarbamoyloxy)methyl)phenylboronic acid (10)

Compound 9 (61 mg, 0.14 mmol, 1 equiv.) was dissolved in N$_2$-sparged tetrahydrofuran (THF, 10 mL) prior to addition of concentrated HCl (0.8 mL) and N$_2$-sparged deionized water (8 mL). The reaction mixture was stirred for one hour prior to the addition of an additional 8 mL DI H$_2$O. After 15 min, the THF was removed under vacuum, and the precipitate that formed was collected via filtration and rinsed with DI H$_2$O. To remove residual starting material, the crude product was precipitated from diethyl ether to yield 49 mg (73%) of a white powder. $^1$H NMR (400 MHz, d$_6$-Acetone): δ 5.27 (2H, s), 7.22 (2H, s), 7.45 (2H, d, J=8.0 Hz), 7.80 (1H, dd, J=9.4, 2.2 Hz), 7.92 (2H, d, J=8.4 Hz), 8.17 (1H, d, J=9.6 Hz), 8.63 (1H, d, J=2.0 Hz).

6-(4,4,5,5-tetramethyl-1,3,2-dioxaborolan-2-yl)benzo[d]thiazole-2-carbonitrile (11)

Compound 11 was synthesized according to previously reported procedures (Akhavan-Tafti H, Eickholt R A, Lauwers K S, Handley R S (2005) Signalling compounds for use in methods of detecting hydrogen peroxide; and U.S. Pat. No. 6,919,463 B2).

(2-cyanobenzo[d]thiazol-6-yl)boronic acid (12)

Compound 11 (50 mg, 0.17 mmol, 1 equiv.) was dissolved in N$_2$-sparged tetrahydrofuran (6 mL) prior to addition of concentrated HCl (0.2 mL) and N$_2$-sparged deionized water (4 mL). The reaction mixture was stirred for one hour prior to the addition of an additional 6 mL DI H$_2$O. After 15 min, the THF was removed under vacuum, and the precipitate that formed was collected via filtration and rinsed with DI H$_2$O. To remove residual starting material, the crude product was dissolved in acetone, which did not dissolve the starting material. The precipitate was filtered off and the filtrate was concentrated to give the product. The product was purified further by washing with a mixture of hexanes and diethyl ether to yield 6.8 mg (20%) of a light yellow powder. $^1$H NMR (400 MHz, d$_6$-Acetone): δ 7.59 (2H, s), 8.21 (2H, m), 8.72 (1H, s).

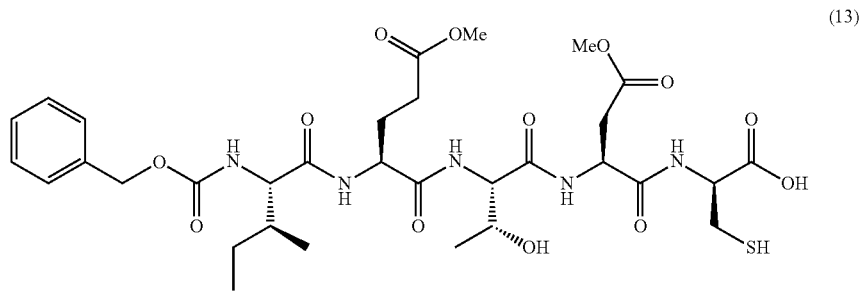 [SMILES: CC[C@H](C)[C@H](NC(=O)OCc1ccccc1)C(=O)N[C@@H](CCC(=O)OC)C(=O)N[C@H](C(=O)N[C@@H](CC(=O)OC)C(=O)N[C@H](CS)C(=O)O)[C@@H](C)O]

Z-Ile-Glu(OMe)-Thr-Asp(OMe)-D-Cys (13)

Compound 13 was prepared by the HHMI Mass Spectrometry Laboratory at the University of California, Berkeley. The compound was purified on a silica column (80:20 cyclohexane:EtOAc—100% EtOAc, then 95:5 Acetone:MeOH) to yield 11.9 mg of the pure product. $^1$H NMR (400 MHz, CD$_3$OD): δ 1.20 (6H, m), 1.55 (3H, m), 1.83 (2H, m), 2.04 (2H, m), 2.20 (2H, m), 2.29 (1H, m), 2.47 (2H, m), 2.85 (1H, m), 2.95 (2H, m), 3.68 (6H, d, J=9.0 Hz), 4.00 (1H, m), 4.23 (1H, m), 4.32 (1H, m), 4.50 (2H, m), 5.12 (2H, s), 7.36 (5H, m). LRESI-MS: calculated for [M]$^+$742.3. found 742.3. HRESI-MS: calculated for [M]$^+$742.29. found 742.29615.

Example 2

Dual Analyte Detection in Mice

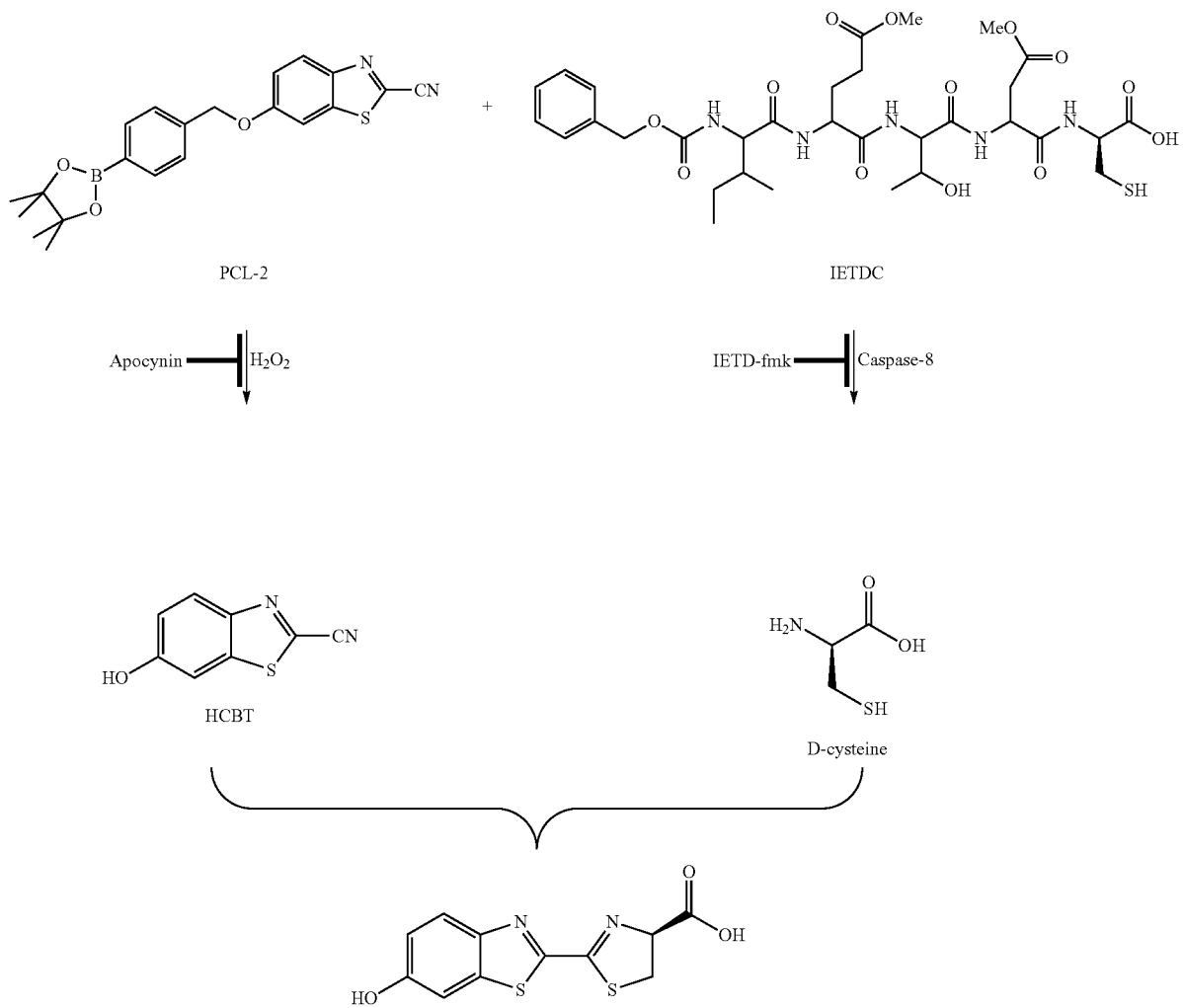

Lipopolysaccharide injections can be used in mice to mimic septic shock, which will result in hydrogen peroxide production and an increase in caspase-8 activity. The hydrogen peroxide can be detected with a protected cyanobenzothiazole and caspase-8 activity can be detected using a short peptide. If both hydrogen peroxide and caspase-8 are present, signal will be produced via the formation of firefly luciferin.

Materials and Methods

Synthetic Materials and Methods.

Scheme 1 shows the synthesis of peroxy caged luciferein-2 (PCL-2, 4-((2-Cyanobenzo[d]thiazol-6-yloxy)methyl)phenylboronic acid):

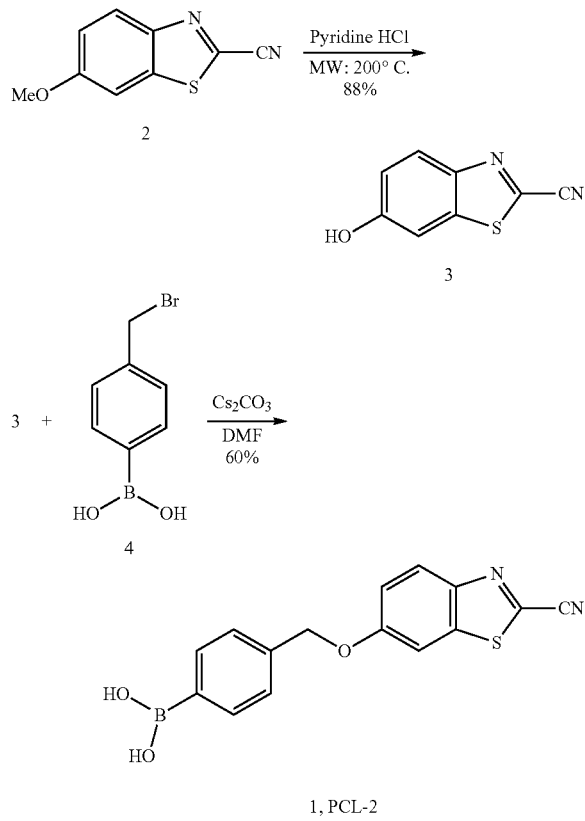

Compound 3 of Scheme 1 was synthesized according to literature procedures. See, e.g., Van de Bittner et al., *Proc. Natl. Acad. Sci. USA* (2010) 107, 21316-21321. Chemicals were purchased from Sigma-Aldrich (St. Louis, Mo.), EMD Chemicals Inc. (Gibbstown, N.J.), Alfa Aesar (Ward Hill, Mass.), and Thermo Fisher Scientific (Waltham, Mass.) and were used as received. Column chromatography was performed using SiliaFlash P60 silica gel (40-63 microns) from Silicycle (Quebec, Canada). Analytical thin layer chromatography was performed using glass-backed $SiO_2$ TLC plates from Silicycle. NMR spectra were obtained in deuterated solvents from Cambridge Isotope Laboratories (Cambridge, Mass.) on a Bruker AV-400 spectrometer at the College of Chemistry NMR Facility at the University of California, Berkeley. All chemical shifts are reported in the standard δ notation of parts per million using the peaks of residual proton and carbon signals of the solvent as internal references. Low resolution Electrospray Ionization (ESI) mass spectral analyses were performed on an Agilent 6100 series single quad LC/MS system or an Agilent 7890A GC system with a 5975C inert MSD with a triple-axis detector.

4-((2-Cyanobenzo[d]thiazol-6-yloxy)methyl)phenylboronic acid (1).

6-Hydroxy-2-cyanobenzothiazole (3) (150 mg, 0.85 mmol, 1.1 equiv) and 4-(hydroxymethyl)benzeneboronic acid (4) (166 mg, 0.77 mmol, 1.0 equiv) were dissolved in 15 mL dry N,N-dimethylformamide (DMF) prior to the addition of cesium carbonate (277 mg, 0.85 mmol, 1.0 equiv). The mixture was stirred at 60° C. for 45-50 min before it was allowed to cool to room temperature. Ethyl acetate (EtOAc, 100 mL) was added to the reaction, and the organic phase was washed with deionized $H_2O$ (3×50 mL). The aqueous layers were combined and back extracted with EtOAc (3×30 mL). All of the organic layers were combined, washed twice with brine, dried over sodium sulfate, and concentrated in vacuo. The crude material was purified on a silica column (90:10 EtOAc:methanol, dry loaded) to give 225 mg (94%) of the pure product as a white powder. $^1$H NMR (400 MHz, $d_6$-Acetone): δ 5.33 (2H, s), 7.23 (2H, s), 7.45 (1H, dd, J=9.0, 2.6 Hz), 7.52 (2H, d, J=8.0 Hz), 7.91-7.94 (3H, m), 8.16 (1H, d, J=8.8 Hz). LRMS (m/z): $[M]^+$ calcd. for $C_{15}H_{12}BN_2O_3S$, 311.1. found, 311.1.

Kinetic Analysis.

$H_2O_2$ (1, 2.5, or 5 mM) was added to PCL-2 (10 μM) in Tris buffer (pH 8.5) and absorbance measurements were recorded every 15-30 seconds over 5-20 minutes to determine the second order rate constant for the reaction. Measurements were taken at pH 8.5 to distinguish the HCBT peak, which shifts from 321 nm to 379 nm when it is deprotonated, from the PCL-2 peak (321 nm).

Bioluminescent Assays.

Millipore water was used to prepare all aqueous solutions. Luciferase (100 μg/mL) in 50 mM Tris buffer, pH 7.4, with 10 mM $MgCl_2$, 0.1 mM $ZnCl_2$, and 2 mM ATP was added to selectivity assay samples (described below) to determine the relative amount of luciferin formed during incubation. Measurements for bioluminescent assays were performed at 37° C. and were recorded using a Molecular Devices SpectraMax M2 plate reader (Sunnyvale, Calif.). Samples for bioluminescent measurements were placed in white, opaque 96-well plates, which were purchased from Corning Inc. (Corning, N.Y.). ATP was purchased from MP Biomedicals (Solon, Ohio) or Sigma-Aldrich (St. Louis, Mo.), and luciferase was purchased from Promega (Madison, Wis.). Caspase enzymes were purchased from Sigma-Aldrich (St. Louis, Mo.), and caspase inhibitors were purchased from MP Biomedicals (Solon, Ohio).

Standard Curve for Luciferin Bioluminescence.

Luciferin (0.5-10 μM) was incubated in 100 μL Tris buffer (50 mM, pH 7.4) for 60 min prior to addition of 100 μL of a Tris buffer (50 mM, pH 7.4) containing luciferase (100 μg/mL), 10 mM $MgCl_2$, 0.1 mM $ZnCl_2$, and 2 mM ATP. Following addition of the luciferase-containing solution the bioluminescent signal was detected.

In Situ Luciferin Formation from HCBT and D-Cysteine.

HCBT (2.5-25 μM) was incubated with D-cysteine (2.5-25 μM) in 100 μL Tris buffer (50 mM, pH 7.4) for 60 min prior to addition of 100 μL of a Tris buffer (50 mM, pH 7.4) containing luciferase (100 μg/mL), 10 mM $MgCl_2$, 0.1 mM $ZnCl_2$, and 2 mM ATP. Following addition of the luciferase-containing solution the bioluminescent signal was detected.

Selectivity Assays for PCL-2.

Various ROS (100 μM) were administered to PCL-2 or HCBT (5 μM) in Tris buffer (50 mM, pH 7.4) with or without 10 mM $MgCl_2$ and 0.1 mM $ZnCl_2$. Hydrogen peroxide ($H_2O_2$), tert-butyl hydroperoxide (TBHP), and hypochlorite ($^-$OCl) were delivered from 10 mM stock solutions prepared using 30%, 70%, and 6.15% aqueous solutions, respectively. Hydroxyl radical (.OH) and tert-butoxy radical (.OtBu) were generated by reaction of 1 mM $FeCl_2$ with 100 μM $H_2O_2$ or TBHP, respectively. Nitric oxide (NO.) was delivered using PROLI NONOate, and superoxide ($O_2^-$) was delivered from a 10 mM stock solution of $KO_2$ in DMSO. Experiments with $H_2O_2$ and catalase were performed with 100 μM $H_2O_2$ and 0.4 mg/mL catalase. After each ROS was incubated with PCL-2 for 5, 20, 40, or 60 min or HCBT for 60 min, dithiothreitol (1 mM) and D-cysteine (20 μM) were added. For solutions with $Fe^{2+}$, EDTA (1 mM) was added prior to D-cysteine to chelate the iron. After an additional 15 min incubation, 100 μL of a Tris buffer (50 mM, pH 7.4) containing luciferase (100 μg/mL), 10 mM $MgCl_2$, 0.1 mM $ZnCl_2$, and 2 mM ATP was added to 100 μL of the PCL-2 or HCBT solutions and the bioluminescent signal was detected.

Concentration Dependence of PCL-2.

PCL-2 was incubated in Tris buffer (50 mM, pH 7.4) with various concentrations of $H_2O_2$ for 60 min prior to the addition of catalase (0.4 mg/mL), dithiothreitol (1 mM) and D-cysteine (20 μM). After an additional 15 min incubation, 100 μL of a Tris buffer (50 mM, pH 7.4) containing luciferase (100 μg/mL), 10 mM $MgCl_2$, 0.1 mM $ZnCl_2$, and 2 mM ATP was added to 100 μL of the PCL-2 solutions and the bioluminescent signal was detected.

Selectivity Assays for IETDC (Carboxylic Acid).

For determination of caspase selectivity, various caspases (3 and 8:1 unit, 9:0.001 unit) were administered to IETDC or D-cysteine (5 μM) in Tris buffer (50 mM, pH 7.4). A caspase buffer (10% sucrose containing 20 mM Tris-HCl, 150 mM imidazole-HCl, 20 mM 2-mercaptoethanol, 500 mM NaCl, 2.5 mM EDTA, and 0.1% CHAPS, pH 8.0) was also added with the caspase enzymes to a total volume (enzyme+buffer) of 5 μL. Additionally, dithiothreitol (1 mM) and HCBT (5 μM) were added to each solution for luciferin formation. For experiments with caspase inhibition, a pan-caspase inhibitor, Q-VD-OPh (10 μM), was added to the Tris buffer and incubated with caspase 8 for 15 min prior to delivery of IETDC, DTT, and HCBT. After each enzyme was incubated with IETDC or D-cysteine for 60 min, 100 μL of a Tris buffer (50 mM, pH 7.4) containing luciferase (100 μg/mL), 10 mM $MgCl_2$, 0.1 mM $ZnCl_2$, and 2 mM ATP was added to 100 μL of the IETDC or D-cysteine solutions and the bioluminescent signal was detected.

Selectivity Assays for Dual $H_2O_2$ and Caspase 8 Detection.

To demonstrate dual imaging of $H_2O_2$ and caspase 8 in vitro, $H_2O_2$ (250 μM) was first added to a solution of PCL-2 (10 μM) or HCBT (5 μM) in Tris buffer (50 mM). To quench $H_2O_2$ immediately, catalase (1 unit) was subsequently added to some of the solutions. After 60 min, catalase (1 unit) was added to all other solutions containing $H_2O_2$ to quench any remaining $H_2O_2$. Subsequently, caspase 8 (1 unit) was added to the solutions in the presence or absence of the caspase inhibitor, Q-VD-OPh (10 μM), 15 min prior to IETDC (10 μM) or D-cysteine (5 μM) addition. Following IETDC or D-cysteine addition, the solutions were incubated for 60 min. Additionally, dithiothreitol (1 mM) was added to all solutions at the time of caspase 8 addition to maintain the reduced state of the D-cysteine. To monitor luciferin formation, 100 μL of a Tris buffer (50 mM, pH 7.4) containing luciferase (100 μg/mL), 10 mM $MgCl_2$, 0.1 mM $ZnCl_2$, and 2 mM ATP was added to 100 μL of the PCL-2/IETDC or HCBT/D-cysteine solutions and the bioluminescent signal was detected.

Cellular Assays.

A Xenogen IVIS Spectrum instrument (Caliper Life Sciences, Hopkinton, Mass.) was used for bioluminescent imaging in all cellular experiments. PC3M-luc cells (kindly provided by Chris Contag, Stanford University) were cultured in Dulbecco's Modified Eagle Medium (DMEM) containing 10% Fetal Bovine Serum (FBS). Prior to assaying, cells were passed and plated (1.3-1.5×10$^4$ cells/well) in black 96-well plates with clear bottoms (Becton Dickinson and Company, Franklin Lakes, N.J.). Once the cells were ca. 95% confluent, reagents were added for bioluminescent assays.

Comparison of In Situ Luciferin Formation and Luciferin in PC3M-luc Cells.

PC3M-luc cells prepared as described above were washed with HBSS (25 mM glucose) prior to addition of HCBT and D-cysteine (0-500 μM, 1% DMSO) or luciferin (0-500 μM, 1% DMSO) in HBSS (25 mM glucose). For experiments with lysed cells, 100 μL Glo lysis buffer (Promega, Madison, Wis.) was incubated with the PC3M-luc cells for 5 min prior to addition of HCBT and D-cysteine or luciferin. The plates were immediately imaged for 2 h to determine the peak bioluminescent signal produced.

Determination of Signal Produced from Endogenous L-Cysteine in PC3M-luc Cells.

PC3M-luc cells prepared as described above were washed with HBSS (25 mM glucose) prior to addition of HCBT and D-cysteine (0-50 μM, 1% DMSO) or HCBT alone (0-50 μM, 1% DMSO) in HBSS (25 mM glucose). The plate was immediately imaged for 2 h to determine the peak bioluminescent signal produced.

Lifetime of HCBT and D-Cysteine in PC3M-luc Cells.

The medium was removed from PC3M-luc cells prepared as described above, and HCBT (100 μM, 1% DMSO) or D-cysteine (100 μM, 1% PBS) in DMEM (-FBS) was added. After a 30 min incubation, the HCBT or D-cysteine was removed, the cells were washed with DMEM (-FBS), and fresh DMEM was added. After 0, 15, 30, 45, or 60 min, the second component of luciferin, D-cysteine (100 μM final concentration, 1% PBS) or HCBT (100 μM final concentration, 1% DMSO) in HBSS (25 mM glucose) was added, and the plate was immediately imaged for 2 h to determine the peak bioluminescent signal produced.

Concentration Dependence of PCL-2 with PC3M-luc Cells.

The medium was removed from PC3M-luc cells prepared as described above, and PCL-2 (25 μM, 2.5% final DMSO concentration), D-cysteine (25 μM), and $H_2O_2$ (0-100 μM final concentrations) in DMEM (-FBS) were added. The plate was immediately imaged for 2 h to determine the peak bioluminescent signal produced from PCL-2.

Animal Experiments.

A Xenogen IVIS Spectrum instrument (Caliper Life Sciences, Hopkinton, Mass.) was used for bioluminescent imaging in all animal experiments. Mice were anesthetized prior to injection and during imaging via inhalation of isoflurane. Phosphate Buffered Saline (PBS) was purchased from Thermo Fisher Scientific (Waltham, Mass.), and saline (0.9%) was made from sodium chloride and Millipore water. Isoflurane was purchased from Phoenix Pharmaceuticals, Inc. (St. Joseph, Mo.), and pharmaceutical grade DMSO was purchased from Sigma-Aldrich (St. Louis, Mo.). Medical grade oxygen was purchased from Praxair (Danbury, Conn.).

Animals.

FVB-luc$^+$ (FVB-Tg(CAG-luc,-GFP)L2G85Chco/J) mice were bred at UC Berkeley, and were single or group-housed on a 12:12 light-dark cycle at 22° C. with free access to food and water. All studies were approved and performed according to the guidelines of the Animal Care and Use Committee of the University of California, Berkeley.

Comparison of In Situ Luciferin Formation and Luciferin in Mice.

Unshaven, male FVB-luc$^+$ mice were anesthetized with isoflurane and injected IP with D-cysteine (0.05 or 0.5 μmol, in 20 μL of PBS) or vehicle (20 μL PBS). After 2 min, mice were injected IP with HCBT (0.05 or 0.5 μmol in 50 μL of 1:1 DMSO:PBS) or luciferin (0.05 μmol in 50 μL of 1:1 DMSO:PBS). Following injections, mice were imaged with an IVIS Spectrum.

Determination of Signal Produced from Endogenous L-Cysteine in Mice.

Unshaven, male FVB-luc+ mice were anesthetized with isoflurane and injected IP with D-cysteine (0.05 µmol, in 20 µL of PBS) or vehicle (20 µL PBS). After 2 min, mice were injected IP with HCBT (0.05 µmol in 50 µL of 1:1 DMSO:PBS). Following injections, mice were imaged with an IVIS Spectrum.

Exogenous $H_2O_2$ Experiments in Mice.

Unshaven, male FVB-luc$^+$ mice were anesthetized with isoflurane and injected IP with a mixture of PCL-2 and D-cysteine (0.05 µmol each, in 50 µL of 1:1 DMSO:PBS), followed immediately by an IP injection of $H_2O_2$ (0-4.5 µmol in 100 µL of PBS). Control mice were injected IP with a mixture of HCBT and D-cysteine (0.01 µmol each, in 50 µL of 1:1 DMSO:PBS) immediately prior to $H_2O_2$ (4.5 µmol in 100 µL of PBS). Following injections, mice were imaged with an IVIS Spectrum.

Antioxidant Experiments in Mice.

Unshaven, male FVB-luc$^+$ mice, were anesthetized with isoflurane and injected IP with NAC (10 mg/kg in 25 µL of PBS, pH 7-8) or PBS (25 µL). After 2 min, the mice were injected IP with a mixture of PCL-2 and D-cysteine (0.05 µmol each, in 50 µL of 1:1 DMSO:PBS) immediately prior to IP injection of $H_2O_2$ (1.5 µmol in 75 µL of PBS). Firefly luciferin control mice were injected IP with NAC (10 mg/kg in 100 µL of PBS, pH 7-8) or PBS (100 µL) immediately following IP injection of a mixture of HCBT and D-cysteine (0.01 µmol each, in 50 µL of 1:1 DMSO:PBS). Following injections, mice were imaged with an IVIS Spectrum.

Lipopolysaccharide Inflammation Model.

Unshaven, female FVB-luc$^+$ mice, aged 2-5 months, were anesthetized with isoflurane and injected IP with lipopolysaccharides (LPS, 3 mg/kg in 50 µL of saline) or saline (50 µL). For studies with PCL-2 alone, mice were injected IP with either apocynin (10 mg/kg in 20 µL of DMSO) or DMSO (20 µL) 6 h after LPS injection. Two minutes after this injection, mice were injected IP with a mixture of PCL-2 and D-cysteine (0.05 µmol each, in 50 µL of 1:1 DMSO:PBS) and imaged. For studies with IETDC alone, mice were injected IP with either z-VD(OMe)-OPh (1 µmol in 20 µL of DMSO) or DMSO (20 µL) 5.5 h after LPS injection. Thirty minutes after z-VD(OMe)-OPh or vehicle injection, mice were injected IP with a mixture of IETDC and HCBT (0.05 µmol each, in 50 µL of 1:1 DMSO:PBS) and imaged.

For studies with PCL-2 and IETDC, mice were injected IP with ascorbic acid (200 mg/kg in 30 µL of saline) or the saline vehicle (30 µL) 30 min prior to IP injection of LPS (3 mg/kg in 50 µL of saline) or saline (50 µL). Two hours after injection of LPS, z-VD(OMe)-OPh (1 µmol in 20 µL of DMSO) or the vehicle, DMSO (20 µL), was injected IP. Two hours later, mice were injected IP with a mixture of PCL-2 and IETDC (0.05 µmol each, in 50 µL of 7:3 DMSO:PBS) and imaged.

Results and Discussion

Characterization of In Situ Luciferin Formation.

Figure 1:
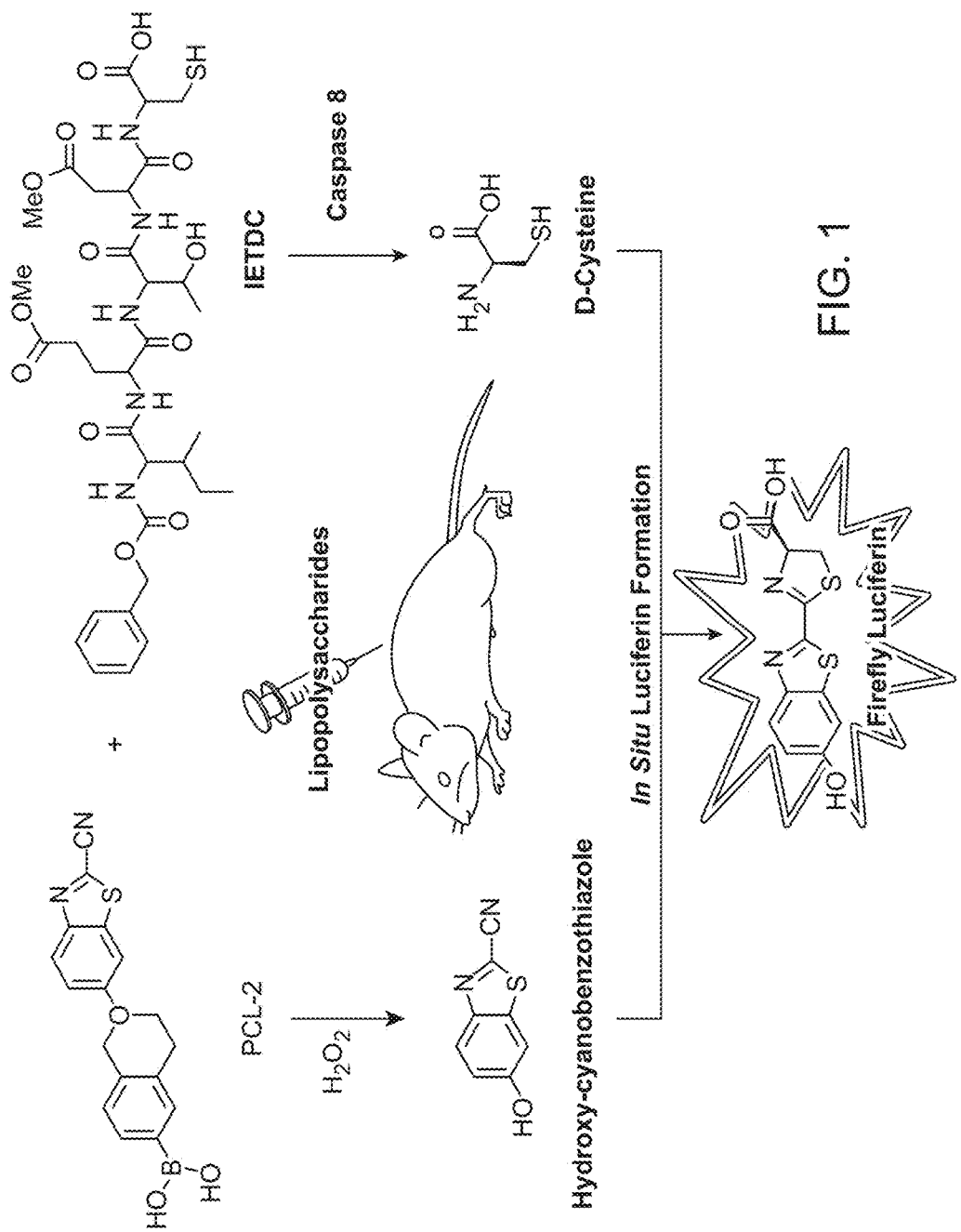
FIG. 1 depicts a design strategy for simultaneous detection of $H_2O_2$ and caspase 8 activity through release of HCBT and D-cysteine and in situ formation of firefly luciferin.
Figure 2:
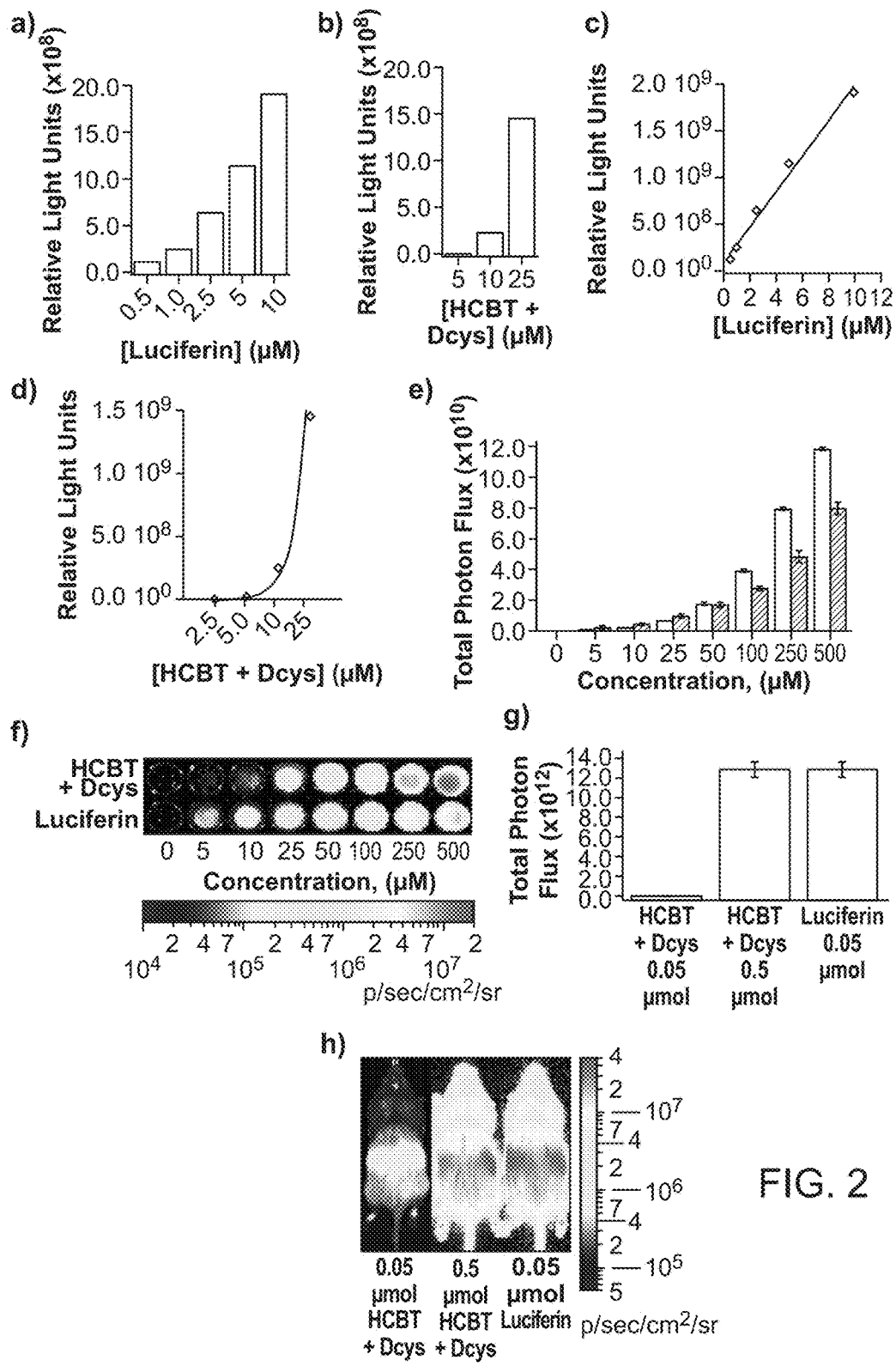
FIG. 2 depicts a comparison of HCBT/D-cysteine and luciferin. (a) Total bioluminescent signal, integrated over 45 min, from luciferin (0.5-10 μM). (b) Total bioluminescent signal, integrated over 45 min, from HCBT and D-cysteine (5-25 μM, each) following incubation for 1 h in Tris buffer (50 mM, pH 7.4). To measure luciferin formation in a and b, 100 μg/mL luciferase in 50 mM Tris buffer with 10 mM $MgCl_2$, 0.1 mM $ZnCl_2$, and 2 mM ATP (pH 7.4) was added to the luciferin and HCBT/D-cysteine solutions. (c) Line graph representation of a, which indicates a linear increase ($R^2=0.9864$) in bioluminescent signal from luciferin (0.5-10 μM). (d) Line graph representation of b, which indicates an exponential increase ($R^2=0.9889$) in bioluminescent signal from HCBT and D-cysteine (2.5-25 μM, each). (e) Total photon flux, integrated over 2 h, from PC3M-luc cells with HCBT and D-cysteine (0-500 μM, dark grey bars) or luciferin (0-500 μM, light grey bars) in HBSS (25 mM glucose). (f) Representative image of PC3M-luc cells with HCBT and D-cysteine or luciferin, log scale. (g) Total photon flux, 0-60 min post-injection, for mice injected with HCBT and D-cysteine (0.05 or 0.5 μM, each) or luciferin (0.05 μM). (h) Representative image (30 min post-injection) of mice injected with HCBT and D-cysteine or luciferin, log scale. Error bars are ±SEM; E: n=3, G: n=3-4.
Figure 3:
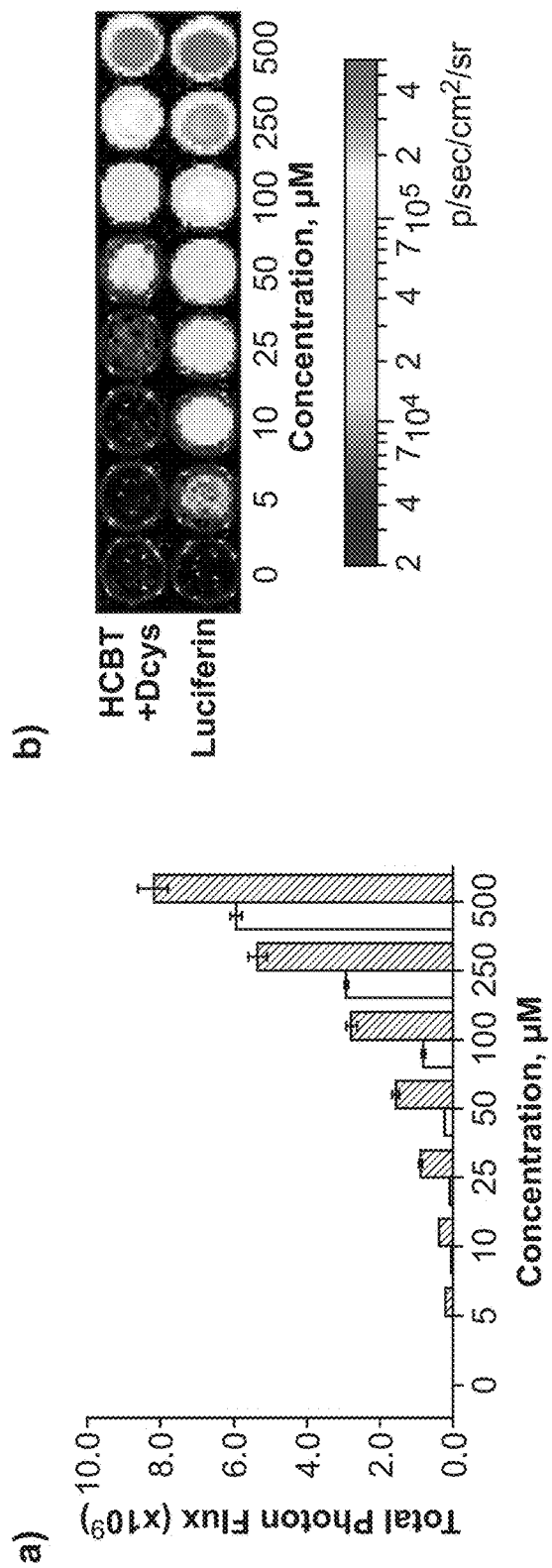
FIG. 3 shows a comparison of HCBT/D-cysteine and luciferin in lysed PC3M-luc cells. (a) Total photon flux, integrated over 2 h, from lysed PC3M-luc cells with HCBT and D-cysteine (0-500 μM, dark grey bars) or luciferin (0-500 μM, light grey bars) in HBSS (25 mM glucose). (b) Representative image of lysed PC3M-luc cells with HCBT and D-cysteine or luciferin. Error bars are ±SEM.

To determine the utility of the in situ luciferin formation approach for dual-analyte imaging a comparison of the signals from HCBT/D-cysteine to luciferin was made, the effect of endogenous L-cysteine was determined, and the lifetime of the complementary HCBT and D-cysteine partner molecules in cells was analyzed. First, an in vitro test comparing the bioluminescent signal produced by luciferin to that produced by a mixture of HCBT and D-cysteine (FIG. 2$a,b$) was completed. A linear regression analysis of the data indicates a linear fit ($R^2$=0.9864) for luciferin, while HCBT/D-cysteine has an exponential fit ($R^2$=0.9889), which is indicative of the second-order reaction between HCBT and D-cysteine for luciferin formation. Using the luciferin standard curve (FIG. 2$a$), it was determined that 25 µM HCBT/D-cysteine produces ca. 6.7 µM luciferin, a 27% yield, in vitro. Subsequent determination of in situ luciferin formation in PC3M-luc cells indicated that at lower concentrations exogenous luciferin produces a greater signal than HCBT/D-cysteine (FIG. 2$e,f$). However, at higher concentrations, HCBT/D-cysteine produced a greater signal than luciferin. As HCBT and D-cysteine were not able to produce more luciferin, and thus bioluminescent signal, than equivalent concentrations of luciferin, a determination was made as to whether the greater HCBT/D-cysteine signal was due to differences in cell-membrane permeability. Indeed, when the same comparison of HCBT/D-cysteine and luciferin was completed following cell lysis (FIG. 3), the signal from HCBT/D-cysteine approached, but did not surpass, the luciferin signal at high concentrations, indicating that the greater signal from HCBT/D-cysteine detected within intact, living cells is due to an increased permeability of HCBT and D-cysteine across the cell membrane compared to the full luciferin substrate. A final experiment comparing HCBT/D-cysteine in FVB-luc$^+$ mice (Cao et al., Proc. Natl. Acad. Sci. USA (2004) 101, 221-226), which ubiquitously express firefly luciferase, indicated that 0.05 µmol luciferin produces a ca. 40-fold brighter signal than 0.05 µmol HCBT/D-cysteine, however, a 10-fold increase in HCBT/D-cysteine results in a bioluminescent signal that is equivalent to the 0.05 µmol luciferin signal.

Figure 4:
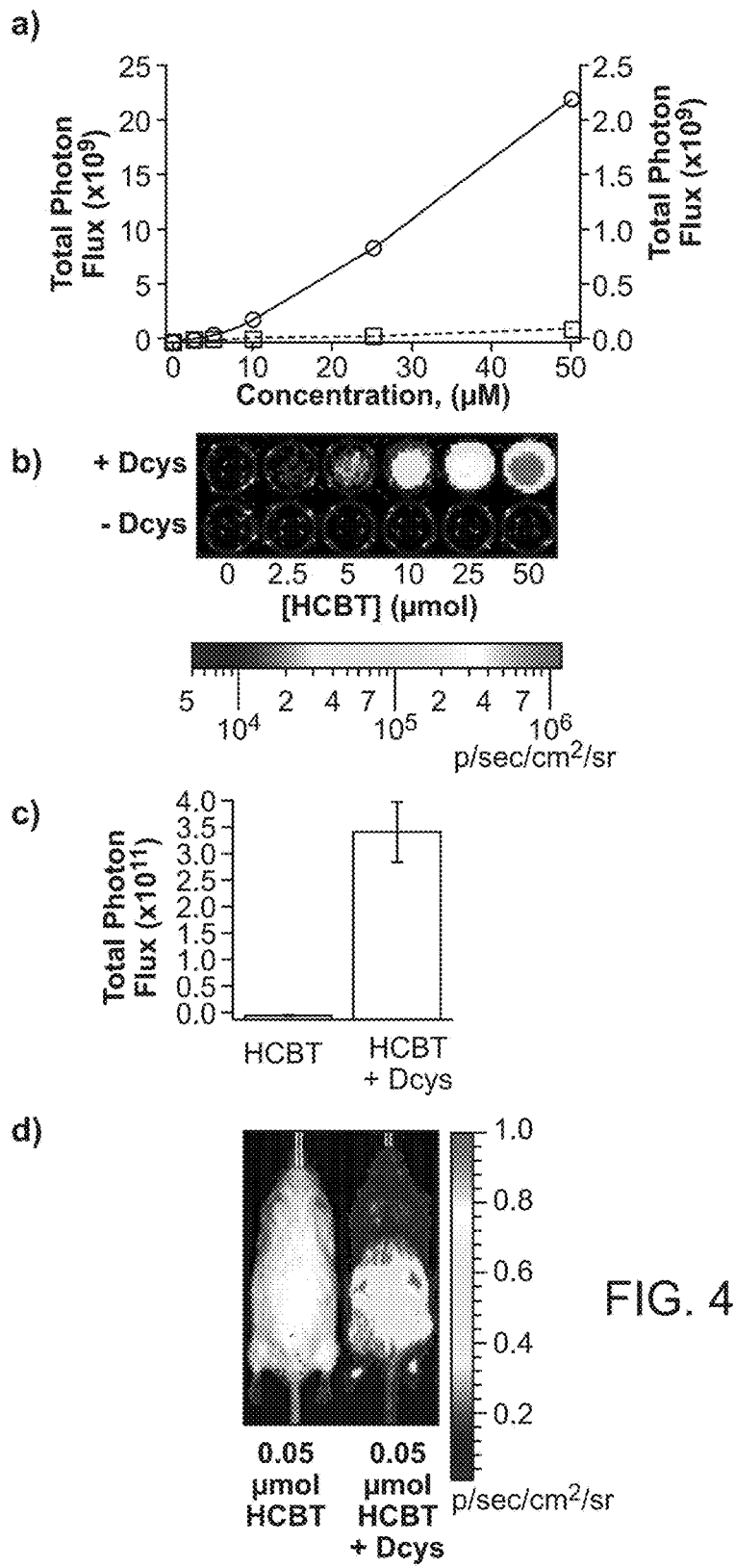
FIG. 4 depicts a determination of bioluminescent signal from endogenous L-cysteine. (a) Total photon flux, integrated over 2 h, from PC3M-luc cells with HCBT (0-50 μM) in the presence (solid line, y1 axis) or absence (dashed line, y2 axis) of D-cysteine (0-50 μM) in HBSS (25 mM glucose). (b) Representative image of PC3M-luc cells with HCBT±D-cysteine, log scale. (c) Total photon flux, 0-60 min post-injection, for mice injected with D-cysteine (0.05 μmol in 20 μL PBS) or vehicle (20 μL PBS) and HCBT (0.05 μM in 50 μL 1:1 DMSO:PBS). (d) Representative image (30 min post-injection) of mice injected with HCBT±D-cysteine. Error bars are ±SEM; A: n=3, C: n=3-4.

Next, the effect of endogenous L-cysteine on the signal from HCBT was determined. Initial experiments in PC3M-luc cells indicated a negligible production of bioluminescence from HCBT and endogenous L-cysteine compared to the signal obtained from mixing HCBT and D-cysteine (FIG. 4$a,b$). Analogous studies in FVB-luc$^+$ mice gave the same result, as the bioluminescent signal from the condensation of HCBT and endogenous L-cysteine was negligible compared to the signal produced when D-cysteine is present (FIG. 4$c,d$).

Figure 5:
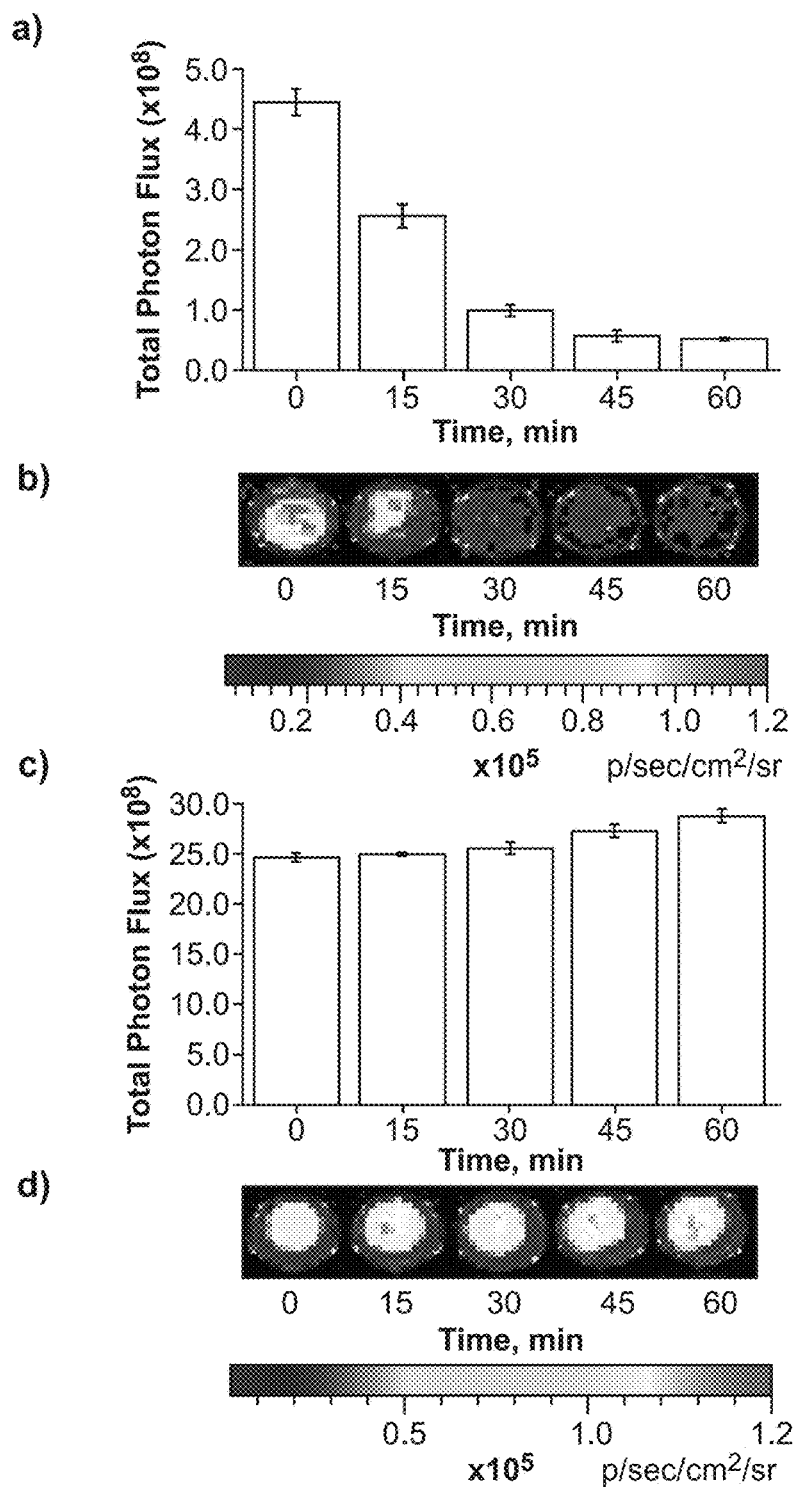
FIG. 5 depicts a determination of the lifetime of HCBT and D-cysteine in PC3M-luc cells. (a) Total photon flux, integrated over 2 h, from PC3M-luc cells with D-cysteine (100 μM) added 0, 15, 30, 45, or 60 min after incubation with HCBT (100 μM). (b) Representative image of PC3M-luc cells with D-cysteine added 0, 15, 30, 45, or 60 min following removal of HCBT. (c) Total photon flux, integrated over 2 h, from PC3M-luc cells with HCBT (100 μM) added 0, 15, 30, 45, or 60 min after incubation with D-cysteine (100 μM). (d) Representative image of PC3M-luc cells with HCBT added 0, 15, 30, 45, or 60 min following removal of D-cysteine. Error bars are ±SEM; A and C: n=3.

Finally, to determine the length of time that released HCBT and D-cysteine are available for reaction with their complementary luciferin-forming reagent, cellular lifetime experiments were completed. Specifically, PC3M-luc cells were first incubated with HCBT or D-cysteine for 30 min, then the cells were washed, and then the complementary luciferin-forming reagent was added after 0, 15, 30, 45, or 60 min. For the HCBT lifetime studies, it was observed that as the time between removal of HBCT and addition of D-cysteine increased, there was a decrease in luminescence (FIG. 5$a,b$). In contrast to HCBT, D-cysteine was still fully available for reaction with HCBT even an hour after the cells have been washed (FIG. 5$c,d$), indicating that D-cysteine has a long lifetime in cells. Notably, this feature could be used for studying healthy and disease states in which one analyte is produced prior to the second analyte. Taken together, these analyses illuminate the robust in situ luciferin formation of HCBT and D-cysteine, the negligible impact of endogenous L-cysteine, and the cellular availability of HCBT and D-cysteine for dual-analyte detection.

Peroxide Reactivity and Selectivity of PCL-2.

Figure 6:
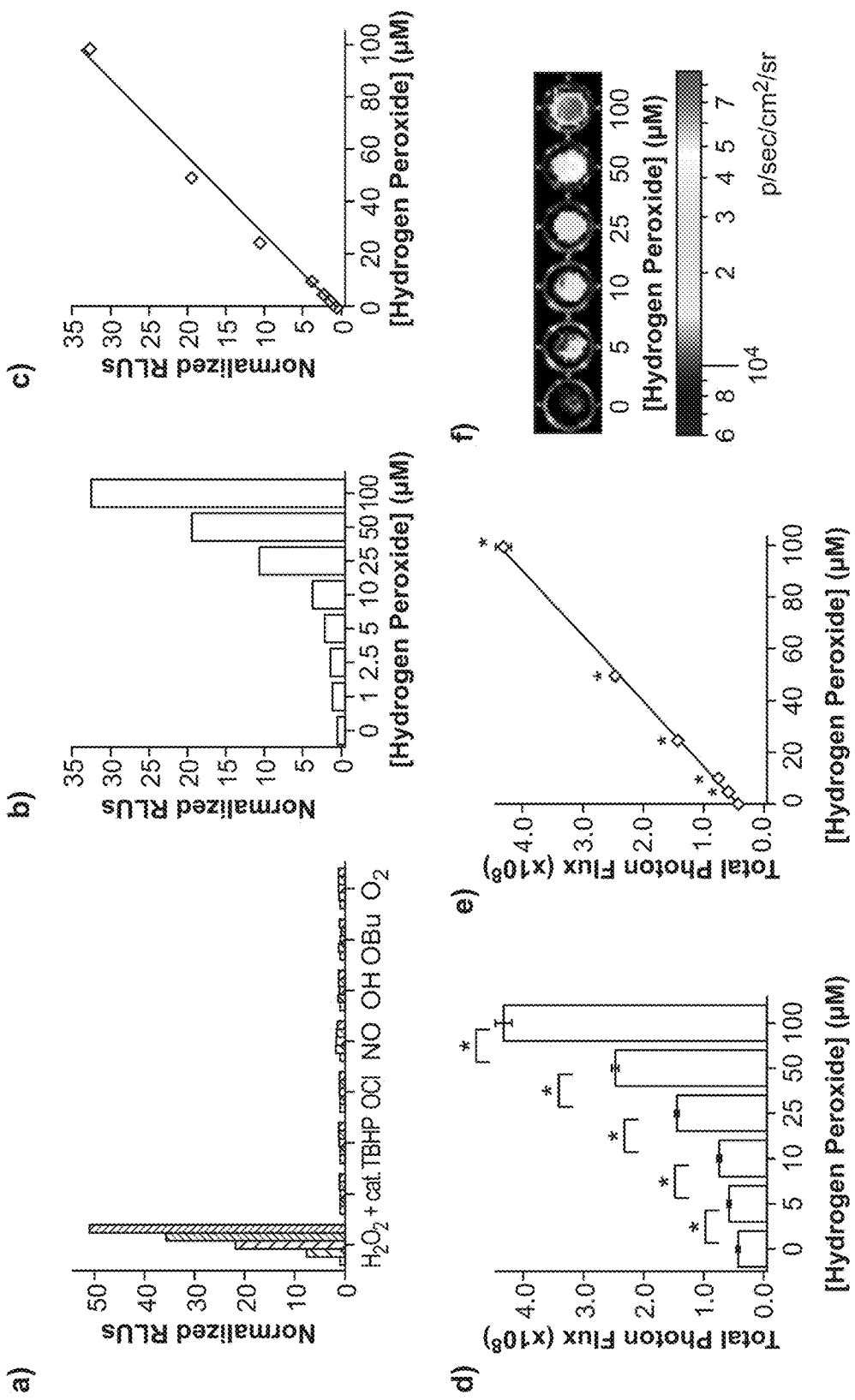
FIG. 6 shows the selective and concentration-dependent bioluminescent detection of $H_2O_2$ by PCL-2. (a) Total bioluminescent signal, integrated over 10 min, from PCL-2 (5 μM) alone (light grey bars) or incubated with various ROS (100 μM) or $H_2O_2$ (100 μM) and catalase (0.4 mg/mL) for 5, 20, 40, or 60 min. Signals normalized to signal from PCL-2 in the absence of any ROS. (b) Total bioluminescent signal, integrated over 15 min, from 5 μM PCL-2 incubated for 1 h with increasing concentrations of $H_2O_2$ (0-100 μM). To measure HCBT release in a and b, PCL-2/ROS solutions were incubated with D-cysteine (20 μM) for 15 min, prior to addition of 100 μg/mL luciferase in 50 mM Tris buffer with 10 mM $MgCl_2$, 0.1 mM $ZnCl_2$, and 2 mM ATP (pH 7.4). (c) Line graph representation of b, which indicates a linear increase ($R^2=0.9957$) in bioluminescent signal from PCL-2 in the presence of $H_2O_2$ in aqueous solution. (d) Total photon flux, integrated over 2 h, from PC3M-luc cells with PCL-2 (25 μM), D-cysteine (25 μM), and $H_2O_2$ (0-100 μM) in DMEM. (e) Line graph representation of d, which indicates a linear increase ($R^2=0.9993$) in bioluminescent signal from PCL-2 in the presence of $H_2O_2$ in PC3M-luc cells. (f)

Determination of the ROS selectivity of PCL-2 for $H_2O_2$, the kinetics of the deprotection reaction, and the concentration dependence of the response of PCL-2 to $H_2O_2$ was made. Reaction of PCL-2 with a panel of biologically relevant ROS for 5-60 min, followed by incubation with D-cysteine for in situ luciferin formation and addition of firefly luciferase, triggered a ca. 50-fold increase in bioluminescence in the presence of $H_2O_2$, with negligible response to other ROS (FIG. 6$a$). Furthermore, in the presence of catalase, a selective $H_2O_2$-scavenging enzyme, the turn-on bioluminescent signal produced in the presence of $H_2O_2$ was attenuated (FIG. 6$a$), thus verifying a robust and selective response to $H_2O_2$. In addition, when the control compound HCBT was incubated with the same panel of ROS, no bioluminescence turn-on was detected (FIG. 7), confirming that the response of PCL-2 to $H_2O_2$ is dependent on reaction at the boronate switch.

Next, the kinetics and dose-dependence of the PCL-2 and $H_2O_2$ reaction was analyzed. A comparison of the measured second-order rate constant ($k=2.7$ $M^{-1}$ $s^{-1}$, FIG. 8) for the PCL-2 and $H_2O_2$ reaction to the catalytic constant ($k_{cat}=1.6$ $s^{-1}$) for firefly luciferase (Branchini et al., *Biochemistry* (1999) 38, 13223-13230) indicated that release of HCBT from PCL-2 is rate-limiting at the µM concentrations used in the studies. The dose-dependence of the response of PCL-2 to $H_2O_2$ was then determined via incubation of PCL-2 with various concentrations of $H_2O_2$ (0-100 µM) for 60 min, prior to incubation with D-cysteine and addition of firefly luciferase. As shown in FIGS. 6b and c, PCL-2 showed a linear response ($R^2=0.9957$) to $H_2O_2$ over two orders of magnitude, from 1-100 µM $H_2O_2$. Furthermore, this same response was found in cellulo when PCL-2 (25 µM), D-cysteine (25 µM), and $H_2O_2$ (0-100 µM) were added to PC3M-luc cells stably transfected with firefly luciferase. Determination of the resultant bioluminescent signal with a sensitive charge coupled device (CCD) camera again indicated a linear response ($R^2=0.9993$) to $H_2O_2$ over two orders of magnitude, from 0-100 µM $H_2O_2$ (FIG. 6d-f). Taken together, the selective response of PCL-2 to $H_2O_2$, as well as its dose-dependent turn-on, low micromolar detection limit, and ability to form luciferin in situ showed that PCL-2 possesses the requisite features for useful in vivo detection of alterations in $H_2O_2$ levels in living organisms.

Selective Cleavage of IETDC by Caspase 8.

After determining the selectivity and sensitivity of PCL-2 for turn-on bioluminescent $H_2O_2$ detection, the ability of caspase 8 to cleave IETDC and release D-cysteine for in situ luciferin formation was evaluated. This goal was accomplished via incubation of IETDC with caspase 8 for 60 min in the presence of HCBT. After subsequent addition of firefly luciferase, the bioluminescent signal was determined, indicating a ca. 27-fold turn-on response (FIG. 9). Addition of a broad-spectrum caspase inhibitor, Q-VD-OPh, (see, e.g., Caserta et al., *Apoptosis* (2003) 8, 345-352; and Cai et al., *Bioorg. Med. Chem. Lett.* (2004) 14, 5295-5300) showed complete attenuation of the response of IETDC to caspase 8, and incubation with other caspase enzyme isoforms that are important for the inflammatory caspase cascade, caspase 3 and caspase 9 (see, e.g., Hotchkiss et al., *Nat. Rev. Immunol.* (2006) 6, 813-822), did not give rise to a turn-on bioluminescent response for the peptide probe (FIG. 9). These latter control experiments verified the chemoselectivity of the IETDC probe for caspase 8 detection. Finally, incubation of D-cysteine with these caspase enzymes caused no change in bioluminescent signal (FIG. 10), further indicating that the response seen with the IETDC luciferin precursor probe was caspase 8-dependent.

Dual Detection of $H_2O_2$ and Caspase 8 Activity via In Situ Luciferin Formation.

To establish the ability of our probes for dual imaging of $H_2O_2$ and caspase 8 activity, PCL-2 with $H_2O_2$ were co-incubated, followed by addition of caspase 8 and IETDC. The resultant bioluminescent signal indicated that in the presence of these two analytes, both probes are deprotected, and luciferin is readily formed to produce a ca. 18-fold increase in bioluminescent signal (FIG. 11). Notably, addition of a single analyte, either $H_2O_2$ or caspase 8, resulted in little to no increase in bioluminescent signal, verifying that the system acts as an AND-type molecular logic gate by requiring the presence of both analytes for bioluminescent signal production. Moreover, treatment with either a $H_2O_2$ scavenger, catalase, or a caspase inhibitor, Q-VD-OPh, attenuated the increase in signal observed in the presence of $H_2O_2$ and caspase 8, further demonstrating that both probes must be uncaged for luciferin formation and bioluminescent signal production (FIG. 11). As expected, treatment with both inhibitors caused a complete attenuation of signal, providing additional validation for the use of PCL-2 and IETDC for dual-analyte detection. Finally, several additional sets of control experiments were performed before moving on to in vivo imaging experiments. First, in contrast to the turn-on response of the dual-probe system in the presence of both $H_2O_2$ and caspase 8, incubation of HCBT and D-cysteine with $H_2O_2$ and caspase 8 caused no alteration of the bioluminescent signal (FIG. 12). Also, addition of catalase and Q-VD-OPh did not interfere with in situ luciferin formation or the resultant bioluminescent signal (FIG. 12). Taken together, the tandem use of PCL-2 and IETDC for dual-analyte imaging in vitro provides an example of a method for detection of two different analytes through production of a single bioluminescent signal.

Molecular Imaging of $H_2O_2$ Fluxes in Living FVB-luc$^+$ Mice with PCL-2.

Following the in vitro demonstration of the utility of PCL-2 and IETDC for dual-analyte imaging, it was next sought to apply PCL-2 to molecular imaging of $H_2O_2$ fluxes in FVB-luc$^+$ mice that ubiquitously express firefly luciferase. See, e.g., Cao et al., *Proc. Natl. Acad. Sci. USA* (2004) 101, 221-226. For the initial in vivo studies, several doses of $H_2O_2$ were injected into the intraperitoneal (IP) cavity of mice, along with a solution of PCL-2 and D-cysteine. The animals were then imaged using a CCD camera to detect the luciferin formed following deprotection of PCL-2 by $H_2O_2$ and in situ cyclization with D-cysteine. These imaging experiments revealed a detection limit of ca. 0.5 µmol $H_2O_2$ and a robust increase in luciferin production as a function of $H_2O_2$ dose, with a ca. 10-fold turn-on in bioluminescent signal following treatment with 4.5 µmol $H_2O_2$ (FIG. 13). Comparison of PCL-2 to PCL-1 imaging under optimized imaging conditions for each probe indicated that PCL-1 has a lower detection limit for $H_2O_2$ than PCL-2 in vivo (0.037 µmol versus 0.5 µmol), while PCL-2 showed an increased fold turn-on when higher amounts of $H_2O_2$ are injected (6.4-fold with 1.5 µmol $H_2O_2$ for PCL-2 versus 3.6-fold with 2.4 µmol $H_2O_2$ for PCL-1; Table 3).

TABLE 3

| $H_2O_2$, µmol | Turn-on, PCL-2 (0.05 µmol) | Turn-on, PCL-1 (0.5 µmol) |
| --- | --- | --- |
| 0.037 | N/A | 1.5-fold |
| 0.15 | N/A | 2.0-fold |
| 0.5 | 2.8-fold | N/A |
| 0.6 | N/A | 2.7-fold |
| 1.5 | 6.4-fold | N/A |
| 2.4 | N/A | 3.6-fold |
| 4.5 | 10.3-fold | N/A |

In additional experiments to further show that $H_2O_2$ is required for the turn-on bioluminescent response, a separate group of mice was treated with 1.5 µmol $H_2O_2$ in the presence or absence of N-acetyl-L-cysteine (NAC), a small-molecule $H_2O_2$ scavenger. See, e.g., Winterbourn et al., *Free Radical Biol. Med.* (1999) 27, 322-328. In the absence of NAC, a robust bioluminescent signal was detected; however, upon NAC addition the bioluminescent signal was considerably attenuated (FIG. 13), thus providing evidence that the signal increase observed with $H_2O_2$ injection is a result of reaction of the PCL-2 probe with $H_2O_2$ in vivo. Finally, additional control experiments with a solution of HCBT and D-cysteine showed no change in the luciferin bioluminescent signal upon treatment with either $H_2O_2$ or NAC (FIG. 14).

In Vivo Detection of Endogenous $H_2O_2$ Fluxes and Caspase 8 Activity During Acute Inflammation.

Building on the results from these in vitro and in vivo experiments, the PCL-2 and IETDC probes were next applied to the individual detection of their respective bioanalytes in a murine model of acute inflammation. As stated previously, both $H_2O_2$ and caspase 8 play important roles in the development and progression of the inflammatory response, wherein $H_2O_2$ has been found to be important for eradication of pathogens (see, e.g., Lambeth, *Nat. Rev. Immunol.* (2004) 4, 181-189; Segal, *Annu. Rev. Immunol.* (2005) 23, 197-223; and Djaldetti et al., *Microsc. Res. Tech.* (2002) 57, 421-431), as well as playing a role in cellular signaling. See, e.g., Forman et al., *Am. J. Respir. Crit. Care Med.* (2002) 166, S4-S8; Savina et al., *Immunol. Rev.* (2007) 219, 143-156; Michalek et al., *J. Immunol.* (2007) 179, 6456-6467; Brown et al., *Free Radical Biol. Med.* (2009) 47, 1239-1253. Caspase 8 is important in its own right as one of the key initiators of the apoptotic cell-death pathway that is often initiated during inflammation. See, e.g., Hotchkiss et al., *Nat. Rev. Immunol.* (2006) 6, 813-822; Bannerman et al., *Am. J. Physiol. Lung Cell Mol. Physiol.* (2003) 284, L899-L914; and Ma et al., *J. Biol. Chem.* (2005) 280, 41827-41834. To monitor these two analytes individually, an acute inflammatory response was induced via injection of mice with lipopolysaccharides (LPS), a lipoglycan found on the surface of pathogenic bacteria that causes an inflammatory response in vivo. See, e.g., Parrillo, *N. Engl. J. Med.* (1993) 328, 1471-1477; Rietschel et al., *FASEB J.* (1994) 8, 217-225; Raetz et al., *Annu. Rev. Biochem.* (2002) 71, 635-700; Trent, et al., *J. Endotoxin Res.* (2006) 12, 205-223.

For $H_2O_2$ detection during inflammation, mice were treated with LPS or vehicle 6 h prior to injection of PCL-2 and D-cysteine. These studies indicated a ca. 3.7-fold turn-on in response to LPS stimulation, with a 55% reduction in signal upon treatment with apocynin (FIG. 15a,b, see, e.g., Wang et al., *Am. J. Respir. Crit. Care Med.* (1994) 150, 1449-1452; Zhang et al., *J. Hypertens.* (2010) 28, 806-816; and Choi et al., *J. Neurochem.* (2012) 120, 292-301), an antioxidant and broad-spectrum inhibitor of NADPH oxidase enzymes that are a major source of ROS production during inflammation and the general immune response. See, e.g., Forman et al., *Am. J. Respir. Crit. Care Med.* (2002) 166, S4-S8; Lambeth, *Nat. Rev. Immunol.* (2004) 4, 181-189; Griendling, *Free Radical Biol. Med.* (2009) 47, 1239-1253; and Nauseef, *J. Biol. Chem.* (2008) 283, 16961-16965. The increase in bioluminescent signal detected upon LPS treatment, as well as its attenuation by apocynin, indicate that PCL-2 successfully monitors alterations in endogenous $H_2O_2$ levels in living animals during inflammation. These data are further supported by previous, imaging-independent studies using ex vivo analysis of tissues or cells, which have shown an increase in ROS following LPS injection under similar conditions as demonstrated by lipid peroxidation and an increased oxidized to reduced glutathione ratio. See, e.g., Victor et al., M. *Free Radical Res.* 2003, 37, 919-929; Goraca et al., *J. Physiol. Pharmacol.* (2009) 60, 61-68; Singh et al., *Mol. Immunol.* (2012) 50, 244-252.

Parallel studies were completed with IETDC to verify its ability to monitor caspase 8 activity during acute inflammation in this same murine model. Treatment of FVB-luc$^+$ mice with LPS or vehicle 6 h prior to injection of IETDC and HCBT revealed an even greater increase in bioluminescent signal of ca. 18-fold (FIG. 15c,d). Furthermore, a 34% attenuation of the signal was afforded by injection of the pan-caspase inhibitor z-VD-OPh, a methyl ester protected analog of Q-VD-OPh, thus establishing that IETDC reliably monitors increased caspase 8 activity following LPS stimulation (FIG. 15c,d). Again, this increase in caspase 8 activity upon LPS stimulation is supported by ex vivo tissue studies that indicate increased caspase 8 expression and cleavage of procaspase 8 to form active caspase 8 following treatment with LPS. See, e.g., Alikhani et al., *J. Dent. Res.* (2004) 83, 671-676; and Supinski et al., *Am. J. Physiol. Regul. Integr. Comp. Physiol.* (2009) 297, R825-R834.

To verify that both apocynin and z-VD-OPh have no affect on the luciferin bioluminescent signal, a solution of HCBT and D-cysteine was injected following apocynin, z-VD-OPh, or vehicle injection. Detection of the resultant bioluminescent signal indicated that apocynin and z-VD-OPh do not alter the luciferin signal in vivo (FIG. 16). Taken together, these data indicate an increase in both the level of $H_2O_2$ and the activity of caspase 8 in living mice during acute inflammation.

In Vivo Dual-Analyte Detection of Endogenous $H_2O_2$ and Caspase 8 Activity During Acute Inflammation.

After confirming the individual abilities of the PCL-2 and IETDC probes to detect alterations in endogenous $H_2O_2$ levels and caspase 8 activity, respectively, in living animals in an inflammation disease model, these two probes were next used for simultaneous detection of both bioanalytes in vivo. For these studies, LPS was again used to provoke an acute inflammatory response in FVB-luc$^+$ mice. Initial experiments with PCL-2 and IETDC in control animals not treated with LPS demonstrated that injection of both probes resulted in a very low bioluminescent signal (FIG. 17), indicating very low basal levels of $H_2O_2$ and/or caspase 8 activity. It was determined that induction of inflammation via treatment with LPS causes a 2.7-fold increase in bioluminescent signal (FIG. 17), verifying use of this luciferin-based molecular logic-gate system to indicate the simultaneous presence of both $H_2O_2$ and caspase 8 during acute inflammation.

Next, it was determined whether the turn-on signal for the dual-analyte molecular logic-gate system could be attenuated by reducing ROS and caspase 8 activity. For these experiments pre-treatment with the antioxidant ascorbic acid (Vitamin C) was used to reduce the level of $H_2O_2$, as previous literature suggests a potential clinical application of this antioxidant for treatment of sepsis and other inflammatory responses. Pleiner et al., *Circulation* (2002) 106, 1460-1464; Wilson, *Biofactors* (2009) 35, 5-13; and Fisher et al., *Crit. Care Med.* (2011) 39, 1454-1460. The caspase inhibitor z-VD-OPh was used for reduction of caspase 8 activity. As expected, use of both these compounds resulted in a 30% decrease in bioluminescent signal (FIG. 17), indicating the utility of PCL-2 and IETDC for dual-analyte detection of $H_2O_2$ and caspase 8 during acute inflammation. Further, injection of ascorbic acid did not impact the bioluminescent signal from HCBT and D-cysteine (FIG. 18), demonstrating that this vitamin alone does not alter the bioluminescent signal of luciferin. The successful application of PCL-2 and IETDC in this in vivo model of inflammation demonstrated not only the ability of both probes to detect their respective single analytes in living animals, but further establishes the tandem use of PCL-2 and IETDC to detect the concomitant increase in two different biochemical events using a single bioluminescent reporter system.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detection of endogenous $H_2O_2$ and caspase 8 activity in a test subject, the method comprising:
   a) contacting the test subject with:
      i) a compound of Formula (Ia):

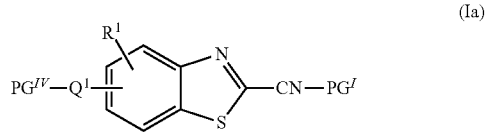

wherein:
Q¹ is a heteroatom functional group selected from —O— and —NR^{Q1}—;
R^{Q1} is selected from hydrogen, alkyl, and substituted alkyl;
PG^{IV} is an aryl or heteroaryl boronic acid-containing protecting group for the heteroatom functional group;
R¹ is selected from hydrogen, halogen, hydroxyl, alkyl, substituted alkyl, alkoxy, amino, and substituted amino; and
PG^{I} is an optional protecting group for the cyano group; and
ii) a compound of Formula (VIa):

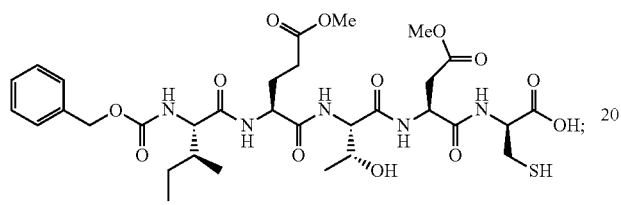

and
b) monitoring the test subject for luminescence, wherein luminescence indicates the presence of endogenous $H_2O_2$ and caspase 8 activity.

2. A method for detection of endogenous $H_2O_2$ and caspase 8 activity in a test subject, the method comprising:
a) contacting the test subject with:
i) a compound of Formula (Ia):

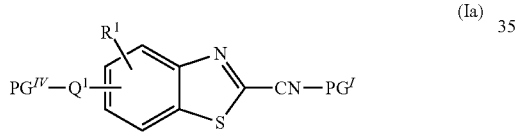
(Ia)

wherein:
Q¹ is a heteroatom functional group selected from —O— and —NR^{Q1}—;
R^{Q1} is selected from hydrogen, alkyl, and substituted alkyl;
PG^{IV} is an aryl or heteroaryl boronic acid-containing protecting group for the heteroatom functional group;
R¹ is selected from hydrogen, halogen, hydroxyl, alkyl, substituted alkyl, alkoxy, amino, and substituted amino; and
PG^{I} is an optional protecting group for the cyano group; and
ii) a compound of Formula VIa:

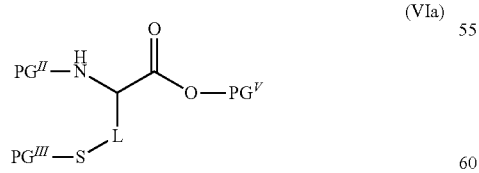
(VIa)

wherein
PG^{II} is a protecting group for an amino group;
PG^{II} forms a masked amino group in which the masked amino group is a carbamate or an amide;
PG^{III} is a protecting group for a thiol group;
PG^{V} is hydrogen or a protecting group for a carboxyl group; and
L is $C_{1-2}$ alkylene, $C_{1-2}$ alkenylene, or $C_{1-2}$ alkynylene; and
b) monitoring the test subject for luminescence, wherein luminescence indicates the presence of endogenous $H_2O_2$ and caspase 8 activity.

3. A method for detection of endogenous $H_2O_2$ and caspase 8 activity in a test subject, the method comprising:
a) contacting the test subject with:
i) a compound of Formula (Ia):

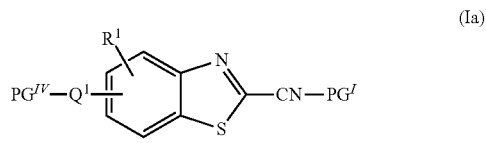
(Ia)

wherein:
Q¹ is a heteroatom functional group selected from —O— and —NR^{Q1}—;
R^{Q1} is selected from hydrogen, alkyl, and substituted alkyl;
PG^{IV} is an aryl or heteroaryl boronic acid-containing protecting group for the heteroatom functional group;
R¹ is selected from hydrogen, halogen, hydroxyl, alkyl, substituted alkyl, alkoxy, amino, and substituted amino; and
PG^{I} is a protecting group for the cyano group; and
ii) a compound of Formula VIa:

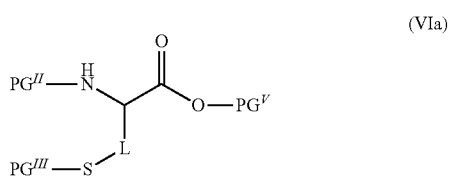
(VIa)

wherein
PG^{II} is a protecting group for an amino group;
PG^{II} forms a masked amino group in which the masked amino group is a carbamate or an amide;
PG^{III} is hydrogen or a protecting group for a thiol group;
PG^{V} is hydrogen or a protecting group for a carboxyl group; and
L is $C_{1-2}$ alkylene, $C_{1-2}$ alkenylene, or $C_{1-2}$ alkynylene; and
b) monitoring the test subject for luminescence, wherein luminescence indicates the presence of endogenous $H_2O_2$ and caspase 8 activity.

4. The method of claim 3, wherein PG^{III} is a protecting group for a thiol group.

5. The method of claim 3, wherein PG^{IV} has the formula

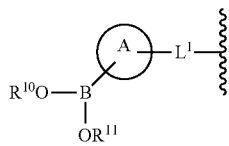

wherein:
R¹⁰ and R¹¹ are hydrogen;
A ring is selected from aryl, substituted aryl, heteroaryl and substituted heteroaryl; and
L¹ is a cleavable linker group.

6. The method of claim 3, wherein the compound of Formula (VIa) has the formula (VIb):
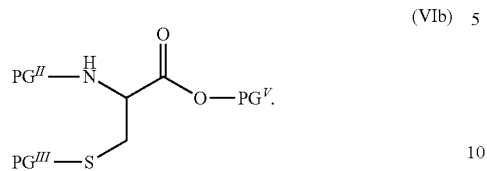
7. The method of claim 3, wherein the compound of Formula (VIa) has the formula:
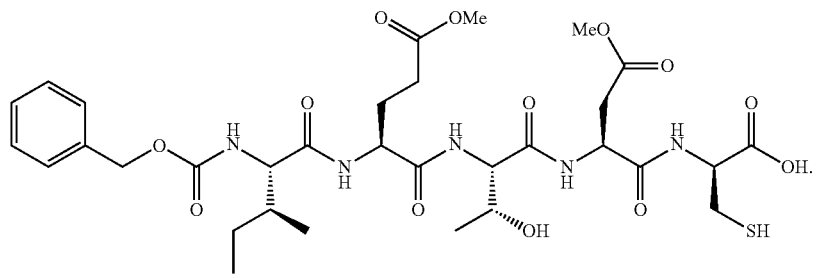 [SMILES: CC[C@H](C)[C@H](NC(=O)OCc1ccccc1)C(=O)N[C@@H](CCC(=O)OC)C(=O)N[C@H](C(=O)N[C@@H](CC(=O)OC)C(=O)N[C@H](CS)C(=O)O)[C@@H](C)O]
* * * * *

UNITED STATES PATENT AND TRADEMARK OFFICE
CERTIFICATE OF CORRECTION

PATENT NO. : 10,328,161 B2
APPLICATION NO. : 14/866321
DATED : June 25, 2019
INVENTOR(S) : Chang et al.

Page 1 of 1

It is certified that error appears in the above-identified patent and that said Letters Patent is hereby corrected as shown below:

In the Specification

<u>Column 40, Line 50, should read:</u>
IIIa (unprotected form) and a compound of Formula VIa Signed and Sealed this
Tenth Day of September, 2019

Andrei Iancu
*Director of the United States Patent and Trademark Office*